US007381701B2

(12) United States Patent
Chakrabarty et al.

(10) Patent No.: US 7,381,701 B2
(45) Date of Patent: Jun. 3, 2008

(54) COMPOSITIONS AND METHODS FOR TREATING CONDITIONS RELATED TO EPHRIN SIGNALING WITH CUPREDOXINS

(75) Inventors: Ananda Chakrabarty, Villa Park, IL (US); Tapas Das Gupta, River Forest, IL (US); Tohru Yamada, Oak Park, IL (US); Anita Chaudhari, Clifton Park, NY (US); Arsenio Fialho, Lisbon (PT); Yonghua Zhu, Chicago, IL (US)

(73) Assignee: The Borad of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 11/436,592

(22) Filed: May 19, 2006

(65) Prior Publication Data

US 2008/0089878 A1    Apr. 17, 2008

Related U.S. Application Data

(63) Continuation-in-part of application No. 10/720,603, filed on Nov. 24, 2003, which is a continuation-in-part of application No. 10/047,710, filed on Jan. 15, 2002, now Pat. No. 7,084,105.

(60) Provisional application No. 60/764,749, filed on Feb. 3, 2006, provisional application No. 60/682,812, filed on May 20, 2005, provisional application No. 60/616,782, filed on Oct. 7, 2004, provisional application No. 60/680,500, filed on May 13, 2005, provisional application No. 60/414,550, filed on Aug. 15, 2003, provisional application No. 60/269,133, filed on Feb. 15, 2001.

(51) Int. Cl.
*A61K 38/00* (2006.01)
*C07K 7/00* (2006.01)
*C07K 14/00* (2006.01)

(52) U.S. Cl. ............................ 514/2; 530/324; 530/326
(58) Field of Classification Search ...................... None
See application file for complete search history.

(56) References Cited

U.S. PATENT DOCUMENTS 5,210,019 A * 5/1993 Margalit ..................... 435/7.32
2003/0105000 A1* 6/2003 Pero et al. ..................... 514/12

FOREIGN PATENT DOCUMENTS

WO    WO 02/076380 A3    10/2002

OTHER PUBLICATIONS

Bowie et al (Science, 1990, 257:1306-1310).*
Burgess et al (J of Cell Bio. 111:2129-2138, 1990).*
Lazar et al (Molecular and Cellular Biology, 1988, 8:1247-1252).*
Scott et al (Nature Genetics, 1999, 21:440-443).*
Bork (Genome Research, 2000, 10:398-400).*
Freshney (Culture of Animal Cells, A Manual of Basic Technique, Alan R. Liss, Inc., 1983, New York, p. 4).*
Dermer (Bio/Technology, 1994, 12:320).*
Drexler et al (Leukemia and Lymphoma, 1993, 9:1-25).*
Zellner et al (Clin. Can. Res., 1998, 4:1797-17802).*
Zips et al (In vivo, 2005, 19:1-8).*
Gura (Science, 1997, 278:1041-1042).*
Kaiser (Science, 2006, 313, 1370).*
Canters (FEBS Letters, 1987, 212:168-172).*
Voet and Voet (Biochemistry, 1990, p. 298-301).*
Stratagene Catalog 1988, p. 39.*
Yamada T, et al.,"Internalization of bacterial redox protein azurin in mammalian cells: entry domain and specificity", *Cell Microbiol.* Oct. 2005; 7(10):1418-31.
Yamada T, et al., "Rusticyanin, a bacterial electron transfer protein, causes G1 arrest in J774 and apoptosis in human cancer cells", *Cell Cycle* Sep. 2004; 3(9):1182-7.
Yamada T, et al.,"Regulation of mammalian cell growth and death by bacterial redox proteins: relevance to ecology and cancer therapy", *Cell Cycle* Jun. 2004;3(6):752-5.
Hiraoka Y, et al., "Modulation of mammalian cell growth and death by prokaryotic and eukaryotic cytochrome c", *Proc Natl Acad Sci U S A.* Apr. 27, 2004;101(17):6427-32.
Yamada T, et al., "Apoptosis or growth arrest: Modulation of tumor suppressor p53's specificity by bacterial redox protein azurin", *Proc Natl Acad Sci U S A.* Apr. 6, 2004; 101(14):4770-5.
Punj V, et al., "Bacterial cupredoxin azurin as an inducer of apoptosis and regression in human breast cancer", *Oncogene* Mar. 25, 2004;23(13):2367-78.
Chakrabarty AM, "Microorganisms and Cancer: Quest for a Therapy", *J. Bacteriol.* 185(9):2683-86.
Punj V, et al., "Bacterial cupredoxin azurin and its interactions with the tumor suppressor protein p53", *Biochem Biophys Res Commun.* Dec. 5, 2003;312(1):109-14.
Punj V, et al., "Energy-generating enzymes of *Burkholderia cepacia* and their interactions with macrophages", *J Bacteriol.* May 2003;185(10):3167-78.
Goto M, et al., "Induction of apoptosis in macrophages by *Pseudomonas aeruginosa* azurin: tumour-suppressor protein p53 and reactive oxygen species, but not redox activity, as critical elements in cytotoxicity", *Mol Microbiol.* Jan. 2003;47(2):549-59.
Yamada T, et al., "The bacterial redox protein azurin induces apoptosis in J774 macrophages through complex formation and stabilization of the tumor suppressor protein p53", *Infect Immun.* Dec. 2002;70(12):7054-62.

(Continued)

*Primary Examiner*—Susan Ungar
*Assistant Examiner*—Peter J. Reddig
(74) *Attorney, Agent, or Firm*—Sheppard Mullin Richter & Hampton, LLP

(57) ABSTRACT

The present invention relates to compositions and methods of use of cupredoxins, and variants, derivatives and structural equivalents of cupredoxins that interfere with the ephrin signaling system in mammalian cells. Specifically, the invention relates to compositions and methods that use cupredoxins, such as azurin, rusticyanin and plastocyanin, and variants, derivatives and structural equivalents thereof, to treat cancer in mammals.

5 Claims, 10 Drawing Sheets

OTHER PUBLICATIONS

Yamada T, et al., "Bacterial redox protein azurin, tumor suppressor protein p53, and regression of cancer", *Proc Natl Acad Sci U S A.* Oct. 29, 2002;99(22):14098-103. Epub Oct. 22, 2002.

Zaborina O, et al., "P2Z-Independent and P2Z receptor-mediated macrophage killing by *Pseudomonas aeruginosa* isolated from cystic fibrosis patients", *Infect Immun.* Oct. 1999;67(10):5231-42.

Zaborina O, et al., "Secreted products of a nonmucoid *Pseudomonas aeruginosa* strain induce two modes of macrophage killing: external-ATP-dependent, P2Z-receptor-mediated necrosis and ATP-independent, caspase-mediated apoptosis", *Microbiology* Oct. 2000; 146 ( Pt 10):2521-30.

Yang D., et al., "Bacterial redox protein azurin induce apoptosis in human osteosarcoma U2OS cells", *Pharmacological Research* 2005 52(5):413-421.

Apiyo D. and Wittung-Stafshede, P., "Unique complex between bacterial azurin and tumor-suppressor protein p53", *Bioche. Biophys. Res. Comm.* 2005 332: 965-968.

Ye, Z., et al. "Selective inducement effect of bacterial redox protein azurin on apoptosis of human osteosarcoma cell line U2OS", *Chinese Journal of Cancer* 2005, 24(3): 298-304.

Yamada et al., "The Bacterial Redox Protein Azurin Induces Apoptosis in J774 Macrophages through Complex Formation and Stabilization of the Tumor Suppressor Protein p53", *Infection and Immunity*, vol. 70 (12), Dec. 2002, pp. 7054-7062.

Anonymous: "Plastocyanin precursor" Database EMBL, Online, Nov. 1, 1997, XP002306632 abstract.

Anonymous: "Rusticyanin precursor" Database EMBL, Online, Mar. 1, 1992, XP002306633 abstract.

Anonymous: "Pseudoazurin precursor" Database EMBL, Online, Feb. 1, 1991, XP002306634 abstract.

Yamada T, et al., "Internalization of bacterial redox protein azurin in mammalian cells: entry domain and specificity", *Cell Microbiol.* Oct. 2005; 7(10):1418-31.

Yamada T, et al., "Internalization of bacterial redox protein azurin in mammalian cells: entry domain and specificity", *Cell Microbiol.* Oct. 2005;7(10):1418-31.

Yamada T, et al., "Rusticyanin, a bacterial electron transfer protein, causes G1 arrest in J774 and apoptosis in human cancer cells", *Cell Cycle* Sep. 2004;3(9):1182-7.

Yamada T, et al., "Regulation of mammalian cell growth and death by bacterial redox proteins: relevance to ecology and cancer therapy", *Cell Cycle* Jun. 2004;3(6):752-5.

Hiraoka Y, et al., "Modulation of mammalian cell growth and death by prokaryotic and eukaryotic cytochrome c", *Proc Natl Acad Sci U S A.* Apr. 27, 2004;101(17):6427-32.

Yamada T, et al., "Apoptosis or growth arrest: Modulation of tumor suppressor p53's specificity by bacterial redox protein azurin", *Proc Natl Acad Sci U S A.* Apr. 6, 2004;101(14):4770-5.

Punj V, et al., "Bacterial cupredoxin azurin as an inducer of apoptosis and regression in human breast cancer", *Oncogene* Mar. 25, 2004;23(13):2367-78.

Chakrabarty AM, "Microorganisms and Cancer: Quest for a Therapy", *J. Bacteriol.* 185(9):2683-86, May, 2003.

Punj V, et al., "Bacterial cupredoxin azurin and its interactions with the tumor suppressor protein p53", *Biochem Biophys Res Commun.* Dec. 5, 2003;312(1):109-14.

Punj V, et al., "Energy-generating enzymes of *Burkholderia cepacia* and their interactions with macrophages", *J Bacteriol.* May 2003;185(10):3167-78.

Goto M, et al., "Induction of apoptosis in macrophages by *Pseudomonas aeruginosa* azurin: tumour-suppressor protein p53 and reactive oxygen species, but not redox activity, as critical elements in cytotoxicity", *Mol Microbiol.* Jan. 2003;47(2):549-59.

Yamada T, et al., "The bacterial redox protein azurin induces apoptosis in J774 macrophages through complex formation and stabilization of the tumor suppressor protein p53", *Infect Immun.* Dec. 2002;70(12):7054-62.

Yamada T, et al., "Bacterial redox protein azurin, tumor suppressor protein p53, and regression of cancer", *Proc Natl Acad Sci U S A.* Oct. 29, 2002;99(22):14098-103. Epub Oct. 22, 2002.

Zaborina O, et al., "P2Z-Independent and P2Z receptor-mediated macrophage killing by *Pseudomonas aeruginosa* isolated from cystic fibrosis patients", *Infect Immun.* Oct. 1999;67(10):5231-42.

Zaborina O, et al., "Secreted products of a nonmucoid *Pseudomonas aeruginosa* strain induce two modes of macrophage killing: external-ATP-dependent, P2Z-receptor-mediated necrosis and ATP-independent, caspase-mediated apoptosis", *Microbiology* Oct. 2000; 146 ( Pt 10):2521-30.

Yang D., et al., "Bacterial redox protein azurin induce apoptosis in human osteosarcoma U2OS cells", *Pharmacological Research* 2005 52(5):413-421.

Apiyo D. and Wittung-Stafshede, P., "Unique complex between bacterial azurin and tumor-suppressor protein p53", *Bioche. Biophys. Res. Comm.* 2005 332: 965-968.

Ye. Z., et al. "Selective inducement effect of bacterial redox protein azurin on apoptosis of human osteosarcoma cell line U2OS", *Chinese Journal of Cancer* 2005, 24(3): 298-304.

* cited by examiner

```
                    10        20        30        40        50        60
              ....*....|....*....|....*....|....*....|....*....|....*....|
1JZG_A   1    AECSVDIQGndqm~~~qfntNAITVDKscKQFTVNLSHPgnl~~pkNVMGHNWVLSTAAD  55
1KGY_E   1    IVLEPIYWNssnskflpgggLVLYPQI~~GDKLDIICPKvdsktvgQYEYYKVYMVDKDQ  58
                    70        80        90       100       110       120

....*....|....*....|....*....|....*....|....*....|....*....|
1JZG_A   56   MQGVVTDgmasgldkdylkpddsrviaHTKLIGSG~EKDSVTF DVS~~~~~~~~~~KLKEG  105
1KGY_E   59   ADRCTIKke~~~~~~~~~~~~~~~ntPLLNCARPdQDVKFTI KFQefspnlwglEFQKN  102
                   130       140       150

...|....*....|....*....|....*....|.....*.
1JZG_A  106   EQY MFFCTFPgh~~~~~~~~~~~sALMKGTLTLK  128
1KGY_E  103   KDY YIISTSNgsleglldnqeggvcqtRAMKILMKVG  138
```

Figure 1

```
Azurin                      D S V T F D V │S - - - - - - - - - K L K E G│E Q Y M F F C T G-H loop of human
ephrin B-2                  V K F T I K F │Q e f s p n l w g l E F Q K N│K D Y Y I I S T Rusticyanin                 Y T N F T W H │p - - - - - - - - - - - T A│G T Y Y Y V C Q G-H loop of human
ephrin B-2                  V K F T I K F │q e f s p n l w g l e f q K N│K D Y Y I I S T Auracyanin                  S G S v - - - │- - - - - - - - - t F R T P A│G T Y L Y I C T G-H loop of human
ephrin B-2                  V K F t i k f │q e f s p n l w g L E F Q K N│K D Y Y I I S T Plastocyanin                E T V V R K L │S t - - - - - - - - - - - p│G V Y G V Y C E G-H loop of human
ephrin B-2                  V K F T I K F │Q e f s p n l w g l e f q k n│K D Y Y I I S T Cucumber protein            G R D Q i k - │- - - - - - - - - - - l p K│G Q S Y F I C N G-H loop of human
ephrin B-2                  V K F T i k f │q e f s p n l w g l e f q k N│K D Y Y I I S T Stellacyanin                S P V I E R L │d e - - - - - - - - - - - l│G M H Y F V C T G-H loop of human
ephrin B-2                  V K F T I K F │q e f s p n l w g l e f q k n│K D Y Y I I S T
```

Figure 2

```
                       SEQUENCE LISTING

<160> NUMBER OF SEQ ID NOS: 34

<210> SEQ ID NO 1
<211> LENGTH: 128
<212> TYPE: PRT
<213> ORGANISM: Pseudomonas aeruginosa

<400> SEQUENCE: 1

Ala Glu Cys Ser Val Asp Ile Gln Gly Asn Asp Gln Met Gln Phe Asn
1               5                   10                  15

Thr Asn Ala Ile Thr Val Asp Lys Ser Cys Lys Gln Phe Thr Val Asn
            20                  25                  30

Leu Ser His Pro Gly Asn Leu Pro Lys Asn Val Met Gly His Asn Trp
        35                  40                  45

Val Leu Ser Thr Ala Ala Asp Met Gln Gly Val Val Thr Asp Gly Met
    50                  55                  60

Ala Ser Gly Leu Asp Lys Asp Tyr Leu Lys Pro Asp Asp Ser Arg Val
65                  70                  75                  80

Ile Ala His Thr Lys Leu Ile Gly Ser Gly Glu Lys Asp Ser Val Thr
                85                  90                  95

Phe Asp Val Ser Lys Leu Lys Glu Gly Glu Gln Tyr Met Phe Phe Cys
            100                 105                 110

Thr Phe Pro Gly His Ser Ala Leu Met Lys Gly Thr Leu Thr Leu Lys
        115                 120                 125

<210> SEQ ID NO 2
<211> LENGTH: 105
<212> TYPE: PRT
<213> ORGANISM: Phormidium laminosum

<400> SEQUENCE: 2

Glu Thr Phe Thr Val Lys Met Gly Ala Asp Ser Gly Leu Leu Gln Phe
1               5                   10                  15
```

Glu Pro Ala Asn Val Thr Val His Pro Gly Asp Thr Val Lys Trp Val
            20                  25                  30

Asn Asn Lys Leu Pro Pro His Asn Ile Leu Phe Asp Lys Gln Val
            35                  40                  45

Pro Gly Ala Ser Lys Glu Leu Ala Asp Lys Leu Ser His Ser Gln Leu
 50                  55                  60

Met Phe Ser Pro Gly Glu Ser Tyr Glu Ile Thr Phe Ser Ser Asp Phe
 65                  70                  75                  80

Pro Ala Gly Thr Tyr Thr Tyr Tyr Cys Ala Pro His Arg Gly Ala Gly
                85                  90                  95

Met Val Gly Lys Ile Thr Val Glu Gly
            100                 105

<210> SEQ ID NO 3
<211> LENGTH: 155
<212> TYPE: PRT
<213> ORGANISM: Thiobacillus ferrooxidans

<400> SEQUENCE: 3

Gly Thr Leu Asp Thr Thr Trp Lys Glu Ala Thr Leu Pro Gln Val Lys
 1               5                  10                  15

Ala Met Leu Glu Lys Asp Thr Gly Lys Val Ser Gly Asp Thr Val Thr
            20                  25                  30

Tyr Ser Gly Lys Thr Val His Val Ala Ala Ala Val Leu Pro Gly
            35                  40                  45

Phe Pro Phe Pro Ser Phe Glu Val His Asp Lys Lys Asn Pro Thr Leu
 50                  55                  60

Glu Ile Pro Ala Gly Ala Thr Val Asp Val Thr Phe Ile Asn Thr Asn
 65                  70                  75                  80

Lys Gly Phe Gly His Ser Phe Asp Ile Thr Lys Lys Gly Pro Pro Tyr
                85                  90                  95

Ala Val Met Pro Val Ile Asp Pro Ile Val Ala Gly Thr Gly Phe Ser
            100                 105                 110

Pro Val Pro Lys Asp Gly Lys Phe Gly Tyr Thr Asp Phe Thr Trp His
            115                 120                 125

Pro Thr Ala Gly Thr Tyr Tyr Tyr Val Cys Gln Ile Pro Gly His Ala
            130                 135                 140

Ala Thr Gly Met Phe Gly Lys Ile Val Val Lys
145                 150                 155

<210> SEQ ID NO 4
<211> LENGTH: 124
<212> TYPE: PRT
<213> ORGANISM: Achromabacter cycloclastes

<400> SEQUENCE: 4

Ala Asp Phe Glu Val His Met Leu Asn Lys Gly Lys Asp Gly Ala Met
 1               5                  10                  15

Val Phe Glu Pro Ala Ser Leu Lys Val Ala Pro Gly Asp Thr Val Thr
            20                  25                  30

Phe Ile Pro Thr Asp Lys Gly His Asn Val Glu Thr Ile Lys Gly Met
            35                  40                  45

Ile Pro Asp Gly Ala Glu Ala Phe Lys Ser Lys Ile Asn Glu Asn Tyr
 50                  55                  60

Lys Val Thr Phe Thr Ala Pro Gly Val Tyr Gly Val Lys Cys Thr Pro
 65                  70                  75                  80

```
His Tyr Gly Met Gly Met Val Gly Val Val Gln Val Gly Asp Ala Pro
                85                  90                  95

Ala Asn Leu Glu Ala Val Lys Gly Ala Lys Asn Pro Lys Lys Ala Gln
            100                 105                 110

Glu Arg Leu Asp Ala Ala Leu Ala Ala Leu Gly Asn
        115                 120

<210> SEQ ID NO 5
<211> LENGTH: 128
<212> TYPE: PRT
<213> ORGANISM: Alcaligenes faecalis

<400> SEQUENCE: 5

Ala Cys Asp Val Ser Ile Glu Gly Asn Asp Ser Met Gln Phe Asn Thr
1               5                   10                  15

Lys Ser Ile Val Val Asp Lys Thr Cys Lys Glu Phe Thr Ile Asn Leu
            20                  25                  30

Lys His Thr Gly Lys Leu Pro Lys Ala Ala Met Gly His Asn Val Val
        35                  40                  45

Val Ser Lys Lys Ser Asp Glu Ser Ala Val Ala Thr Asp Gly Met Lys
50                  55                  60

Ala Gly Leu Asn Asn Asp Tyr Val Lys Ala Gly Asp Glu Arg Val Ile
65                  70                  75                  80

Ala His Thr Ser Val Ile Gly Gly Glu Thr Asp Ser Val Thr Phe
                85                  90                  95

Asp Val Ser Lys Leu Lys Glu Gly Glu Asp Tyr Ala Phe Phe Cys Ser
            100                 105                 110

Phe Pro Gly His Trp Ser Ile Met Lys Gly Thr Ile Glu Leu Gly Ser
        115                 120                 125

<210> SEQ ID NO 6
<211> LENGTH: 129
<212> TYPE: PRT
<213> ORGANISM: Achromobacter xylosoxidans ssp. denitrificans I

<400> SEQUENCE: 6

Ala Gln Cys Glu Ala Thr Ile Glu Ser Asn Asp Ala Met Gln Tyr Asn
1               5                   10                  15

Leu Lys Glu Met Val Val Asp Lys Ser Cys Lys Gln Phe Thr Val His
            20                  25                  30

Leu Lys His Val Gly Lys Met Ala Lys Val Ala Met Gly His Asn Trp
        35                  40                  45

Val Leu Thr Lys Glu Ala Asp Lys Gln Gly Val Ala Thr Asp Gly Met
    50                  55                  60

Asn Ala Gly Leu Ala Gln Asp Tyr Val Lys Ala Gly Asp Thr Arg Val
65                  70                  75                  80

Ile Ala His Thr Lys Val Ile Gly Gly Gly Glu Ser Asp Ser Val Thr
                85                  90                  95

Phe Asp Val Ser Lys Leu Thr Pro Gly Glu Ala Tyr Ala Tyr Phe Cys
            100                 105                 110

Ser Phe Pro Gly His Trp Ala Met Met Lys Gly Thr Leu Lys Leu Ser
        115                 120                 125

Asn

<210> SEQ ID NO 7
<211> LENGTH: 129
<212> TYPE: PRT
```

```
<213> ORGANISM: Bordetella bronchiseptica

<400> SEQUENCE: 7

Ala Glu Cys Ser Val Asp Ile Ala Gly Thr Asp Gln Met Gln Phe Asp
1               5                   10                  15

Lys Lys Ala Ile Glu Val Ser Lys Ser Cys Lys Gln Phe Thr Val Asn
            20                  25                  30

Leu Lys His Thr Gly Lys Leu Pro Arg Asn Val Met Gly His Asn Trp
        35                  40                  45

Val Leu Thr Lys Thr Ala Asp Met Gln Ala Val Glu Lys Asp Gly Ile
    50                  55                  60

Ala Ala Gly Leu Asp Asn Gln Tyr Leu Lys Ala Gly Asp Thr Arg Val
65              70                  75                  80

Leu Ala His Thr Lys Val Leu Gly Gly Gly Ser Asp Ser Val Thr
                85                  90                  95

Phe Asp Val Ala Lys Leu Ala Ala Gly Asp Asp Tyr Thr Phe Phe Cys
            100                 105                 110

Ser Phe Pro Gly His Gly Ala Leu Met Lys Gly Thr Leu Lys Leu Val
        115                 120                 125

Asp

<210> SEQ ID NO 8
<211> LENGTH: 129
<212> TYPE: PRT
<213> ORGANISM: Methylomonas sp. J.

<400> SEQUENCE: 8

Ala Ser Cys Glu Thr Thr Val Thr Ser Gly Asp Thr Met Thr Tyr Ser
1               5                   10                  15

Thr Arg Ser Ile Ser Val Pro Ala Ser Cys Ala Glu Phe Thr Val Asn
            20                  25                  30

Phe Glu His Lys Gly His Met Pro Lys Thr Gly Met Gly His Asn Trp
        35                  40                  45

Val Leu Ala Lys Ser Ala Asp Val Gly Asp Val Ala Lys Glu Gly Ala
    50                  55                  60

His Ala Gly Ala Asp Asn Asn Phe Val Thr Pro Gly Asp Lys Arg Val
65              70                  75                  80

Ile Ala Phe Thr Pro Ile Ile Gly Gly Gly Glu Lys Thr Ser Val Lys
                85                  90                  95

Phe Lys Val Ser Ala Leu Ser Lys Asp Glu Ala Tyr Thr Tyr Phe Cys
            100                 105                 110

Ser Tyr Pro Gly His Phe Ser Met Met Arg Gly Thr Leu Lys Leu Glu
        115                 120                 125

Glu

<210> SEQ ID NO 9
<211> LENGTH: 166
<212> TYPE: PRT
<213> ORGANISM: Neisseria meningitidis

<400> SEQUENCE: 9

Cys Ser Gln Glu Pro Ala Ala Pro Ala Glu Ala Thr Pro Ala

-continued

```
            35                  40                  45

Asn Asp Asn Met Gln Phe Asn Thr Lys Asp Ile Gln Val Ser Lys Ala
         50                  55                  60

Cys Lys Glu Phe Thr Ile Thr Leu Lys His Thr Gly Thr Gln Pro Lys
 65                  70                  75                  80

Thr Ser Met Gly His Asn Ile Val Ile Gly Lys Thr Glu Asp Met Asp
                 85                  90                  95

Gly Ile Phe Lys Asp Gly Val Gly Ala Ala Asp Thr Asp Tyr Val Lys
                100                 105                 110

Pro Asp Asp Ala Arg Val Val Ala His Thr Lys Leu Ile Gly Gly Gly
            115                 120                 125

Glu Glu Ser Ser Leu Thr Leu Asp Pro Ala Lys Leu Ala Asp Gly Glu
        130                 135                 140

Tyr Lys Phe Ala Cys Thr Phe Pro Gly His Gly Ala Leu Met Asn Gly
145                 150                 155                 160

Lys Val Thr Leu Val Asp
                165

<210> SEQ ID NO 10
<211> LENGTH: 166
<212> TYPE: PRT
<213> ORGANISM: Neisseria gonorrhoeae F62

<400> SEQUENCE: 10

Cys Ser Gln Glu Pro Ala Ala Pro Ala Ala Glu Ala Thr Pro Ala Gly
  1               5                  10                  15

Glu Ala Pro Ala Ser Glu Ala Pro Ala Ala Glu Ala Ala Pro Ala Asp
             20                  25                  30

Ala Ala Glu Ala Pro Ala Ala Gly Asn Cys Ala Ala Thr Val Glu Ser
         35                  40                  45

Asn Asp Asn Met Gln Phe Asn Thr Lys Asp Ile Gln Val Ser Lys Ala
     50                  55                  60

Cys Lys Glu Phe Thr Ile Thr Leu Lys His Thr Gly Thr Gln Pro Lys
 65                  70                  75                  80

Ala Ser Met Gly His Asn Leu Val Ile Ala Lys Ala Glu Asp Met Asp
                 85                  90                  95

Gly Val Phe Lys Asp Gly Val Gly Ala Ala Asp Thr Asp Tyr Val Lys
                100                 105                 110

Pro Asp Asp Ala Arg Val Val Ala His Thr Lys Leu Ile Gly Gly Gly
            115                 120                 125

Glu Glu Ser Ser Leu Thr Leu Asp Pro Ala Lys Leu Ala Asp Gly Asp
        130                 135                 140

Tyr Lys Phe Ala Cys Thr Phe Pro Gly His Gly Ala Leu Met Asn Gly
145                 150                 155                 160

Lys Val Thr Leu Val Asp
                165

<210> SEQ ID NO 11
<211> LENGTH: 128
<212> TYPE: PRT
<213> ORGANISM: Pseudomomas fluorescens

<400> SEQUENCE: 11

Ala Glu Cys Lys Thr Thr Ile Asp Ser Thr Asp Gln Met Ser Phe Asn
  1               5                  10                  15

Thr Lys Ala Ile Glu Ile Asp Lys Ala Cys Lys Thr Phe Thr Val Glu
```

```
                 20                  25                  30

Leu Thr His Ser Gly Ser Leu Pro Lys Asn Val Met Gly His Asn Leu
            35                  40                  45

Val Ile Ser Lys Gln Ala Asp Met Gln Pro Ile Ala Thr Asp Gly Leu
        50                  55                  60

Ser Ala Gly Ile Asp Lys Asn Tyr Leu Lys Glu Gly Asp Thr Arg Val
65                  70                  75                  80

Ile Ala His Thr Lys Val Ile Gly Ala Gly Glu Lys Asp Ser Leu Thr
                85                  90                  95

Ile Asp Val Ser Lys Leu Asn Ala Ala Glu Lys Tyr Gly Phe Phe Cys
               100                 105                 110

Ser Phe Pro Gly His Ile Ser Met Met Lys Gly Thr Val Thr Leu Lys
           115                 120                 125

<210> SEQ ID NO 12
<211> LENGTH: 128
<212> TYPE: PRT
<213> ORGANISM: Pseudomonas chlororaphis

<400> SEQUENCE: 12

Ala Glu Cys Lys Val Asp Val Asp Ser Thr Asp Gln Met Ser Phe Asn
1               5                  10                  15

Thr Lys Glu Ile Thr Ile Asp Lys Ser Cys Lys Thr Phe Thr Val Asn
            20                  25                  30

Leu Thr His Ser Gly Ser Leu Pro Lys Asn Val Met Gly His Asn Trp
            35                  40                  45

Val Leu Ser Lys Ser Ala Asp Met Ala Gly Ile Ala Thr Asp Gly Met
        50                  55                  60

Ala Ala Gly Ile Asp Lys Asp Tyr Leu Lys Pro Gly Asp Ser Arg Val
65                  70                  75                  80

Ile Ala His Thr Lys Ile Ile Gly Ser Gly Glu Lys Asp Ser Val Thr
                85                  90                  95

Phe Asp Val Ser Lys Leu Thr Ala Gly Glu Ser Tyr Glu Phe Phe Cys
               100                 105                 110

Ser Phe Pro Gly His Asn Ser Met Met Lys Gly Ala Val Val Leu Lys
           115                 120                 125

<210> SEQ ID NO 13
<211> LENGTH: 129
<212> TYPE: PRT
<213> ORGANISM: Xylella fastidiosa 9a5c

<400> SEQUENCE: 13

Lys Thr Cys Ala Val Thr Ile Ser Ala Asn Asp Gln Met Lys Phe Asp
1               5                  10                  15

Gln Asn Thr Ile Lys Ile Ala Ala Glu Cys Thr His Val Asn Leu Thr
            20                  25                  30

Leu Thr His Thr Gly Lys Lys Ser Ala Arg Val Met Gly His Asn Trp
            35                  40                  45

Val Leu Thr Lys Thr Thr Asp Met Gln Ala Val Ala Leu Ala Gly Leu
        50                  55                  60

His Ala Thr Leu Ala Asp Asn Tyr Val Pro Lys Ala Asp Pro Arg Val
65                  70                  75                  80

Ile Ala His Thr Ala Ile Ile Gly Gly Gly Glu Arg Thr Ser Ile Thr
                85                  90                  95

Phe Pro Thr Asn Thr Leu Ser Lys Asn Val Ser Tyr Thr Phe Phe Cys
```

```
                100               105               110
Ser Phe Pro Gly His Trp Ala Leu Met Lys Gly Thr Leu Asn Phe Gly
        115                 120                 125
Gly

<210> SEQ ID NO 14
<211> LENGTH: 138
<212> TYPE: PRT
<213> ORGANISM: Cucumis sativus

<400> SEQUENCE: 14

Met Gln Ser Thr Val His Ile Val Gly Asp Asn Thr Gly Trp Ser Val
1               5                   10                  15

Pro Ser Ser Pro Asn Phe Tyr Ser Gln Trp Ala Ala Gly Lys Thr Phe
            20                  25                  30

Arg Val Gly Asp Ser Leu Gln Phe Asn Phe Pro Ala Asn Ala His Asn
        35                  40                  45

Val His Glu Met Glu Thr Lys Gln Ser Phe Asp Ala Cys Asn Phe Val
    50                  55                  60

Asn Ser Asp Asn Asp Val Glu Arg Thr Ser Pro Val Ile Glu Arg Leu
65                  70                  75                  80

Asp Glu Leu Gly Met His Tyr Phe Val Cys Thr Val Gly Thr His Cys
                85                  90                  95

Ser Asn Gly Gln Lys Leu Ser Ile Asn Val Val Ala Ala Asn Ala Thr
            100                 105                 110

Val Ser Met Pro Pro Ser Ser Pro Ser Ser Val Met Pro
        115                 120                 125

Pro Pro Val Met Pro Pro Ser Pro Ser
    130                 135

<210> SEQ ID NO 15
<211> LENGTH: 162
<212> TYPE: PRT
<213> ORGANISM: Chloroflexus aurantiacus

<400> SEQUENCE: 15

Met Lys Ile Thr Leu Arg Met Met Val Leu Ala Val Leu Thr Ala Met
1               5                   10                  15

Ala Met Val Leu Ala Ala Cys Gly Gly Gly Ser Gly Gly Ser
            20                  25                  30

Thr Gly Gly Gly Ser Gly Ser Gly Pro Val Thr Ile Glu Ile Gly Ser
        35                  40                  45

Lys Gly Glu Glu Leu Ala Phe Asp Lys Thr Glu Leu Thr Val Ser Ala
    50                  55                  60

Gly Gln Thr Val Thr Ile Arg Phe Lys Asn Asn Ser Ala Val Gln Gln
65                  70                  75                  80

His Asn Trp Ile Leu Val Lys Gly Gly Glu Ala Glu Ala Ala Asn Ile
                85                  90                  95

Ala Asn Ala Gly Leu Ser Ala Gly Pro Ala Ala Asn Tyr Leu Pro Ala
            100                 105                 110

Asp Lys Ser Asn Ile Ile Ala Glu Ser Pro Leu Ala Asn Gly Asn Glu
        115                 120                 125

Thr Val Glu Val Thr Phe Thr Ala Pro Ala Ala Gly Thr Tyr Leu Tyr
    130                 135                 140

Ile Cys Thr Val Pro Gly His Tyr Pro Leu Met Gln Gly Lys Leu Val
145                 150                 155                 160
```

Val Asn

<210> SEQ ID NO 16
<211> LENGTH: 140
<212> TYPE: PRT
<213> ORGANISM: Chloroflexus aurantiacus

<400> SEQUENCE: 16

```
Ala Ala Asn Ala Pro Gly Gly Ser Asn Val Asn Glu Thr Pro Ala
1               5                   10                  15

Gln Thr Val Glu Val Arg Ala Ala Pro Asp Ala Leu Ala Phe Ala Gln
            20                  25                  30

Thr Ser Leu Ser Leu Pro Ala Asn Thr Val Val Arg Leu Asp Phe Val
        35                  40                  45

Asn Gln Asn Asn Leu Gly Val Gln His Asn Trp Val Leu Val Asn Gly
    50                  55                  60

Gly Asp Asp Val Ala Ala Ala Val Asn Thr Ala Ala Gln Asn Asn Ala
65                  70                  75                  80

Asp Ala Leu Phe Val Pro Pro Asp Thr Pro Asn Ala Leu Ala Trp
                85                  90                  95

Thr Ala Met Leu Asn Ala Gly Glu Ser Gly Ser Val Thr Phe Arg Thr
                100                 105                 110

Pro Ala Pro Gly Thr Tyr Leu Tyr Ile Cys Thr Phe Pro Gly His Tyr
            115                 120                 125

Leu Ala Gly Met Lys Gly Thr Leu Thr Val Thr Pro
    130                 135                 140
```

<210> SEQ ID NO 17
<211> LENGTH: 96
<212> TYPE: PRT
<213> ORGANISM: Cucumis sativus

<400> SEQUENCE: 17

```
Ala Val Tyr Val Val Gly Gly Ser Gly Gly Trp Thr Phe Asn Thr Glu
1               5                   10                  15

Ser Trp Pro Lys Gly Lys Arg Phe Arg Ala Gly Asp Ile Leu Leu Phe
            20                  25                  30

Asn Tyr Asn Pro Ser Met His Asn Val Val Val Asn Gln Gly Gly
        35                  40                  45

Phe Ser Thr Cys Asn Thr Pro Ala Gly Ala Lys Val Tyr Thr Ser Gly
    50                  55                  60

Arg Asp Gln Ile Lys Leu Pro Lys Gly Gln Ser Tyr Phe Ile Cys Asn
65                  70                  75                  80

Phe Pro Gly His Cys Gln Ser Gly Met Lys Ile Ala Val Asn Ala Leu
                85                  90                  95
```

<210> SEQ ID NO 18
<211> LENGTH: 18
<212> TYPE: PRT
<213> ORGANISM: Pseudomonas aeruginosa

<400> SEQUENCE: 18

```
Thr Phe Asp Val Ser Lys Leu Lys Glu Gly Glu Gln Tyr Met Phe Phe
1               5                   10                  15

Cys Thr
```

<210> SEQ ID NO 19

<211> LENGTH: 26
<212> TYPE: PRT
<213> ORGANISM: Pseudomonas aeruginosa

<400> SEQUENCE: 19

Gly Ser Gly Glu Lys Asp Ser Val Thr Phe Asp Val Ser Lys Leu Lys
1               5                   10                  15

Glu Gly Glu Gln Tyr Met Phe Phe Cys Thr
            20                  25

<210> SEQ ID NO 20
<211> LENGTH: 15
<212> TYPE: PRT
<213> ORGANISM: Ulva pertusa

<400> SEQUENCE: 20

Val Arg Lys Leu Ser Thr Pro Gly Val Tyr Gly Val Tyr Cys Glu
1               5                   10                  15

<210> SEQ ID NO 21
<211> LENGTH: 150
<212> TYPE: PRT
<213> ORGANISM: Vibrio parahaemolyticus

<400> SEQUENCE: 21

Met Ser Leu Arg Ile Leu Ala Ala Thr Leu Ala Leu Ala Gly Leu Ser
1               5                   10                  15

Phe Gly Ala Gln Ala Ser Ala Glu Cys Glu Val Ser Ile Asp Ala Asn
            20                  25                  30

Asp Met Met Gln Phe Ser Thr Lys Thr Leu Ser Val Pro Ala Thr Cys
        35                  40                  45

Lys Glu Val Thr Leu Thr Leu Asn His Thr Gly Lys Met Pro Ala Gln
    50                  55                  60

Ser Met Gly His Asn Val Val Ile Ala Asp Thr Ala Asn Ile Gln Ala
65                  70                  75                  80

Val Gly Thr Asp Gly Met Ser Ala Gly Ala Asp Asn Ser Tyr Val Lys
                85                  90                  95

Pro Asp Asp Glu Arg Val Tyr Ala His Thr Lys Val Val Gly Gly Gly
            100                 105                 110

Glu Ser Thr Ser Ile Thr Phe Ser Thr Glu Lys Met Thr Ala Gly Gly
        115                 120                 125

Asp Tyr Ser Phe Phe Cys Ser Phe Pro Gly His Trp Ala Ile Met Gln
    130                 135                 140

Gly Lys Phe Glu Phe Lys
145                 150

<210> SEQ ID NO 22
<211> LENGTH: 98
<212> TYPE: PRT
<213> ORGANISM: Ulva pertusa

<400> SEQUENCE: 22

Ala Gln Ile Val Lys Leu Gly Gly Asp Asp Gly Ser Leu Ala Phe Val
1               5                   10                  15

Pro Ser Lys Ile Ser Val Ala Ala Gly Glu Ala Ile Glu Phe Val Asn
            20                  25                  30

Asn Ala Gly Phe Pro His Asn Ile Val Phe Asp Glu Asp Ala Val Pro
        35                  40                  45

Ala Gly Val Asp Ala Asp Ala Ile Ser Tyr Asp Asp Tyr Leu Asn Ser

```
                50                  55                  60
Lys Gly Glu Thr Val Val Arg Lys Leu Ser Thr Pro Gly Val Tyr Gly
 65                  70                  75                  80

Val Tyr Cys Glu Pro His Ala Gly Ala Gly Met Lys Met Thr Ile Thr
                 85                  90                  95

Val Gln

<210> SEQ ID NO 23
<211> LENGTH: 138
<212> TYPE: PRT
<213> ORGANISM: Homo sapiens

<400> SEQUENCE: 23

Ile Val Leu Glu Pro Ile Tyr Trp Asn Ser Ser Asn Ser Lys Phe Leu
 1               5                  10                  15

Pro Gly Gly Gly Leu Val Leu Tyr Pro Gln Ile Gly Asp Lys Leu Asp
                20                  25                  30

Ile Ile Cys Pro Lys Val Asp Ser Lys Thr Val Gly Gln Tyr Glu Tyr
             35                  40                  45

Tyr Lys Val Tyr Met Val Asp Lys Asp Gln Ala Asp Arg Cys Thr Ile
         50                  55                  60

Lys Lys Glu Asn Thr Pro Leu Leu Asn Cys Ala Arg Pro Asp Gln Asp
 65                  70                  75                  80

Val Lys Phe Thr Ile Lys Phe Gln Glu Phe Ser Pro Asn Leu Trp Gly
                 85                  90                  95

Leu Glu Phe Gln Lys Asn Lys Asp Tyr Tyr Ile Ile Ser Thr Ser Asn
               100                 105                 110

Gly Ser Leu Glu Gly Leu Asp Asn Gln Glu Gly Gly Val Cys Gln Thr
           115                 120                 125

Arg Ala Met Lys Ile Leu Met Lys Val Gly
       130                 135

<210> SEQ ID NO 24
<211> LENGTH: 30
<212> TYPE: PRT
<213> ORGANISM: Homo sapiens

<400> SEQUENCE: 24

Val Lys Phe Thr Ile Lys Phe Gln Glu Phe Ser Pro Asn Leu Trp Gly
 1               5                  10                  15

Leu Glu Phe Gln Lys Asn Lys Asp Tyr Tyr Ile Ile Ser Thr
                20                  25                  30

<210> SEQ ID NO 25
<211> LENGTH: 21
<212> TYPE: PRT
<213> ORGANISM: Pseudomonas aeruginosa

<400> SEQUENCE: 25

Asp Ser Val Thr Phe Asp Val Ser Lys Leu Lys Glu Gly Glu Gln Tyr
 1               5                  10                  15

Met Phe Phe Cys Thr
                20

<210> SEQ ID NO 26
<211> LENGTH: 18
<212> TYPE: PRT
<213> ORGANISM: Thiobacillus ferrooxidans
```

```
<400> SEQUENCE: 26

Tyr Thr Asn Phe Thr Trp His Pro Thr Ala Gly Thr Tyr Tyr Tyr Val
1               5                   10                  15

Cys Gln

<210> SEQ ID NO 27
<211> LENGTH: 19
<212> TYPE: PRT
<213> ORGANISM: Chloroflexus aurantiacus

<400> SEQUENCE: 27

Ser Gly Ser Val Thr Phe Arg Thr Pro Ala Pro Gly Thr Tyr Leu Tyr
1               5                   10                  15

Ile Cys Thr

<210> SEQ ID NO 28
<211> LENGTH: 18
<212> TYPE: PRT
<213> ORGANISM: Ulva pertusa

<400> SEQUENCE: 28

Glu Thr Val Val Arg Lys Leu Ser Thr Pro Gly Val Tyr Gly Val Tyr
1               5                   10                  15

Cys Glu

<210> SEQ ID NO 29
<211> LENGTH: 17
<212> TYPE: PRT
<213> ORGANISM: Cucumis sativus

<400> SEQUENCE: 29

Gly Arg Asp Gln Ile Lys Leu Pro Lys Gly Gln Ser Tyr Phe Ile Cys
1               5                   10                  15

Asn

<210> SEQ ID NO 30
<211> LENGTH: 18
<212> TYPE: PRT
<213> ORGANISM: Cucumis sativus

<400> SEQUENCE: 30

Ser Pro Val Ile Glu Arg Leu Asp Glu Leu Gly Met His Tyr Phe Val
1               5                   10                  15

Cys Thr

<210> SEQ ID NO 31
<211> LENGTH: 70
<212> TYPE: PRT
<213> ORGANISM: Homo sapiens

<400> SEQUENCE: 31

Thr Pro Leu Leu Asn Cys Ala Arg Pro Asp Gln Asp Val Lys Phe Thr
1               5                   10                  15

Ile Lys Phe Gln Glu Phe Ser Pro Asn Leu Trp Gly Leu Glu Phe Gln
                20                  25                  30

Lys Asn Lys Asp Tyr Tyr Ile Ser Thr Ser Asn Gly Ser Leu Glu
            35                  40                  45

Gly Leu Asp Asn Gln Glu Gly Gly Val Cys Gln Thr Arg Ala Met Lys
    50                  55                  60
```

```
Ile Leu Met Lys Val Gly
65                  70

<210> SEQ ID NO 32
<211> LENGTH: 42
<212> TYPE: PRT
<213> ORGANISM: Ulva pertusa

<400> SEQUENCE: 32

Ser Tyr Asp Asp Tyr Leu Asn Ser Lys Gly Glu Thr Val Val Arg Lys
1               5                   10                  15

Leu Ser Thr Pro Gly Val Tyr Gly Val Tyr Cys Glu Pro His Ala Gly
            20                  25                  30

Ala Gly Met Lys Met Thr Ile Thr Val Gln
        35                  40

<210> SEQ ID NO 33
<211> LENGTH: 71
<212> TYPE: PRT
<213> ORGANISM: Homo sapiens

<400> SEQUENCE: 33

Asn Thr Pro Leu Leu Asn Cys Ala Arg Pro Asp Gln Asp Val Lys Phe
1               5                   10                  15

Thr Ile Lys Phe Gln Glu Phe Ser Pro Asn Leu Trp Gly Leu Glu Phe
            20                  25                  30

Gln Lys Asn Lys Asp Tyr Tyr Ile Ile Ser Thr Ser Asn Gly Ser Leu
        35                  40                  45

Glu Gly Leu Asp Asn Gln Glu Gly Gly Val Cys Gln Thr Arg Ala Met
    50                  55                  60

Lys Ile Leu Met Lys Val Gly
65                  70

<210> SEQ ID NO 34
<211> LENGTH: 53
<212> TYPE: PRT
<213> ORGANISM: Pseudomonas aeruginosa

<400> SEQUENCE: 34

Asp Asp Ser Arg Val Ile Ala His Thr Lys Leu Ile Gly Ser Gly Glu
1               5                   10                  15

Lys Asp Ser Val Thr Phe Asp Val Ser Lys Leu Lys Glu Gly Glu Gln
            20                  25                  30

Tyr Met Phe Phe Cys Thr Phe Pro Gly His Ser Ala Leu Met Lys Gly
        35                  40                  45

Thr Leu Thr Leu Lys
    50
```

COMPOSITIONS AND METHODS FOR TREATING CONDITIONS RELATED TO EPHRIN SIGNALING WITH CUPREDOXINS

RELATED APPLICATIONS

This application claims priority under 35 U.S.C. §§ 119 and 120 to U.S. Provisional Patent Application Ser. No. 60/764,749, filed Feb. 3, 2006, U.S. Provisional Patent Application Ser. No. 60/682,812, filed May 20, 2005, and U.S. patent application Ser. No. 11/244,105, filed Oct. 6, 2005, which claims priority to U.S. Provisional Patent Application Ser. No. 60/616,782, filed Oct. 7, 2004, and U.S. Provisional Patent Application Ser. No. 60/680,500, filed May 13, 2005, and is a continuation-in-part of U.S. patent application Ser. No. 10/720,603, filed Nov. 24, 2003, which claims priority to U.S. Provisional Patent Application Ser. No. 60/414,550, filed Aug. 15, 2003, and which is a continuation-in-part of U.S. patent application Ser. No. 10/047,710, filed Jan. 15, 2002, issued Jul. 12, 2006 as U.S. Pat. No. 7,084,105, which claims priority to U.S. Provisional Patent Application Ser. No. 60/269,133, filed Feb. 15, 2001. The entire content of these prior applications is fully incorporated herein by reference.

STATEMENT OF GOVERNMENTAL INTEREST

The subject matter of this application has been supported by research grants from the National Institutes of Health (NIH), Bethesda, Md., U.S.A., (Grant Numbers A1 16790-21, ES 04050-16, A1 45541, CA09432 and N01-CM97567). The government may have certain rights in this invention.

FIELD OF THE INVENTION

The present invention relates to cupredoxins and their use in modulating cellular functions involving ephrins and ephrin receptors. The invention also relates to methods of treating ephrin-related conditions. More particularly, the invention relates to the use of a substantially pure cupredoxin in methods of slowing growth and metastasis of cancer cells and pathological conditions, and specifically those related to ephrin/ephrin receptor signaling, as well as other therapeutic methods related to ephrin/ephrin receptor signaling. The invention also relates to variants, derivatives and structural equivalents of cupredoxins that retain the ability to interfere with the ephrin signaling system in cells.

BACKGROUND

The ephrin receptors (Eph receptors) are a large family of receptor tyrosine kinases that regulate a multitude of processes in developing and adult tissues by binding a family of ligands called ephrins. Eph receptors are divided into either the A- or B-type with ephrin ligands. There are currently nine known members of the A-type, EphA1-8 and EphA10, and four known members of the B-type, EphB1-4 and EphB6. In general, the A class receptors preferentially bind A-type ligands, while the B class receptors preferentially bind the B-type ligands. The Eph receptors are like other receptor tyrosine kinases, with a single transmembrane spanning domain, with a glycosylated extracellular region comprised of a ligand-binding domain with immunoglobulin-like motifs, a cysteine rich region and two fibronectin type III repeats. (Surawska et al., Cytokine & Growth Factor Reviews 15:419-433 (2004)). The ephrin ligands are divided into the A and B class depending on their sequence conservation. EphrinA ligands are glycosylphosphatidylinisotol anchored and usually bound by Eph-A type receptors, while ephrinB ligands contain a transmembrane domain and a short cytoplasmic region and are usually bound by EphB-type receptors. Id.

The signaling process begins when Eph receptor dimerizes with an ephrin ligand, causing the receptor to become phosphorylated. Aggregates of ephrin-EphReceptor complexes are formed by higher-order clustering. Receptor activation is thought to depend on the degree of multimerization, but is not limited to the tetrameric form as receptor phosphorylation is observed in both lower- and higher-order forms. Depending on the state of multimerization, distinct Eph receptor complexes can induce biological effects. In addition to the "forward" signaling through the Eph receptor into the receptor-expressing cell, there is also "backwards" signaling through the ephrin into the ephrin-expressing cell. For example, the cytoplasmic tail on the B-ephrins can become phosphorylated leading to the recruitment of signaling effectors and a signal transduction cascade within the ephrin-signaling cell. Id.

Ephrins are now known to have roles in many cell-cell interactions, including axon pathfinding, neuronal cell migration, and interactions in vascular endothelial cells and specialized epithelia. (Flanagan & Vanderhaeghen, Annu. Rev. Neurosci. 21:309-345 (1998); Frisen et al., EMBO J. 18:5159-5165 (1999)). Eph receptors have also been implicated in a variety of pathological processes, including tumor progression, pathological forms of angiogenesis, chronic pain following tissue damage, inhibition of nerve regeneration after spinal cord injury, and human congenital malformations. (Koolpe et al., J Biol. Chem. 280:17301-17311 (2005)). Eph receptors are also reported to play a role in the balance of stem cell self-renewal versus cell-fate determination and differentiation. Id.

Eph receptor and ephrin over-expression can result in tumorigenesis, and are associated with angiogenesis and metastasis in many types of human cancer, including lung, breast and prostate cancer, as well as melanoma and leukemia. (Surawska et al., Cytokine & Growth Factor Reviews 15:419-433 (2004)). Over-expression of the Eph receptor is thought not to affect the proliferation of cells, but changes their invasive behavior. According to one theory, in malignant cells with high levels of EphA2, the receptors are mislocalized, not able to bind their ephrin ligands, and therefore not phosphorylated, resulting in increased extracellular matrix adhesions and higher metastatic potential. (Ruoslahti, Adv. Cancer Res. 76:1-20 (1999)). Angiogenesis is the formation of new blood vessels and capillaries from pre-existing vasculature and is an essential process for tumor survival and growth. Evidence exists that implicates Eph receptor/ephrin up-regulation during blood vessel invasion of tumors. (Surawska et al., (2004).) A-type ephrins in particular are associated with tumor angiogenesis, and EphA2-Fc and EphA3-Fc fusion proteins decreased tumor vascular density, tumor volume and cell proliferation, and also increased apoptosis. (Brantley et al., Oncogene 21:7011-7026 (2002)).

The crystal structure of the EphB2 receptor-ephrinB2 complex indicates that the ectodomain of the ephrinB2 folding topology is an eight-stranded barrel that is a variation on the common Greek key P-barrel fold, and shares considerable homology with the cupredoxin family of copper-binding proteins, although ephrinB2 does not bind copper. The main difference between ephrin and the cupredoxin-fold proteins is the unusual length of the ephrin $G-H_L$ and $C-D_L$ loops with are part of the dimerization and tetramerization ligand receptor interfaces, respectively. Crystallization studies further indicate that the G-H$_L$ loop is involved in receptor binding. (Himanen et al., Nature 414:933-938 (2001)). The extracellular domain of mouse ephrinB2 also has a topological similarity to plant nodulins and phytocyanins. (Toth et al., Developmental Cell, 1:83-92 (2001)).

Reports on regression of cancer in humans and animals infected with microbial pathogens date back more than 100 years, originating with the initial report by Coley. (Clin. Orthop. Relat. Res. 262:3-12 (1891)). Several subsequent reports have shown that microbial pathogens replicate at tumor sites under hypoxic conditions and also stimulate the host's immune system during infection, leading to an inhibition of cancer progression. (Alexandrof et al., Lancet 353:1689-1694 (1999); Paglia & Guzman, Cancer Immunol. Immunother. 46:88-92 (1998); Pawelek et al., Cancer Res. 57:4537-4544 (1997)). Bacterial pathogens such as *Pseudomonas aeruginosa* and many others produce a range of virulence factors that allow the bacteria to escape host defense and cause disease. (Tang et al., Infect. Immun. 64:37-43 (1996); Clark and Bavoil, Methods in Enzymology, vol. 235, Bacterial Pathogenesis, Academic Press, Inc. San Diego Calif. (1994); Salyers and Whitt, Bacterial Pathogenesis: A Molecular Approach, ASM Press, Washington D.C. (1994)). Some virulence factors induce apoptosis in phagocytic cells such as macrophages to subvert host defense. (Monack et al., Proc. Natl. Acad. Sci. USA 94:10385-10390 (1997); Zychlinsky and Sansonetti, J. Clin. Investig. 100:493-495 (1997)).

Two redox proteins elaborated by *P. aeruginosa*, the cupredoxin azurin and cytochrome $c_{551}$ (Cyt $c_{551}$), both enter J774 cells and show significant cytotoxic activity towards the human cancer cells as compared to normal cells. (Zaborina et al., Microbiology 146: 2521-2530 (2000)). Azurin can also enter human melanoma UISO-Mel-2 or human breast cancer MCF-7 cells. (Yamada et al., PNAS 99:14098-14103 (2002); Punj et al., Oncogene 23:2367-2378 (2004); Yamada et al., Cell. Biol. 7:14181431 (2005)). In addition, azurin from *P. aeruginosa* preferentially enters J774 murine reticulum cell sarcoma cells, forms a complex with and stabilizes the tumor suppressor protein p53, enhances the intracellular concentration of p53, and induces apoptosis. (Yamada et al., Infection and Immunity, 70:7054-7062 (2002)). Azurin also caused a significant increase of apoptosis in human osteosarcoma cells as compared to non-cancerous cells. (Ye et al., Ai Zheng 24:298-304 (2003)).

Cytochrome $C_{551}$ (Cyt $C_{551}$) from *P. aeruginosa* enhances the level of tumor suppressor protein p16$^{Ink4a}$ and inhibits cell cycle progression in J774 cells. (Hiraoka et al., PNAS 101:6427-6432 (2004)). However, when colon cancer cells, such as HCT 116 cells, or p53-null lung cancer H1299 cells were grown in presence of wild type azurin or wild type cytochrome $c_{551}$ for 3 days, they inhibited the growth of HCT 116 cells at a much lower concentration (IC50=17 μg/ml for azurin; 12 μg/ml for Cyt C) than H1299 cells (>20 μg/ml). Id.

A cancer is a malignant tumor of potentially unlimited growth. It is primarily the pathogenic replication (a loss of normal regulatory control) of various types of cells found in the human body. Initial treatment of the disease is often surgery, radiation treatment or the combination of these treatments, but locally recurrent and metastatic disease is frequent. Chemotherapeutic treatments for some cancers are available but these seldom induce long term regression. Hence, they are often not curative. Commonly, tumors and their metastases become refractory to chemotherapy, in an event known as the development of multidrug resistance. In many cases, tumors are inherently resistant to some classes of chemotherapeutic agents. In addition, such treatments threaten noncancerous cells, are stressful to the human body, and produce many side effects. Improved agents are therefore needed to prevent the spread of cancer cells.

SUMMARY OF THE INVENTION

The present invention relates to compositions and methods of use of cupredoxins, and variants, derivatives and structural equivalents of cupredoxins that interfere with the ephrin signaling system in mammalian cells. Specifically, the invention relates to compositions and methods that use cupredoxins, such as azurin and plastocyanin, and variants, derivatives and structural equivalents thereof, to treat cancer in mammals.

One aspect of the invention relates to an isolated peptide that is a variant, derivative or structural equivalent of a cupredoxin, and that can inhibit the growth of cancer in mammalian cells or tissues. This peptide may be an azurin, plastocyanin, pseudoazurin, plastocyanin, rusticyanin or auracyanin, and specifically an azurin, plastocyanin and rusticyanin. In some embodiments, the cupredoxin is from *Pseudomonas aeruginosa, Thiobacillus ferrooxidans, Phormidium laminosum, Alcaligenes faecalis, Achromobacter xylosoxidan, Bordetella bronchiseptica, Methylomonas* sp., *Neisseria meningitidis, Neisseria gonorrhoeae, Pseudomonas fluorescens, Pseudomonas chlororaphis, Xylella fastidiosa, Cucumis sativus, Chloroflexus aurantiacus, Vibrio parahaemolyticus* or *Ulva pertusa*, and specifically *Pseudomonas aeruginosa, Thiobacillus ferrooxidans, Phormidium laminosum* or *Ulva pertusa*. The isolated peptide may be part SEQ ID NOS: 1-17 and 22-23. Additionally, SEQ ID NOS: 1-17 and 22-23 may have at least about 90% amino acid sequence identity to the peptide.

In some embodiments, the isolated peptide may be a truncation of a cupredoxin. In specific embodiments, the peptide is more than about 10 residues and not more than about 100 residues. The peptide may comprise or, alternatively, consist of *P. aeruginosa* azurin residues 96-113, *P. aeruginosa* azurin residues 88-113, *Ulva pertusa* plastocyanin residues 70-84, *Ulva pertusa* residues 57-98, or SEQ ID NOS: 22-30. In some embodiments, the isolated peptide comprises equivalent residues of a subject cupredoxin as a region of an object cupredoxin selected from the group consisting of *P. aeruginosa* azurin residues 96-113, *P. aeruginosa* azurin residues 88-113, *Ulva pertusa* plastocyanin residues 70-84, *Ulva pertusa* residues 57-98, or SEQ ID NOS: 22-30.

Another aspect of the invention is a composition comprising at least one cupredoxin, or variant, derivative or structural equivalent of a cupredoxin that can inhibit the growth of cancer in mammalian cells or tissues in a pharmaceutical composition. In some embodiments, the pharmaceutical composition is formulated for intravenous administration. The cupredoxin may be from *Pseudomonas aeruginosa, Thiobacillus ferrooxidans, Phormidium laminosum, Alcaligenes faecalis, Achromobacter xylosoxidan, Bordetella bronchiseptica, Methylomonas* sp., *Neisseria meningitidis, Neisseria gonorrhoeae, Pseudomonas fluorescens, Pseudomonas chlororaphis, Xylella fastidiosa, Cucumis sativus, Chloroflexus aurantiacus, Vibrio parahaemolyticus* or *Ulva pertusa*, and specifically *Pseudomonas aeruginosa, Thiobacillus ferrooxidans, Phormidium laminosum and Ulva pertusa. In some embodiments, the cupredoxin may be SEQ ID NOS: 1-17 and 22-23.

Another aspect of the invention is a method to treat a mammalian patient suffering a pathological condition related to the ephrin signaling system or suffering from cancer, comprising administering to the patient a therapeutically effective amount of a composition comprising at least one cupredoxin, or variant, derivative or structural equivalent of a cupredoxin in a pharmaceutical composition. In some embodiments, the patient is suffering from interstitial cystitis (IC), lesions associated with inflammatory bowel disease (IBD), HIV infection, cardiovascular disease, central nervous system disorders, peripheral vascular diseases, viral diseases, degeneration of the central nervous system (Christopher Reeve's disease) or Alzheimer's disease. In other embodiments, the patient is suffering from a cancer, such as breast cancer, liver cancer, gastrointestinal cancer, neuroblastoma, neural cancer, leukemia, lymphoma, prostrate cancer, pancreatic cancer, lung cancer, melanoma, ovarian cancer, endometrial tumor, choriocarcinoma, teratocarcinoma, thyroid cancer, all sarcomas including those arising from soft tissues and bone, renal carcinomas, epidermoid cancer or non-small cell lung cancer. In some embodiments, the patient is a human.

Another aspect of the invention is a composition comprising at least two isolated polypeptides that are a cupredoxin, or a variant, derivative or structural equivalent of a cupredoxin can inhibit the growth of cancer in mammalian cells or tissues. In some embodiments, the composition is in a pharmaceutical composition.

Another aspect of the invention is a kit comprising a composition with at least one cupredoxin, or variant, derivative or structural equivalent of a cupredoxin in a pharmaceutical composition in a vial. The kit may be designed for intravenous administration.

Another aspect of the invention is a method, comprising contacting the mammalian cancer cells with a cupredoxin, or variant, derivative or structural equivalent thereof; and measuring the growth of the cancer cells. The cancer cells may be breast cancer, liver cancer, gastrointestinal cancer, neuroblastoma, neural cancer, leukemia, lymphoma, prostrate cancer, pancreatic cancer, lung cancer, melanoma, ovarian cancer, endometrial tumor, choriocarcinoma, teratocarcinoma, thyroid cancer, all sarcomas including those arising from soft tissues and bone, renal carcinomas, epidermoid cancer or non-small cell lung cancer. In some embodiments, the cancer cells are in vivo.

Another aspect of the invention is an expression vector which encodes a variant, derivative or structural equivalent of a cupredoxin which can inhibit the growth of cancer in mammalian cells or tissues.

Another aspect of the invention is an isolated peptide that is a variant, derivative or structural equivalent of a cupredoxin; and that can bind an ephrin receptor, such as EphA1, EphA2, EphA3, EphA4, EphA5, EphA6, EphA7, EphA8, EphA10, EphB1, EphB2, EphB3, EphB4 and EphB6. In some embodiments, the peptide also binds an ephrin, such as ephrinA1, ephrinA2, ephrinA3, ephrinA4, ephrinA5, ephrinB1, ephrinB2, ephrinB3 and ephrinB4. In other embodiments, the isolated peptide binds an ephrin and its receptor, and specifically Ephrin2B and Eph2B. In a related aspect, an isolated peptide is a variant, derivative or structural equivalent of a cupredoxin; and that can bind an ephrin, such as ephrinA1, ephrinA2, ephrinA3, ephrinA4, ephrinA5, ephrinB1, ephrinB2, ephrinB3 and ephrinB4.

Another aspect of the invention is a method comprising administering a pharmaceutical composition containing at least one cupredoxin, or peptide of the invention to a mammalian patient to guide the growth of blood vessels in the patient.

Another aspect of the invention is a method comprising administering a pharmaceutical composition containing at least one cupredoxin, or peptide of the invention to a mammalian patient to decrease the growth of blood vessels in the patient.

Another aspect of the invention is a method comprising administering a pharmaceutical composition containing at least one cupredoxin, or peptide of the invention to a mammalian patient to guide to growth of neurons in the patient.

Another aspect of the invention is a method comprising administering a pharmaceutical composition containing at least one cupredoxin, or peptide of the invention to a mammalian patient to promote osteogenesis in the patient.

Another aspect of the invention is a method comprising substituting an effective amount of a pharmaceutical composition containing at least one cupredoxin, or peptide of the invention to a mammalian patient for an ephrin in a therapeutic method requiring the use of the ephrin.

Another aspect of the invention is a method comprising administering a pharmaceutical composition containing at least one cupredoxin, or peptide of the invention to a mammalian cell to inhibit the activity of an ephrin receptor associated with the cell.

Another aspect of the invention is a method comprising administering a pharmaceutical composition containing at least one cupredoxin, or peptide of the invention to increase the activity of an ephrin receptor associated with the cell.

Another aspect of the invention is a method comprising administering to a human patient having a tissue expressing an ephrin receptor, a pharmaceutical composition containing at least one cupredoxin, or peptide of the invention which comprises a derivative of cupredoxin, or a variant, derivative or structural equivalent fused to a pharmaceutical agent. In some embodiments, the tissues expressing an ephrin receptor is cancer.

Another aspect of the invention is a method to detect tissues with ephrin receptors which has the steps of administering to a human patient a pharmaceutical composition containing at least one cupredoxin, or peptide of the invention fused to a detectable probe and detecting the distribution of the probe within the patient.

These and other aspects, advantages, and features of the invention will become apparent from the following figures and detailed description of the specific embodiments.

BRIEF DESCRIPTION OF THE SEQUENCES

SEQ ID NO: 1. Amino acid sequence of azurin from *Pseudomonas aeruginosa*.

SEQ ID NO: 2. Amino acid sequence of plastocyanin from *Phormidium laminosum*.

SEQ ID NO: 3. Amino acid sequence of rusticyanin from *Thiobacillus ferrooxidans*.

SEQ ID NO: 4. Amino acid sequence of pseudoazurin from *Achromobacter cycloclastes*.

SEQ ID NO: 5. Amino acid sequence of azurin from *Alcaligenes faecalis*.

SEQ ID NO: 6. Amino acid sequence of azurin from *Achromobacter xylosoxidans* ssp. *denitrificans* I.

SEQ ID NO: 7. Amino acid sequence of azurin from *Bordetella bronchiseptica*.

SEQ ID NO: 8. Amino acid sequence of azurin from *Methylomonas* sp. J.

SEQ ID NO: 9. Amino acid sequence of azurin from *Neisseria meningitidis* Z2491.

SEQ ID NO: 10. Amino acid sequence of azurin from *Neisseria gonorrhoeae*.

SEQ ID NO: 11. Amino acid sequence of azurin from *Pseudomonas fluorescens*.

SEQ ID NO: 12. Amino acid sequence of azurin from *Pseudomonas chlororaphis*.

SEQ ID NO: 13. Amino acid sequence of azurin from *Xylella fastidiosa* 9a5c.

SEQ ID NO: 14. Amino acid sequence of stellacyanin from *Cucumis sativus*.

SEQ ID NO: 15. Amino acid sequence of auracyanin A from *Chloroflexus aurantiacus*.

SEQ ID NO: 16. Amino acid sequence of auracyanin B from *Chloroflexus aurantiacus*.

SEQ ID NO: 17. Amino acid sequence of cucumber basic protein from *Cucumis sativus*.

SEQ ID NO: 18. Amino acid sequence of 18-mer azurin peptide, *Pseudomonas aeruginosa* azurin from residues 96-113.

SEQ ID NO: 19. Amino acid sequence of *Pseudomonas aeruginosa* azurin from residues 88-113.

SEQ ID NO: 20. Amino acid sequence of *Ulva pertusa* plastocyanin from residues 70-84.

SEQ ID NO: 21. Amino acid sequence of *Vibrio parahaemolyticus* azurin.

SEQ ID NO: 22. Amino acid sequence of *Ulva pertusa* plastocyanin.

SEQ ID NO: 23. Amino acid sequence of EphrinB2 ectodomain from human.

SEQ ID NO: 24. Amino acid sequence of G-H loop region of human EphrinB2.

SEQ ID NO: 25. Amino acid sequence of the *P. aeruginosa* azurin region structurally analogous to the EphrinB2 G-H loop region.

SEQ ID NO: 26. Amino acid sequence of the *Thiobacillus (Acidithiobacillus) ferrooxidans* rusticyanin region structurally analogous to the EphrinB2 G-H loop region.

SEQ ID NO: 27. Amino acid sequence of the *Chloroflexus aurantiacus* auracyanin B region structurally analogous to the EphrinB2 G-H loop region.

SEQ ID NO: 28. Amino acid sequence of the *Ulva pertusa* plastocyanin region structurally analogous to the EphrinB2 G-H loop region.

SEQ ID NO: 29. Amino acid sequence of the *Cucumis sativus* cucumber basic protein region structurally analogous to the EphrinB2 G-H loop region.

SEQ ID NO: 30. Amino acid sequence of the *Cucumis sativus* stellacyanin region structurally analogous to the EphrinB2 G-H loop region.

SEQ ID NO: 31. Amino acid sequence of human EphrinB2 residues 69-138.

SEQ ID NO: 32. Amino acid sequence of *Ulva pertusa* plastocyanin residues 57-98.

SEQ ID NO: 33. Amino acid sequence of human EphrinB2 residues 68-138.

SEQ ID NO: 34. Amino acid sequence of *P. aeruginosa* azurin residues 76-128.

BRIEF DESCRIPTION OF THE FIGURES

FIG. 1 depicts a structural alignment of azurin with ephrinB2. The G-H loop of ephrin B-2 (region that mediates high-affinity interaction with the EphB receptors) is indicated by boxes. 1JZG_A is the amino acid sequence of azurin from *Pseudomonas aeruginosa* (SEQ ID NO: 1). 1KGY_E is the amino acid sequence of ephrinB2 ectodomain from human (SEQ ID NO: 23).

FIG. 2 depicts a structural alignment of cupredoxins with ephrinB2. The box indicates the G-H loop of ephrinB2 (15 aa), involved in Eph receptor binding. Conserved residues are indicated in bold and underlined. Capital letters are super-positions. Dashes are where there are no alignments. The EphrinB2 G-H loop region is SEQ ID NO: 24. The *P. aeruginosa* azurin region structurally analogous to the EphrinB2 G-H loop region is SEQ ID NO: 25. The *Thiobacillus (Acidithiobacillus) ferrooxidans* rusticyanin region structurally analogous to the EphrinB2 G-H loop region is SEQ ID NO: 26. The *Chloroflexus aurantiacus* auracyanin region structurally analogous to the EphrinB2 G-H loop region is SEQ ID NO: 27. The *Phormidium laminosum* plastocyanin region structurally analogous to the EphrinB2 G-H loop region is SEQ ID NO: 28. The *Cucumis sativus* cucumber basic protein region structurally analogous to the EphrinB2 G-H loop region is SEQ ID NO: 29. The *Cucumis sativus* stellacyanin region structurally analogous to the EphrinB2 G-H loop region is SEQ ID NO: 30.

In FIG. 3A, the topology of each protein is shown using TOPS cartoons. TOPS cartoons represent the structure as a sequence of secondary structure elements (SSEs): β-strands (depicted as triangles) and helices (alpha and 310) (depicted as circles), how they are connected in a sequence from amino to carboxyl terminus, and their relative spatial positions and orientations. The direction of the elements can be deduced from the connecting lines. "Up" strands are indicated by upward pointing triangles and "Down" strands by downward pointing triangles. FIG. 3B, the pictures were drawn using the MolMol program (Koradi et al., J. Mol. Graphics. 14:51-55 (1996)).

In FIG. 6A, an initial screening experiment was performed to determine relative binding strengths of azurin or GST-Azu wherein the SPR traces were recorded after injection of the cupredoxins (100 nM) onto EphB2-Fc-modified CM5 sensor chips. Notably, azurin, GST-Azu 88-113, and GST-Azu 36-128 bind stronger than the native ligand (ephrinB2-Fc) to EphB2-Fc. In FIG. 6B, binding affinity curves for the interactions of azurin, GST-Azu 88-113, ephrinB2-Fc, and GST-Azu 36-89 to immobilized EphB2-Fc after titrating increasing concentrations (0.05-100 nM) of the cupredoxins. Equilibrium resonance signals (Req) were extrapolated from the individual sensorgrams to construct the curves. Binding dissociation constants (Kd) were calculated (Table 6) after fitting the data to a Langmuir (1:1) binding model using the equation Req=Rmax/(1+Kd/C) and the curve fits are shown connecting the data points in the titration curves. The quantitative data sets agree with those from the initial binding screen.

In FIG. 7A, SPR binding curves for the interactions of azurin and GST-Azu with ephrinB2-Fc for which binding affinities (Kd) were determined as previously described. In FIG. 7B, SPR binding competition studies with EphB2-Fc immobilized on CM5 sensor chips.

(In FIG. 9A, effect of azurin (Azu 96-113) and plastocyanin (Plc 70-84) synthetic peptides on cell viability of Astrocytoma CCF-STTG1 and Glioblastoma LN-229 cancer cell lines. In FIG. 9B, effect of different concentrations of plastocyanin (Plc 70-84) synthetic peptide on Melanoma UISO-Mel-2 cell viability. Cell viability was determined by MTT assay as described in Example 10. Cancer cells ($2 \times 10^4$ cells per well in 96-well plates) were treated with the synthetic peptides at different concentrations for 24 h at 37° C. Data are presented as the percentage of cell viability as compared to that of untreated control (100% viability) In FIG. 9C, cytotoxic activity of Azu 96-113 synthetic peptide towards Glioblastoma LN-229 cells. Cytotoxicity effects were determined by MTT assay. Cancer ($2 \times 10^4$ cells per well in 96-well plates) were treated with various concentrations of Azu 96-113 (10, 25, 50, 75, 100 µM) for 24 h at 37° C. Percent cytotoxicity is expressed as percentage of cell death as compared to that of untreated control (0% cytotoxicity).

DETAILED DESCRIPTION OF THE INVENTION

Definitions

Figure 3:
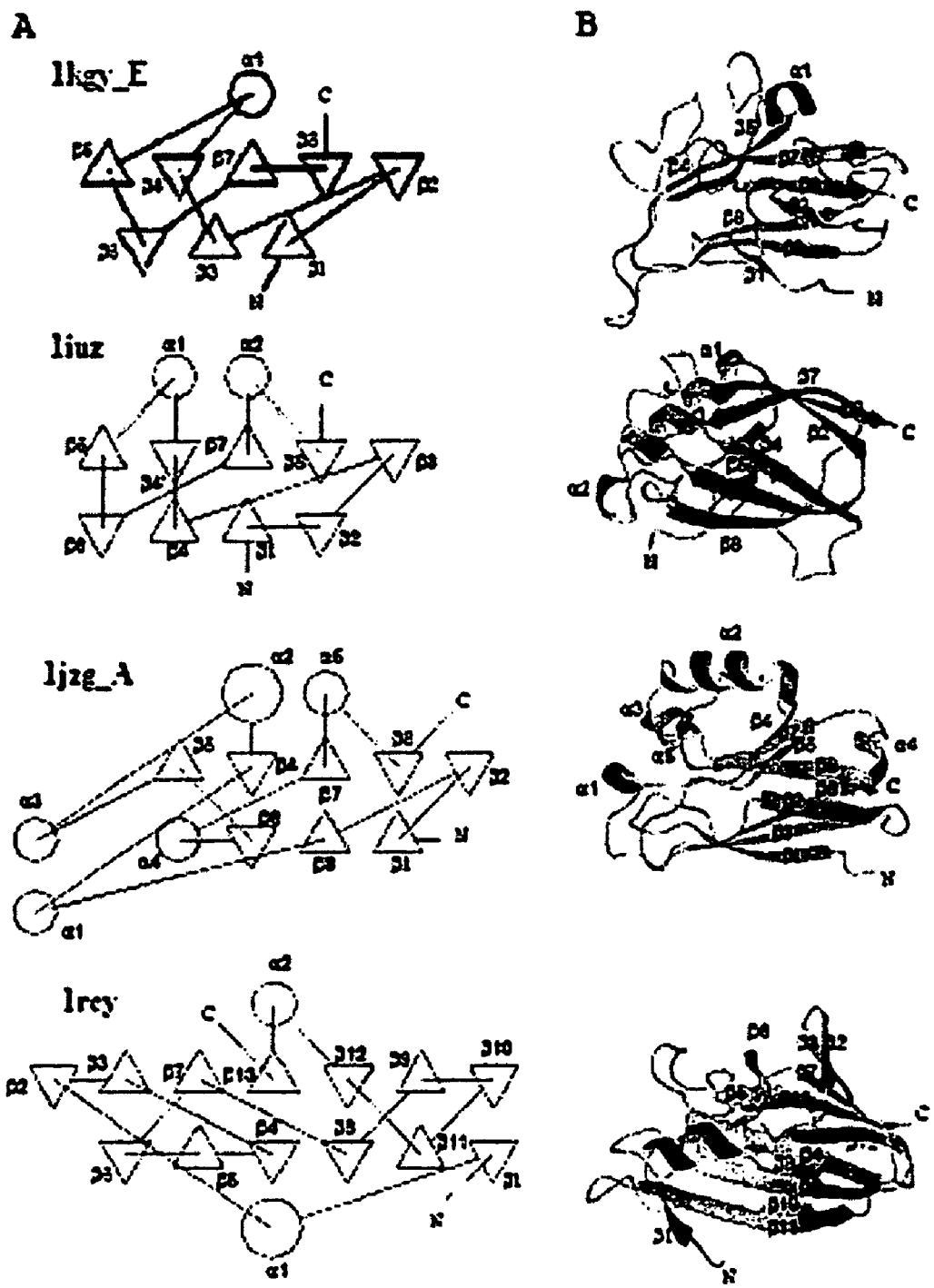
FIG. 3 depicts a comparison among the structures of the ephrinB2 ectodomain from human (1kgy_E), plastocyanin from *Ulva pertusa* (1 iuz), azurin from *Pseudomonas aeruginosa* (1jzg_A) and rusticyanin from *Thiobacillus (Acidithiobacillus) ferrooxidans* (1rcy).

As used herein, the term "cell" includes both the singular or the plural of the term, unless specifically described as a "single cell."

As used herein, the terms "polypeptide," "peptide," and "protein" are used interchangeably to refer to a polymer of amino acid residues. The terms apply to amino acid polymers in which one or more amino acid residue is an artificial chemical analogue of a corresponding naturally occurring amino acid. The terms also apply to naturally occurring amino acid polymers. The terms "polypeptide," "peptide," and "protein" are also inclusive of modifications including, but not limited to, glycosylation, lipid attachment, sulfation, gamma-carboxylation of glutamic acid residues, hydroxylation and ADP-ribosylation. It will be appreciated that polypeptides are not always entirely linear. For instance, polypeptides may be branched as a result of ubiquitination and they may be circular (with or without branching), generally as a result of post-translation events, including natural processing event and events brought about by human manipulation which do not occur naturally. Circular, branched and branched circular polypeptides may be synthesized by non-translation natural process and by entirely synthetic methods as well. Further, this invention contemplates the use of both the methionine-containing and the methionine-less amino terminal variants of the protein of the invention.

As used herein, the term "pathological condition" includes anatomic and physiological deviations from the normal that constitute an impairment of the normal state of the living animal or one of its parts, that interrupts or modifies the performance of the bodily functions, and is a response to various factors (as malnutrition, industrial hazards, or climate), to specific infective agents (as worms, parasitic protozoa, bacteria, or viruses), to inherent defects of the organism (as genetic anomalies), or to combinations of these factors.

As used herein, the term "condition" includes anatomic and physiological deviations from the normal that constitute an impairment of the normal state of the living animal or one of its parts, that interrupts or modifies the performance of the bodily functions.

As used herein, the term "inhibit cell growth" means the slowing or ceasing of cell division and/or cell expansion. This term also includes the inhibition of cell development or increases cell death.

As used herein, the term "suffering from" includes presently exhibiting the symptoms of a pathological condition, having a pathological condition even without observable symptoms, in recovery from a pathological condition, and recovered from a pathological condition.

A used herein, the term "treatment" includes preventing, lowering, stopping, or reversing the progression or severity of the condition or symptoms associated with a condition being treated. As such, the term "treatment" includes medical, therapeutic, and/or prophylactic administration, as appropriate.

A "therapeutically effective amount" is an amount effective to prevent or slow the development of, or to partially or totally alleviate the existing symptoms in a particular condition for which the subject being treated. Determination of a therapeutically effective amount is well within the capability of those skilled in the art.

As used herein, the term "deficient in expression of the p53 tumor suppressor gene" refers to a cell having a p53 tumor suppressor gene that is inactivated, mutated, lost or under produced. For example, such a deficiency may occur as a result of genetic aberrations within the p53 gene or due to epigenic reasons such as hypermethylation of C residues in the CG islands upstream of the tumor suppressor genes or interaction with viral and cellular oncogenes.

The term "substantially pure", when used to modify the term "cupredoxin", as used herein, refers to a cupredoxin, for example, a cupredoxin isolated from the growth medium or cellular contents, in a form substantially free of, or unadulterated by, other proteins and/or active inhibitory compounds. The term "substantially pure" refers to a factor in an amount of at least about 75%, by dry weight, of isolated fraction, or at least "75% substantially pure." More specifically, the term "substantially pure" refers to a compound of at least about 85%, by dry weight, active compound, or at least "85% substantially pure." Most specifically, the term "substantially pure" refers to a compound of at least about 95%, by dry weight, active compound, or at least "95% substantially pure." The substantially pure cupredoxin can be used in combination with one or more other substantially pure compounds or isolated cupredoxins.

The phrases "isolated," "purified" or "biologically pure" refer to material which is substantially or essentially free from components which normally accompany the material as it is found in its native state. Thus, isolated peptides in accordance with the invention preferably do not contain materials normally associated with the peptides in their in situ environment. An "isolated" region refers to a region that does not include the whole sequence of the polypeptide from which the region was derived. An "isolated" nucleic acid, protein, or respective fragment thereof has been substantially removed from its in vivo environment so that it may be manipulated by the skilled artisan, such as but not limited to nucleotide sequencing, restriction digestion, site-directed mutagenesis, and subcloning into expression vectors for a nucleic acid fragment as well as obtaining the protein or protein fragment in substantially pure quantities.

The term "variant" as used herein with respect to a peptide, refers to amino acid sequence variants which may have amino acids replaced, deleted, or inserted as compared to the wild-type polypeptide. Variants may be truncations of the wild-type peptide. Thus, a variant peptide may be made by manipulation of genes encoding the polypeptide. A variant may be made by altering the basic composition or characteristics of the polypeptide, but not at least some of its fundamental activities. For example, a "variant" of azurin can be a mutated azurin that retains its ability to inhibit the growth of mammalian cancer cells. In some cases, a variant peptide is synthesized with non-natural amino acids, such as ε-(3,5-dinitrobenzoyl)-Lys residues. (Ghadiri & Fernholz, J. Am. Chem. Soc., 112:9633-9635 (1990)). In some embodiments, the variant has not more than 20, 19, 18, 17 or 16 amino acids replaced, deleted or inserted compared to wild-type peptide. In some embodiments, the variant has not more than 15, 14, 13, 12 or 11 amino acids replaced, deleted or inserted compared to wild-type peptide. In some embodiments, the variant has not more than 10, 9, 8 or 7 amino acids replaced, deleted or inserted compared to wild-type peptide. In some embodiments, the variant has not more than 6 amino acids replaced, deleted or inserted compared to wild-type peptide. In some embodiments, the variant has not more than 5 or 4 amino acids replaced, deleted or inserted compared to wild-type peptide. In some embodiments, the variant has not more than 3, 2 or 1 amino acids replaced, deleted or inserted compared to wild-type peptide.

The term "amino acid," as used herein, means an amino acid moiety that comprises any naturally-occurring or non-naturally occurring or synthetic amino acid residue, i.e., any moiety comprising at least one carboxyl and at least one amino residue directly linked by one, two, three or more carbon atoms, typically one (α) carbon atom.

The term "derivative" as used herein with respect to a peptide refers to a peptide that is derived from the subject peptide. A derivation includes chemical modifications of the peptide such that the peptide still retains some of its fundamental activities. For example, a "derivative" of azurin can be a chemically modified azurin that retains its ability to inhibit the growth of mammalian cancer cells. Chemical modifications of interest include, but are not limited to, amidation, acetylation, sulfation, polyethylene glycol (PEG) modification, phosphorylation or glycosylation of the peptide. In addition, a derivative peptide maybe a fusion of a polypeptide or fragment thereof to a chemical compound, such as but not limited to, another peptide, drug molecule or other therapeutic or pharmaceutical agent or a detectable probe.

The term "percent (%) amino acid sequence identity" is defined as the percentage of amino acid residues in a polypeptide that are identical with amino acid residues in a candidate sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Often publicly available computer software such as BLAST, BLAST2, ALIGN2 or Megalign (DNASTAR) software is used to align peptide sequences. In a specific embodiment, Blastp (available from the National Center for Biotechnology Information, Bethesda Md.) is used using the default parameters of long complexity filter, expect 10, word size 3, existence 11 and extension 1.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

% amino acid sequence identity=$X/Y*100$ where
X is the number of amino acid residues scored as identical matches by the sequence alignment program's or algorithm's alignment of A and B and
Y is the total number of amino acid residues in B.

If the length of amino acid sequence A is not equal to the length of amino acid sequence B, the % amino acid sequence identity of A to B will not equal the % amino acid sequence identity of B to A. When comparing longer sequences to shorter sequences, the shorter sequence will be the "B" sequence. For example, when comparing truncated peptides to the corresponding wild-type polypeptide, the truncated peptide will be the "B" sequence.

General

Some aspects of the present invention provides compositions and methods that use cupredoxins that have structural similarity to ephrin to interfere with the ephrin signaling system in various mammalian cells and tissues, and also inhibit the growth of mammalian cancer cells. Specifically, the present invention provides for compositions and methods that use cupredoxins and variants, derivatives and structural equivalents thereof, to interfere with the ephrin signaling system, and also inhibit the growth of mammalian cancer cells in vitro and in vivo.

The inventors previously discovered that pathogenic microorganisms secrete ATP-independent cytotoxic factors, for example redox proteins such as azurin from *P. aeruginosa*, and that such factors cause J774 cell death by apoptosis, particularly in cancer cells. It was also known that azurin has a domain from about amino acid residues 50-77 that facilitates the protein to enter preferentially into cancer cells to induce cytotoxicity.

Surprisingly, the inventors have now discovered that a C-terminal domain is found in azurins and other cupredoxins that shows a structural similarity to the ephrins. See, Examples 2, 5 and 9. It is also now known that azurin and plastocyanin, and particular regions of these peptides that are structurally homologous to the ephrin G-H loop, bind competitively to ephrin receptors in a 1:1 ratio. See, Examples 6-8. *P. aeruginosa* azurin, in particular, binds to ephrin receptors EphB2 and EphA6. See, Example 6. *Phormidium laminosum* plastocyanin shows specificity for binding ephrin receptors EphA1, A3 and B2, and to a lesser extent ephrin receptors EphA2 and A6. See, Example 6. Finally, rusticyanin shows weak binding to ephrin receptors EphA8 and B1. See, Example 6. It is also now known that azurin region amino acid residues 88-113, which contains the structural homology to the ephrin G-H loop region, binds to ephrin receptor EphB2. See, Example 7. Finally, it is now known that azurin and the 88-113 region of azurin bind to ephrinB2 as well as the ephrin receptor EphB2, and can compete with ephrinB2 for its receptor, EphB2. See, Example 8.

The inventors have also discovered that cupredoxins with regions that have a structural similarity to the ephrin G-H loop regions inhibit the growth of mammalian cancer cells in vitro. In general, *Phormidium laminosum* plastocyanin, *Thiobacillus ferrooxidans* rusticyanin and *P. aeruginosa* azurin inhibit the growth in vitro of Mel-2 human melanoma cells and MCF-7 human breast cancer cells in a trypan blue assay. See, Example 4. Further, the 88-113 residue region of azurin is now known to inhibit cell growth of MCF-7 breast cancer cells. See, Example 10. Finally, an 18-mer azurin peptide and a 15-mer *Ulva pertusa* plastocyanin peptide that correspond to the region of structural similarity to the ephrinB2 G-H loop region are now known to inhibit the growth of MCF-7 human breast cancer cells, CCF-STTG1 brain tumor astrocytoma cells and LN-229 glioblastoma cells in vitro. See, Examples 3 and 9.

Surprising, cupredoxins with structural similarity to the G-H loop of ephrinB2 also affect ephrin-related development in vivo. It is now known from in vivo studies of ephrin-related development in *C. elegans*, that the cupredoxin rusticyanin interferes with tail muscle formation while cupredoxin azurin prevents embryonic development, both ephrin-related developmental processes. See, Example 1.

It is now appreciated that in addition to azurin, the cupredoxins rusticyanin and plastocyanin also share a structural homology with the G and H regions of ephrinB2. See, Examples 2 and 5. Further, it is known that the azurin and the phytocyanins stellacyanin and cucumber basic protein also share a significant structural homology with ephrins. Because of the structural conservation in the cupredoxin family of proteins in general, it is predicted that many other cupredoxins and cupredoxin-like proteins will also display a significant structural homology to ephrins. See, Example 2. It is therefore contemplated that cupredoxin family proteins in general can be used to treat the conditions related to ephrin-signaling, and cancer, using the compositions and methods of the invention. Specific cupredoxins of interest include, but are not limited to, azurin, rusticyanin, plastocyanin, stellacyanin, auracyanin, pseudoazurin and cucumber basic protein. Exemplary protein sequences are found herein as plastocyanin (SEQ ID NOS: 2 and 22), rusticyanin (SEQ ID NO: 3), pseudoazurin (SEQ ID NO: 4), stellacyanin (SEQ ID NO: 14), auracyanin (SEQ ID NOS: 15 and 16), and cucumber basic protein (SEQ ID NO: 17). As used herein, the term "cupredoxin" refers to any member of the cupredoxin family of proteins, including cupredoxin-like proteins, such as Laz from *Neisseria*.

Azurins are particularly specific, and exemplary protein sequences for these cupredoxins are found herein, but not limited to, as those isolated from *Pseudomonas aeruginosa* (SEQ ID NO: 1); *Alcaligenes faecalis* (SEQ ID NO: 5); *Achromobacter xylosoxidans* ssp. *denitrificans* I (SEQ ID NO: 6); *Bordetella bronchiseptica* (SEQ ID NO: 7); *Methylomonas* sp. J (SEQ ID NO: 8); *Neisseria meningitidis* (SEQ ID NO: 9); *Neisseria gonnorrhoeae* (SEQ ID NO: 10), *Pseudomonas fluorescens* (SEQ ID NO: 11); *Pseudomonas chlororaphis* (SEQ ID NO: 12); *Xylella fastidiosa* 9a5c (SEQ ID NO: 13) and *Vibrio parahaemolyticus* (SEQ ID NO: 21). In a most specific embodiment, the azurin is from *Pseudomonas aeruginosa*. In other specific embodiments, the cupredoxin is plastocyanin (SEQ ID NOS: 2 and 22), rusticyanin (SEQ ID NO: 3), pseudoazurin (SEQ ID NO: 4), stellacyanin (SEQ ID NO: 14), auracyanin (SEQ ID NOS: 15 and 16), and cucumber basic protein (SEQ ID NO: 17).

In some embodiments, the cupredoxins have a Greek key beta-barrel structure. The Greek key beta-barrel structure is a well known protein fold. See, for example, Zhang & Kim (*Proteins* 40:409-419 (2000)). The Greek Key topology was named after a pattern that was common on Greek pottery. It has three up-and-down beta strands connected by hairpins, which are followed by a longer connection to a fourth beta strand, which lies adjacent to the first beta strand. In a specific embodiment, the cupredoxins and variants, derivatives and structural equivalents of cupredoxins comprise at least one Greek Key beta-barrel structure. In another specific embodiment, the cupredoxins and variants, derivatives and structural equivalents of cupredoxins comprise a Greek Key structure of at least 4 beta strands. In another more specific embodiment, the cupredoxins and variants, derivatives and structural equivalents of cupredoxins comprise a Greek Key structure of at least eight beta strands. In another specific embodiment, the cupredoxin and variants, derivatives and structural equivalents of cupredoxins comprise more than one Greek Key beta-barrel structure.

Compositions of the Invention

The invention provides for peptides that are variants, derivatives or structural equivalents of cupredoxin. In some embodiments, the peptide is substantially pure. In other embodiments, the peptide is in a composition that comprises, consists of or consists essentially of the peptide. In other embodiments, the peptide is isolated. In some embodiments, the peptide is less that a full length cupredoxin, and retains some of the functional characteristics of the cupredoxin. In some embodiments, the peptide retains the ability to interfere with ephrin-signaling in mammalian cells and tissues, and/or inhibit the growth of mammalian cancer cells. In another specific embodiment, the peptide does not raise an immune response in a mammal, and more specifically a human.

The invention also provides compositions comprising at least one, at least two or at least three cupredoxin(s), or variant(s), derivative(s) or structural equivalent(s) of a cupredoxin. The invention also provides compositions comprising at least one, at least two, or at least three cupredoxin (s) or variant(s), derivative(s) or structural equivalent(s) of cupredoxin(s) in a pharmaceutical composition.

Because of the high structural homology between the cupredoxins, it is contemplated that other cupredoxins of the family will be able to interfere with ephrin signaling, and specifically inhibit the growth of cancer in mammalian cells and tissues. In some embodiments, the cupredoxin is, but is not limited to, azurin, pseudoazurin, plastocyanin, pseudoazurin, rusticyanin or auracyanin. In particularly specific embodiments, the azurin is derived from *Pseudomonas aeruginosa, Alcaligenes faecalis, Achromobacter xylosoxidans* ssp. *denitrificans* 1, *Bordetella bronchiseptica, Methylomonas* sp., *Neisseria meningitidis, Neisseria gonorrhoeae, Pseudomonas fluorescens, Pseudomonas chlororaphis, Xylella fastidiosa* 9a5 or *Vibrio parahaemolyticus*. In a very specific embodiment, the azurin is from *Pseudomonas aeruginosa*. In other specific embodiments the cupredoxin is a plastocyanin, and more specifically a plastocyanin derived from *Phormidium laminosum* or *Ulva pertusa*. In other specific embodiments, the cupredoxin in a rusticyanin, and more specifically a rusticyanin derived from *Thiobacillus ferrooxidans*. In other specific embodiments, the cupredoxin comprises an amino acid sequence that is SEQ ID NO: 1-17, 21-22.

The invention provides for amino acid sequence variants of a cupredoxin which have amino acids replaced, deleted, or inserted as compared to the wild-type polypeptide. Variants of the invention may be truncations of the wild-type polypeptide. As used herein, a "truncation" of a polypeptide is the peptide that results from the removal of at least one amino acid residue from at least one end of the polypeptide sequence. In some embodiments, the truncation peptide results from at least the removal of at least one amino acid reside, at least five amino acid residues, at least 10 amino acid residues, at least 50 amino acid residues, or about 100 amino acid residues in total from either or both ends of the polypeptide sequence. In some embodiments, the composition comprises a peptide that consists of a region of a cupredoxin that is less that the full length wild-type polypeptide. In some embodiments, the composition comprises a peptide that consists of more than about 10 residues, more than about 15 residues or more than about 20 residues of a truncated cupredoxin. In some embodiments, the composition comprises a peptide that consists of not more than about 100 residues, not more than about 50 residues, not more than about 40 residues or not more than about 30 residues of a truncated cupredoxin. In some embodiments, the variant is a peptide to which a cupredoxin, and more specifically to SEQ ID NOS: 1-17, 21-22 has at least about 90% amino acid sequence identity, at least about 95% amino acid sequence identity or at least about 99% amino acid sequence identity.

In specific embodiments, the variant of cupredoxin comprises *P. aeruginosa* azurin residues 96-113 (SEQ ID NO: 18), 88-113 (SEQ ID NO: 19) or SEQ ID NO: 25. In other embodiments, the variant of cupredoxin consists of *P. aeruginosa* azurin residues 96-113 (SEQ ID NO: 18), 88-113 (SEQ ID NO: 19) or SEQ ID NO: 25. In other specific embodiments, the variant of cupredoxin comprises *Ulva pertusa* residues 70-84 (SEQ ID NO: 20), *Ulva pertusa* residues 57-98 (SEQ ID NO: 32), or *Ulva pertusa* sequence SEQ ID NO: 28. In other specific embodiments, the variant of cupredoxin consists of *Ulva pertusa* residues 70-84 (SEQ ID NO: 20), *Ulva pertusa* residues 57-98 (SEQ ID NO: 32), or *Ulva pertusa* sequence SEQ ID NO: 28. In other specific embodiments, the variant of cupredoxin comprises *Thiobacillus ferrooxidans* rusticyanin sequence SEQ ID NO: 26, *Chloroflexus aurantiacus* auracyanin (SEQ ID NO: 27), *Cucumis sativus* sequences SEQ ID NOS: 29 and 30. In other specific embodiments, the variant of cupredoxin consists of *Thiobacillus ferrooxidans* rusticyanin sequence SEQ ID NO: 26, *Chloroflexus aurantiacus* auracyanin (SEQ ID NO: 27), *Cucumis sativus* sequences SEQ ID NOS: 29 and 30. In other specific embodiments, the variant consists of the equivalent residues to the above truncated sequences from another cupredoxin. It is also contemplated that other cupredoxin variants can be designed that have a similar activity to any of the aforementioned variants. To do this, the subject cupredoxin amino acid sequence will be aligned to the object cupredoxin sequence, such as those that contain the truncated variants above, using BLAST, BLAST2, ALIGN2 or Megalign (DNASTAR), the relevant residues of the truncated variant located on the object cupredoxin sequence, and the equivalent residues found on the subject cupredoxin sequence, and the equivalent truncated variant thus designed.

The variants also include peptides made with synthetic amino acids not naturally occurring. For example, non-naturally occurring amino acids may be integrated into the variant peptide to extend or optimize the half-life of the composition in the bloodstream. Such variants include, but are not limited to, D,L-peptides (diastereomer), (Futaki et al., J. Biol. Chem. 276(8):5836-40 (2001); Papo et al., Cancer Res. 64(16):5779-86 (2004); Miller et al, Biochem. Pharmacol. 36(1):169-76, (1987)); peptides containing unusual amino acids (Lee et al., J. Pept. Res. 63(2):69-84 (2004)), and olefin-containing non-natural amino acid followed by hydrocarbon stapling (Schafmeister et al., J. Am. Chem. Soc. 122:5891-5892 (2000); Walenski et al., Science 305:1466-1470 (2004)). and peptides comprising ε-(3,5-dinitrobenzoyl)-Lys residues.

In other embodiments, the peptide of the invention is a derivative of a cupredoxin. The derivatives of cupredoxin are chemical modifications of the peptide such that the peptide still retains some of its fundamental activities. For example, a "derivative" of azurin can be a chemically modified azurin that retains its ability to interfere with ephrin-signaling, and specifically inhibit the growth of cancer in mammalian cells and tissues. Chemical modifications of interest include, but are not limited to, amidation, acetylation, sulfation, polyethylene glycol (PEG) modification, phosphorylation and glycosylation of the peptide. In addition, a derivative peptide maybe a fusion of a cupredoxin, or variant, derivative or structural equivalent thereof to a chemical compound, such as but not limited to, another peptide, drug molecule or other therapeutic or pharmaceutical agent or a detectable probe. Derivatives of interest include chemical modifications by which the half-life in the bloodstream of the peptides and compositions of the invention can be extended or optimized, such as by several methods well known to those in the art, including but not limited to, circularized peptides (Monk et al., BioDrugs 19(4):261-78, (2005); DeFreest et al., J. Pept. Res. 63(5): 409-19 (2004)), N- and C-terminal modifications (Labrie et al., Clin. Invest. Med. 13(5):275-8, (1990)), and olefin-containing non-natural amino acid followed by hydrocarbon stapling (Schafineister et al., J. Am. Chem. Soc. 122:5891-5892 (2000); Walenski et al., Science 305:1466-1470 (2004)).

It is contemplated that the peptides invention may be a variant, derivative and/or structural equivalent of a cupredoxin. For example, the peptides may be a truncation of azurin that has been PEGylated, thus making it both a variant and a derivative. In one embodiment, the peptides of the invention are synthesized with α,α-disubstituted non-natural amino acids containing olefin-bearing tethers, followed by an all-hydrocarbon "staple" by ruthenium catalyzed olefin metathesis. (Scharmeister et al., J. Am. Chem. Soc. 122:5891-5892 (2000); Walensky et al., Science 305: 1466-1470 (2004)). Additionally, peptides that are structural equivalents of azurin may be fused to other peptides, thus making a peptide that is both a structural equivalent and a derivative. These examples are merely to illustrate and not to limit the invention. Variants, derivatives or structural equivalents of cupredoxin may or may not bind copper.

In another embodiment, the peptide is a structural equivalent of a cupredoxin. Examples of studies that determine significant structural homology between cupredoxins and other proteins include Toth et al. (*Developmental Cell* 1:82-92 (2001)). Specifically, significant structural homology between a cupredoxin and the structural equivalent is determined by using the VAST algorithm. (Gibrat et al., Curr Opin Struct Biol 6:377-385 (1996); Madej et al., Proteins 23:356-3690 (1995)). In specific embodiments, the VAST p value from a structural comparison of a cupredoxin to the structural equivalent is less than about $10^{-3}$, less than about $10^{-5}$, or less than about $10^{-7}$. In other embodiments, significant structural homology between a cupredoxin and the structural equivalent is determined by using the DALI algorithm (Holm & Sander, J. Mol. Biol. 233:123-138 (1993)). In specific embodiments, the DALI Z score for a pairwise structural comparison is at least about 3.5, at least about 7.0, or at least about 10.0. Examples of these determinations are found in Examples 2 and 9.

In some embodiments, the cupredoxin, or variant, derivative or structural equivalent thereof has some of the functional characteristics of the *P. aeruginosa* azurin, *Ulva pertusa* plastocyanin, *Phormidium laminosum* plastocyanin or *Thiobacillis ferrooxidans* rusticyanin. In a specific embodiment, the cupredoxin or variant, derivative or structural equivalent thereof inhibits interferes with the ephrin-signaling system, and/or inhibits the growth of cancer in mammalian cells and tissues. The inhibition of growth of mammalian cancer cells or tissues may or may not be related to any interference with the ephrin-signaling system by the cupredoxin, or variant, derivative or structural equivalent thereof. Methods that determine whether the cupredoxin, or variant, derivative or structural equivalent thereof interferes with ephrin signaling are well known in the art, and include the determining of whether the cupredoxin, or variant, derivative or structural equivalent thereof binds to a component of the ephrin signaling pathway, such as, but not limited to, an ephrin and/or an ephrin receptor. The ephrin signaling system at its broadest includes the ephrin and associated ephrin receptor, and any molecules (or "components") required to transmit the signal both backward and forward. In a narrower view, the ephrin signaling system includes only the ephrin and related ephrin receptor responsible for the signaling. The term "interfere" when used in the context of the ephrin signaling system can result in either an increase or decrease of the associated ephrin signaling, in either or both of the "forward" and "backward" directions. Methods to measure the interference in the ephrin signaling system are well known in the art. One method to determine interference of ephrin signaling is the binding or competition of the peptide to or with an ephrin or ephrin receptor, or other component of the ephrin signaling system, as shown in Examples 6-8. In vivo systems can be used, such as the *C. elegans* where it is now known that cupredoxins can interfere with ephrin signaling to alter tail muscle formation and embryonic development, as described in Example 1. Other methods include, but are not limited to, the Eph receptor phosphorylation assay in Himanen et al. (Nat. Neurosci. 7:501-509 (2004)). and Koolpe et al. (J. Biol. Chem. 280: 17301-17311 (2005)).

Because it is now known that cupredoxins and variants of cupredoxins can, among other things, interfere with ephrin signaling and inhibit the growth of cancer in mammalian cells and tissues, it is now possible to design variants, derivatives and structural equivalents of cupredoxins that retain this activity, for example. Such variants, derivatives and structural equivalents can be made by, for example, creating a "library" of various variants, derivatives and structural equivalents of, and then testing each for anti-cancer activity, for example, using one of many methods known in the art, such as the exemplary methods in Examples 3, 9 and 10. It is contemplated that the resulting variants, derivatives and structural equivalents of cupredoxins with anti-cancer activity can be used in the methods of the invention, in place of or in addition to cupredoxins.

In other embodiments, the cupredoxin, or variant, derivative or structural equivalent thereof may have a significant structural homology with an ephrin. In a specific embodiment, the cupredoxins and variants and derivative of cupredoxins have a significant structural homology around the G-H loop region of ephrin. Examples of studies that determine significant structural homology between cupredoxins and ephrins include Toth et al. (*Developmental Cell* 1:82-92 (2001)). and Example 2 herein. Specifically, significant structural homology between a cupredoxin and an ephrin is determined by using the VAST algorithm. (Gibrat et al., Curr Opin Struct Biol 6:377-385 (1996); Madej et al., Proteins 23:356-3690 (1995)). In specific embodiments, the VAST p value from a structural comparison of a cupredoxin to an ephrin is less than about $10^{-3}$, less than about $10^{-5}$, or less than about $10^{-7}$. In other embodiments, significant structural homology between a cupredoxin and an ephrin is determined by using the DALI algorithm (Holm & Sander, J. Mol. Biol. 233:123-138 (1993)). In specific embodiments, the DALI Z score for a pairwise structural comparison is at least about 3.5, at least about 7.0, or at least about 10.0.

In another embodiment, the cupredoxin, or variant, derivative or structural equivalent thereof binds to either an ephrin and/or an Eph receptor. It is now known that several cupredoxins have a C-terminal region that is structurally similar to ephrinB2 ectodomain. See Examples 2, 5 and 9. In a specific embodiment, the cupredoxin, or variant, derivative or structural equivalent thereof bind to an ephrin. In a particularly specific embodiment, the ephrin is, but is not limited to, ephrinA1, ephrinA2, ephrinA3, ephrinA4, ephrinA5, ephrinB1, ephrinB2, ephrinB3 and ephrinB4. In a particularly specific embodiment, the ephrin is, but is not limited to, ephrinB1, ephrinB2, ephrinB3 and ephrinB4. In another specific embodiment, the cupredoxin, or variant, derivative or structural equivalent thereof binds to an Eph receptor. In particularly specific embodiments, the Eph receptor is, but is not limited to, EphA 1, EphA2, EphA3, EphA4, EphA5, EphA6, EphA7, EphA8, EphA10, EphB1, EphB2, EphB3, EphB4 and EphB6. In some embodiments, the cupredoxin, or variant, derivative or structural equivalent thereof binds to both a ephrin and an ephrin receptor. In some embodiments, the cupredoxin, or variant, derivative or structural equivalent thereof binds to a ephrin and its receptor, specifically EphrinB2 and EphB2. Methods for determining the binding of proteins to other proteins are well known in the art. Examples of methods determining binding to Eph receptors include Examples 6-8, as well as Koolpe et al. (J. Biol. Chem. 280:17301-17311 (2005)). and Himanen et al. (Nat. Neurosci. 7:501-509 (2004)).

In some specific embodiments, the cupredoxin, or variant, derivative or structural equivalent thereof induces apoptosis in a mammalian cancer cell, more specifically a J774 cell. The ability of a cupredoxin or other polypeptide to induce apoptosis may be observed by mitosensor ApoAlert confocal microscopy using a MITOSENSOR™ APOLERT™ Mitochondrial Membrane Sensor kit (Clontech Laboratories, Inc., Palo Alto, Calif., U.S.A.), by measuring caspase-8, caspase-9 and caspase-3 activity using the method described in Zou et al. (J. Biol. Chem. 274: 11549-11556 (1999)), and by detecting apoptosis-induced nuclear DNA fragmentation using, for example, the APOLERT™ DNA fragmentation kit (Clontech Laboratories, Inc., Palo Alto, Calif., U.S.A.).

In another specific embodiment, the cupredoxin, or variant, derivative or structural equivalent thereof induces cellular growth arrest in a mammalian cancer cell, more specifically a J774 cell. Cellular growth arrest can be determined by measuring the extent of inhibition of cell cycle progression, such as by the method found in Yamada et al. (*PNAS* 101:4770-4775 (2004)). In another specific embodiment, the cupredoxin, or variant, derivative or structural equivalent thereof inhibits cell cycle progression in a mammalian cancer cell, more specifically a J774 cell.

Cupredoxins

These small blue copper proteins (cupredoxins) are electron transfer proteins (10-20 kDa) that participate in bacterial electron transfer chains or are of unknown function. The copper ion is solely bound by the protein matrix. A special distorted trigonal planar arrangement to two histidine and one cysteine ligands around the copper gives rise to very peculiar electronic properties of the metal site and an intense blue color. A number of cupredoxins have been crystallographically characterized at medium to high resolution.

The cupredoxins in general have a low sequence homology but high structural homology. (Gough & Clothia, Structure 12:917-925 (2004); De Rienzo et al., Protein Science 9:1439-1454 (2000).) For example, the amino acid sequence of azurin is 31% identical to that of auracyanin B, 16.3% to that of rusticyanin, 20.3% to that of plastocyanin, and 17.3% to that of pseudoazurin. See, Table 1. However, the structural similarity of these proteins is more pronounced. The VAST p value for the comparison of the structure of azurin to auracyanin B is $10^{-7.4}$, azurin to rusticyanin is $10^{-5}$, azurin to plastocyanin is $10^{-5.6}$, and azurin to psuedoazurin is $10^{-4.1}$.

All of the cupredoxins possess an eight-stranded Greek key beta-barrel or beta-sandwich fold and have a highly conserved site architecture. (De Rienzo et al., *Protein Science* 9:1439-1454 (2000).) A prominent hydrophobic patch, due to the presence of many long chain aliphatic residues such as methionines and leucines, is present around the copper site in azurins, amicyanins, cyanobacterial plastocyanins, cucumber basic protein and to a lesser extent, pseudoazurin and eukaryotic plastocyanins. Id. Hydrophobic patches are also found to a lesser extent in stellacyanin and rusticyanin copper sites, but have different features. Id.

TABLE 1

Sequence and structure alignment of azurin (1JZG) from *P. aeruginosa* to other proteins using VAST algorithm.

| PDB | Alignment length[1] | % aa identity | P-value[2] | Score[3] | RMSD[4] | Description |
|---|---|---|---|---|---|---|
| 1AOZ A 2 | 82 | 18.3 | 10e−7 | 12.2 | 1.9 | Ascorbate oxidase |
| 1QHQ_A | 113 | 31 | 10e−7.4 | 12.1 | 1.9 | AuracyaninB |
| 1V54 B 1 | 79 | 20.3 | 10e−6.0 | 11.2 | 2.1 | Cytocrome c oxidase |
| 1GY2 A | 92 | 16.3 | 10e−5.0 | 11.1 | 1.8 | Rusticyanin |
| 3MSP A | 74 | 8.1 | 10e−6.7 | 10.9 | 2.5 | Motile Major Sperm Protein[5] |
| 1IUZ | 74 | 20.3 | 10e−5.6 | 10.3 | 2.3 | Plastocyanin |
| 1KGY E | 90 | 5.6 | 10e−4.6 | 10.1 | 3.4 | Ephrinb2 |
| 1PMY | 75 | 17.3 | 10e−4.1 | 9.8 | 2.3 | Pseudoazurin |

[1] Aligned Length: The number of equivalent pairs of C-alpha atoms superimposed between the two structures, i.e. how many residues have been used to calculate the 3D superposition.
[2] P-VAL: The VAST p value is a measure of the significance of the comparison, expressed as a probability. For example, if the p value is 0.001, then the odds are 1000 to 1 against seeing a match of this quality by pure chance. The p value from VAST is adjusted for the effects of multiple comparisons using the assumption that there are 500 independent and unrelated types of domains in the MMDB database. The p value shown thus corresponds to the p value for the pairwise comparison of each domain pair, divided by 500.
[3] Score: The VAST structure-similarity score. This number is related to the number of secondary structure elements superimposed and the quality of that superposition. Higher VAST scores correlate with higher similarity.
[4] RMSD: The root mean square superposition residual in Angstroms. This number is calculated after optimal superposition of two structures, as the square root of the mean square distances between equivalent C-alpha atoms. Note that the RMSD value scales with the extent of the structural alignments and that this size must be taken into consideration when using RMSD as a descriptor of overall structural similarity.
[5] *C. elegans* major sperm protein proved to be an ephrin antagonist in oocyte maturation (Kuwabara, 2003 "The multifaceted *C. elegans* major sperm protein: an ephrin signalling antagonist in oocyte maturation" Genes and Development, 17:155-161.

Azurin

The azurins are copper-containing proteins of 128 amino acid residues which belong to the family of cupredoxins involved in electron transfer in certain bacteria. The azurins include those from *P. aeruginosa* (PA) (SEQ ID NO: 1), *A. xylosoxidans*, and *A. denitrificans*. (Murphy et al., J. Mol. Biol. 315:859-871 (2002)). The amino acid sequence identity between the azurins varies between 60-90%, these proteins showed a strong structural homology. All azurins have a characteristic β-sandwich with Greek key motif and the single copper atom is always placed at the same region of the protein. In addition, azurins possess an essentially neutral hydrophobic patch surrounding the copper site. Id.

Plastocyanins

The plastocyanins are soluble proteins of cyanobacteria, algae and plants that contain one molecule of copper per molecule and are blue in their oxidized form. They occur in the chloroplast, where they function as electron carriers. Since the determination of the structure of poplar plastocyanin in 1978, the structure of algal (*Scenedesmus, Enteromorpha, Chlamydomonas*) and plant (French bean) plastocyanins has been determined either by crystallographic or NMR methods, and the poplar structure has been refined to 1.33 Å resolution. SEQ ID NO: 2 shows the amino acid sequence of plastocyanin from *Phormidium laminosum*, a thermophilic cyanobacterium. SEQ ID NO: 22 shows the amino acid sequence of plastocyanin from *Ulva petrusa*.

Despite the sequence divergence among plastocyanins of algae and vascular plants (e.g., 62% sequence identity between the *Chlamydomonas* and poplar proteins), the three-dimensional structures are conserved (e.g., 0.76 Å rms deviation in the C alpha positions between the *Chlamydomonas* and *Poplar* proteins). Structural features include a distorted tetrahedral copper binding site at one end of an eight-stranded antiparallel beta-barrel, a pronounced negative patch, and a flat hydrophobic surface. The copper site is optimized for its electron transfer function, and the negative and hydrophobic patches are proposed to be involved in recognition of physiological reaction partners. Chemical modification, cross-linking, and site-directed mutagenesis experiments have confirmed the importance of the negative and hydrophobic patches in binding interactions with cytochrome f, and validated the model of two functionally significant electron transfer paths involving plastocyanin. One putative electron transfer path is relatively short (approximately 4 Å) and involves the solvent-exposed copper ligand His-87 in the hydrophobic patch, while the other is more lengthy (approximately 12-15 Å) and involves the nearly conserved residue Tyr-83 in the negative patch. (Redinbo et al., J. Bioenerg. Biomembr. 26:49-66 (1994)).

Rusticyanins

Rusticyanins are blue-copper containing single-chain polypeptides obtained from a *Thiobacillus* (now called *Acidithiobacillus*). The X-ray crystal structure of the oxidized form of the extremely stable and highly oxidizing cupredoxin rusticyanin from *Thiobacillus ferrooxidans* (SEQ ID NO: 3) has been determined by multiwavelength anomalous diffraction and refined to 1.9 Å resolution. The rusticyanins are composed of a core beta-sandwich fold composed of a six- and a seven-stranded b-sheet. Like other cupredoxins, the copper ion is coordinated by a cluster of four conserved residues (His 85, Cys138, His143, Met148) arranged in a distorted tetrahedron. (Walter et al., J. Mol. Biol. 263:730-51 (1996)).

Pseudoazurins

The pseudoazurins are a family of blue-copper containing single-chain polypeptide. The amino acid sequence of pseudoazurin obtained from *Achromobacter cycloclastes* is shown in SEQ ID NO: 4. The X-ray structure analysis of pseudoazurin shows that it has a similar structure to the azurins although there is low sequence homology between these proteins. Two main differences exist between the overall structure of the pseudoazurins and azurins. There is a carboxy terminus extension in the pseudoazurins, relative to the azurins, consisting of two alpha-helices. In the mid-peptide region azurins contain an extended loop, shortened in the pseudoazurins, which forms a flap containing a short α-helix. The only major differences at the copper atom site are the conformation of the MET side-chain and the Met-S copper bond length, which is significantly shorter in pseudoazurin than in azurin.

Phytocyanins

The proteins identifiable as phytocyanins include, but are not limited to, cucumber basic protein, stellacyanin, mavicyanin, umecyanin, a cucumber peeling cupredoxin, a putative blue copper protein in pea pods, and a blue copper protein from *Arabidopsis thaliana*. In all except cucumber basic protein and the pea-pod protein, the axial methionine ligand normally found at blue copper sites is replaced by glutamine.

Auracyanin

Three small blue copper proteins designated auracyanin A, auracyanin B-1, and auracyanin B-2 have been isolated from the thermophilic green gliding photosynthetic bacterium *Chloroflexus aurantiacus*. The two B forms are glycoproteins and have almost identical properties to each other, but are distinct from the A form. The sodium dodecyl sulfate-polyacrylamide gel electrophoresis demonstrates apparent monomer molecular masses as 14 (A), 18 (B-2), and 22 (B-1) kDa.

The amino acid sequence of auracyanin A has been determined and showed auracyanin A to be a polypeptide of 139 residues. (Van Dreissche et al; Protein Science 8:947-957 (1999).) His58, Cys123, His128, and Met132 are spaced in a way to be expected if they are the evolutionary conserved metal ligands as in the known small copper proteins plastocyanin and azurin. Secondary structure prediction also indicates that auracyanin has a general beta-barrel structure similar to that of azurin from *Pseudomonas aeruginosa* and plastocyanin from poplar leaves. However, auracyanin appears to have sequence characteristics of both small copper protein sequence classes. The overall similarity with a consensus sequence of azurin is roughly the same as that with a consensus sequence of plastocyanin, namely 30.5%. The N-terminal sequence region 1-18 of auracyanin is remarkably rich in glycine and hydroxy amino acids. Id. See exemplary amino acid sequence SEQ ID NO: 15 for chain A of auracyanin from *Chloroflexus aurantiacus* (NCBI Protein Data Bank Accession No. AAM12874).

The auracyanin B molecule has a standard cupredoxin fold. The crystal structure of auracyanin B from *Chloroflexus aurantiacus* has been studied. (Bond et al., J. Mol. Biol. 306:47-67 (2001); the contents of which are incorporated for all purposes by reference.) With the exception of an additional N-terminal strand, the molecule is very similar to that of the bacterial cupredoxin, azurin. As in other cupredoxins, one of the Cu ligands lies on strand 4 of the polypeptide, and the other three lie along a large loop between strands 7 and 8. The Cu site geometry is discussed with reference to the amino acid spacing between the latter three ligands. The crystallographically characterized Cu-binding domain of auracyanin B is probably tethered to the periplasmic side of the cytoplasmic membrane by an N-terminal tail that exhibits significant sequence identity with known tethers in several other membrane-associated electron-transfer proteins. The amino acid sequences of the B forms are presented in McManus et al. (J Biol Chem. 267:6531-6540 (1992).). See exemplary amino acid sequence SEQ ID NO: 16 for chain B of auracyanin from *Chloroflexus aurantiacus* (NCBI Protein Data Bank Accession No. 1QHQA).

Stellacyanin

Stellacyanins are a subclass of phytocyanins, a ubiquitous family of plant cupredoxins. An exemplary sequence of a stellacyanin is included herein as SEQ ID NO: 14. The crystal structure of umecyanin, a stellacyanin from horseradish root (Koch et al., *J. Am. Chem. Soc.* 127:158-166 (2005)). and cucumber stellacyanin (Hart et al., *Protein Science* 5:2175-2183 (1996)). is also known. The protein has an overall fold similar to the other phytocyanins. The ephrin B2 protein ectodomain tertiary structure bears a significant similarity to stellacyanin. (Toth et al., Developmental Cell 1:83-92 (2001).) An exemplary amino acid sequence of a stellacyanin is found in the National Center for Biotechnology Information Protein Data Bank as Accession No. 1JER, SEQ ID NO: 14.

Cucumber Basic Protein

An exemplary amino acid sequence from a cucumber basic protein is included herein as SEQ ID NO: 17. The crystal structure of the cucumber basic protein (CBP), a type I blue copper protein, has been refined at 1.8 Å resolution. The molecule resembles other blue copper proteins in having a Greek key beta-barrel structure, except that the barrel is open on one side and is better described as a "beta-sandwich" or "beta-taco". (Guss et al., J. Mol. Biol. 262: 686-705 (1996).) The ephrinB2 protein ectodomain tertiary structure bears a high similarity (rms deviation 1.5 Å for the 50 α carbons) to the cucumber basic protein. (Toth et al., Developmental Cell 1:83-92 (2001).)

The Cu atom has the normal blue copper NNSS' co-ordination with bond lengths Cu—N(His39)=1.93 Å, Cu—S (Cys79)=2.16 Å, Cu—N(His84)=1.95 Å, Cu—S(Met89) =2.61 Å. A disulphide link, (Cys52)-S—S-(Cys85), appears to play an important role in stabilizing the molecular structure. The polypeptide fold is typical of a sub-family of blue copper proteins (phytocyanins) as well as a non-metalloprotein, ragweed allergen Ra3, with which CBP has a high degree of sequence identity. The proteins currently identifiable as phytocyanins are CBP, stellacyanin, mavicyanin, umecyanin, a cucumber peeling cupredoxin, a putative blue copper protein in pea pods, and a blue copper protein from *Arabidopsis thaliana*. In all except CBP and the pea-pod protein, the axial methionine ligand normally found at blue copper sites is replaced by glutamine. An exemplary sequence for cucumber basic protein is found in NCBI Protein Data Bank Accession No. 2CBP, SEQ ID NO: 17.

Methods of the Invention

Another aspect of the present invention relates to the use of one or more cupredoxins and variants, derivatives and structural equivalents thereof in a method to treat a mammalian patient suffering from a pathological condition. More specifically, the condition is related to the ephrin signaling system. Additionally, the mammalian patient may be suffering from cancer.

In general, it is now known that cupredoxins and variants, derivatives and structural equivalents thereof will interfere with the activity of the ephrin signaling system in a cell or tissue. In addition, it is now known that cupredoxins and variants, derivatives and structural equivalents thereof will inhibit the growth of cancer in cells and tissues. In specific embodiments, the cell or tissue is mammalian. In more specific embodiments, the cell is human. In some embodiments, the cell is not human. In one embodiment, the cupredoxin and variant, derivative or structural equivalent thereof is administered to a cell to inhibit the activity of an ephrin receptor on the surface of the cell. In another embodiment, the cupredoxin and variant, derivative or structural equivalent thereof is administered to increase the activity of an ephrin receptor on the surface of the cell. In other specific embodiments, the cupredoxin and variants and derivatives of cupredoxin inhibit and/or increase the forward and/or backward ephrin signaling. Further, it is possible, for example, for a forward signal to be inhibited while a backwards signal is increased.

The pathological condition suffered by the mammalian patient is specifically one that is related to the activity of the ephrin signaling system. It is now appreciated that cupredoxins comprise a certain structural homology to ephrins, and can also act like ephrins in vivo in relation to the ephrin signaling system. It is contemplated that cupredoxins can be used to treat pathological conditions that are related to the ephrin signaling system. In specific embodiments, the pathological condition is accompanied by a higher than normal or lower than normal concentration of a component of the ephrin signaling system. In other specific embodiments, the pathological condition results from an over-expression or under-expression of a component of the ephrin signaling system. In other specific embodiments, the pathological condition results from the excessive turnover or lack of turnover of a component of the ephrin signaling system. In other specific embodiments, the pathological condition causes an over-expression or under-expression of a component of the ephrin signaling system. In another specific embodiment, the pathological condition causes excessive turnover or lack of turnover of a component of the ephrin signaling system. A "component" of the ephrin signaling system includes any molecule that transmits or causes to be transmitted a signal resulting from ephrin binding to an ephrin receptor. In more specific embodiments, the component is an ephrin or an ephrin receptor.

Additionally, the pathological condition can be accompanied by an abnormal distribution, either intracellular, intercellular, or tissue-specific, of a component of the ephrin signaling system. In a specific embodiment, the ephrin receptor is found in a higher concentration on the surface of a cell or cells. In a more specific embodiment, an ephrin receptor is up-regulated or down-regulated in a tissue. In another more specific embodiment, an ephrin is up-regulated or down-regulated in a tissue.

In another aspect of the invention, the cupredoxin, or variant, derivative or structural equivalent thereof is administered to a patent with cancer. In some embodiments, the patient is mammalian, and specifically human. In other embodiments, the patient is not human. While not limiting the mechanism of action of this treatment method, many cancers are associated with increased or decreased concentrations of components of ephrin signaling system. Many ephrins and Eph receptors have been shown to be up-regulated or down-regulated in tumors, particularly in the more aggressive stages of tumor progression. For example, EphA2 is up-regulated in breast, liver and prostate cancer, and glioblastoma, esophageal squamous cell cancer, ovarian cancer and melanoma. In a specific embodiment, the cancer is associated with up-regulated EphA2 receptor. However, it is known that in many cancers, different components of the ephrin signaling system are up-regulated or down-regulated, in particular, the ephrins and Eph receptors. Examples of the abnormal expression of ephrins and ephrin receptors in various tumors are well known in the art, and described in Surawska et al. (Cytokine & Growth Factor Reviews 15:419-433 (2004)). In other embodiments, the cancer is not associated with abnormal amounts of components or activities of the ephrin signaling system. In specific embodiments, the cancer is, but is not limited to, breast cancer, liver cancer, gastrointestinal cancer, neuroblastoma, neural cancer, leukemia, lymphoma, prostrate cancer, pancreatic cancer, lung cancer, melanoma, ovarian cancer, endometrial tumor, choriocarcinoma, teratocarcinoma, thyroid cancer, all sarcomas including those arising from soft tissues and bone, renal carcinomas, epidermoid cancer and non-small cell lung cancer. In a specific embodiment, the cancer is deficient in the expression of p53 tumor suppressor gene.

In other embodiments, the cancer has various attributes related to the stage of the tumor growth. An early step in tumor development is vascularization, where arteries are recruited to supply the tumor with blood. While not limiting the mechanism of operation to any one means, it is known that the ephrin signaling system is related to angiogenesis. In one embodiment, the cancer is one with which angiogenesis is associated. Another stage of tumor development is metastasis, where the tumor forms metastases, which are defined as tumor implants discontinuous with the primary tumor. While not limiting the mechanism of operation to any one means, it is thought that metastasis is also related to the ephrin signaling system. In one embodiment, the cancer is pre-metastatic. In another embodiment, the cancer is metastatic. Method of measuring an effect of a compound on angiogenesis are well-known in the art. Specific methods for measuring angiogenesis include, but are not limited to, the assays found in the following articles, the contents of which are incorporated for all purposes by reference: Daniel et al., *Kidney Int. Suppl.* 57:S73-S81 (1996); Myers et al., *J. Cell Biol.* 148:343-351 (2000); Pandey et al., *Science* 268:567-569 (1995); Brantley et al., *Oncogene* 21:7011-7026 (2002).

There are many pathological conditions in addition to tumors that are associated with the ephrin signaling pathway. For example, pathological forms of angiogenesis (Adams & Klein, *Trends Cardiov. Medicine* 10:183-188 (2000); Brantley-Sieders & Chen, *Angiogenesis* 7:17-28 (2004); Noren et al., *Proc. Natl. Acad. Sci. USA* 101:5583-558 (2004).), chronic pain following tissue damage (Battaglia et al., *Nat Neurosci.* 6:339-340 (2003)), inhibition of nerve regeneration after spinal cord injury (Goldscmit et al., *J. Neurosci.* 6:339-340 (2003)), and human congenital malformations (Twigg et al. Proc. Natl. Acad. Sci. USA 101:8652-8657 (2004); Wieland et al., Am. J. Hum. Genet. 74:1209-1215 (2004)), and specific embodiments of the invention use cupredoxin, or variants, derivatives or structural equivalents thereof to treat these pathological conditions. In specific embodiments, the pathological condition is interstitial cystitis (IC), lesions associated with inflammatory bowel disease (IBD), HIV infection, cardiovascular disease, central nervous system disorders, peripheral vascular diseases, viral diseases, degeneration of the central nervous system (Christopher Reeve's disease) and Alzheimer's disease. For methodology related to the treatment of patients with interstitial cystitis and inflammatory bowel disease, see, for example, U.S. Patent Application Publication 20050049176 (published Mar. 3, 2005, the contents of which are incorporated for all purposes by this reference.). For methodology related to the inhibition or stimulation of angiogenesis, see, for example, U.S. Patent Application Publication No. 20040136983 (published Jul. 15, 2004, the contents of which are incorporated for all purposes by this reference.).

For methodology related to therapies for osteogenesis, see, for example, U.S. Patent Application Publication No. 20040265808 (published Jul. 15, 2004, the contents of which are incorporated for all purposes by this reference.).

The cupredoxin or variant, derivative or structural equivalent of cupredoxin can be administered to the patient by many routes and in many regimens that will be well known to those in the art. In specific embodiments, the cupredoxin or variant or derivative of cupredoxin is administered intravenously, intramuscularly, subcutaneously or by injection into a tumor. In a specific embodiment, cupredoxin or variant, derivative or structural equivalent of cupredoxin is administered intravenously. In particularly specific embodiments, the cupredoxin or variant or derivative thereof is administered with chemotherapy to patients with cancer or recovering from cancer.

In addition to pathological conditions, the cupredoxin or variant, derivative or structural equivalent of cupredoxin can be used in therapeutic methods related to other conditions suffered by a patient. Such conditions can be the result of accidents which damage the nervous or vascular system, recovery from other therapies, such as surgery, and conditions related to old age, among others. In one embodiment, the patient requires the growth or regrowth of blood vessels and the cupredoxin or variant, derivative or structural equivalent of cupredoxin is administered to guide the growth of blood vessels. In another embodiment, the patient is in need of a decrease in the growth of blood vessels and the cupredoxin or variant, derivative or structural equivalent of cupredoxin is administered to inhibit the growth of blood vessels. In another embodiment, the cupredoxin or variant, derivative or structural equivalent of cupredoxin is administered to a patient in need of neuron generation or regeneration to guide the growth of neurons. In another embodiment the cupredoxin or variant, derivative or structural equivalent of cupredoxin is administered to a patient to promote osteogenesis.

Another aspect of the invention is a method to detect cells that display specific Ephrin receptors in vivo. It is now known that the cupredoxins contain a region of high structural homology to ephrin B2 and other ephrins, and that cupredoxins can bind with specificity to ephrin receptors in vitro. Therefore, cupredoxins will localize to the surface of cells expressing ephrin receptors. Accordingly, in some embodiments, cupredoxins or variants derivatives or structural equivalents of cupredoxins can be used to locate these Eph receptor-expressing cells and tissues amongst non-Eph receptor expressing cells or tissues. In addition, cupredoxins or variants derivatives or structural equivalents of cupredoxins that display a binding preference of a particular kind of Eph receptor can be used to locate cells or tissues specifically expressing that kind of Eph receptor. In one embodiment, the cupredoxin or variants or derivatives thereof are linked to a detectable probe and administered to a human patient, and the localization of the detectable probe is measured in the patient to determine the localization of the Eph receptor-expressing cells or tissues. In a particularly specific embodiment, the cell is a cancer cell. The detectable probe may be one of many currently known in the art. Probes of specific interest, include but are not limited to, fluorescent probes, radioactive probes, and iodine, gadolinium and gold.

In another embodiment of the invention, the cupredoxins or variants derivatives or structural equivalents of cupredoxins are linked to a drug and are administered to a human patient in order to deliver the drug to Eph receptor expressing cells or tissues. In another specific embodiment, the tissue is a tumor. In a particularly specific embodiment, the cell is a cancer cell. The drug may be any kind of chemical compound that has an effect on a cell expressing Eph receptors. The drug may be an organic or inorganic compound, including, but not limited to, a peptide, DNA molecule, RNA molecule, a pharmaceutical composition and derivatives of any of these. In specific embodiments, the drug is a toxin such as *Pseudomonas* exotoxin A domain III, or a chemical compound such as taxol, or other drug that kills cancer cells.

A cupredoxin or variant, derivative or structural equivalent of cupredoxin can be administered to a cell or a human patient by administering a DNA containing a coding region encoding the cupredoxin or variant, derivative or structural equivalent of cupredoxin operably linked to a promoter region that is expressed in the desired cell or tissue of the human patient. In a specific embodiment, a DNA encoding a cupredoxin or variant, derivative or structural equivalent of cupredoxin is administered to a patient in order to treat a condition amenable to treatment with cupredoxin or variant, derivative or structural equivalent of cupredoxin. Appropriate vectors and methods to administer them to cells and human patients are well known in the art. Methodologies to express foreign proteins in human subjects are well known in the art and can be adapted to express a cupredoxin or variant, derivative or structural equivalent of cupredoxin in patients. Exemplary protocols are found in the following U.S. patents, among other sources: U.S. Pat. No. 6,339,068, issued Jan. 15, 2002; U.S. Pat. No. 6,867,000, issued Mar. 15, 2005; U.S. Pat. No. 6,821,957, issued Nov. 23, 2004; U.S. Pat. No. 6,821,955, issued Nov. 23, 2004, U.S. Pat. No. 6,562,376, issued May 13, 2003; the contents of all of which are incorporated for all purposes by this reference. In more specific embodiments, the DNA encoding a cupredoxin or variant, derivative or structural equivalent of cupredoxin is injected into a tumor of a patient suffering from cancer. In more specific embodiments, the DNA encoding a cupredoxin or variant, derivative or structural equivalent of cupredoxin is injected into a tumor of a patient suffering from cancer.

In some embodiments, the pharmaceutical composition is administered to the patient by intravenous injection, intramuscular injection, subcutaneous injection, inhalation, topical administration, transdermal patch, suppository, or oral, and specifically intravenous injection. The pharmaceutical composition may be administered to the patient simultaneously or within 1 minute to 1 week or more of the administration of another drug known to treat specific pathological conditions related to ephrin signaling or cancer. The pharmaceutical composition may be administered at about the same time as another anti-cancer drug.

Pharmaceutical Compositions Comprising Cupredoxins and Variants, Derivatives and Structural Equivalents of Cupredoxins Pharmaceutical compositions comprising at least one cupredoxin or variant, derivative or structural equivalent of cupredoxin can be manufactured in any conventional manner, e.g., by conventional mixing, dissolving, granulating, dragee-making, emulsifying, encapsulating, entrapping, or lyophilizing processes. The substantially pure cupredoxins or variants, derivatives or structural equivalents of cupredoxins can be readily combined with a pharmaceutically acceptable carrier well-known in the art. Such carriers enable the preparation to be formulated as a tablet, pill, dragee, capsule, liquid, gel, syrup, slurry, suspension, and the like. Suitable excipients can also include, for example, fillers and cellulose preparations. Other excipients can include, for example, flavoring agents, coloring agents, detackifiers, thickeners, and other acceptable additives, adjuvants, or binders. General methodology on pharmaceutical dosage forms is found in Ansel et al., *Pharmaceutical Dosage Forms and Drug Delivery Systems* (Lippencott Williams & Wilkins, Baltimore Md. (1999)).

The composition comprising a cupredoxin, or variant, derivative or structural equivalent thereof used in the invention may be administered in a variety of ways, including by injection (e.g., intradermal, subcutaneous, intramuscular, intraperitoneal and the like), by inhalation, by topical administration, by suppository, by using a transdermal patch or by mouth. General information on drug delivery systems can be found in Ansel et al., Id. In some embodiments, the composition comprising a cupredoxin, or variant, derivative or structural equivalent thereof can be formulated and used directly as injectibles, for subcutaneous and intravenous injection, among others. The composition comprising a cupredoxin, or variant, derivative or structural equivalent thereof can also be taken orally after mixing with protective agents such as polypropylene glycols or similar coating agents.

When administration is by injection, the cupredoxin, or variant, derivative or structural equivalent thereof may be formulated in aqueous solutions, specifically in physiologically compatible buffers such as Hanks solution, Ringer's solution, or physiological saline buffer. The solution may contain formulatory agents such as suspending, stabilizing and/or dispersing agents. Alternatively, the cupredoxin, or variant, derivative or structural equivalent thereof may be in powder form for constitution with a suitable vehicle, e.g., sterile pyrogen-free water, before use. In some embodiments, the pharmaceutical composition does not comprise an adjuvant or any other substance added to enhance the immune response stimulated by the peptide. In some embodiments, the pharmaceutical composition comprises a substance that inhibits an immune response to the peptide.

When administration is by intravenous fluids, the intravenous fluids for use administering the cupredoxin, or variant, derivative or structural equivalent thereof may be composed of crystalloids or colloids. Crystalloids as used herein are aqueous solutions of mineral salts or other water-soluble molecules. Colloids as used herein contain larger insoluble molecules, such as gelatin. Intravenous fluids may be sterile.

Crystalloid fluids that may be used for intravenous administration include but are not limited to, normal saline (a solution of sodium chloride at 0.9% concentration), Ringer's lactate or Ringer's solution, and a solution of 5% dextrose in water sometimes called D5W, as described in Table 2.

TABLE 2

Composition of Common Crystalloid Solutions

| Solution | Other Name | [$Na^+$] | [$Cl^-$] | [Glucose] |
|---|---|---|---|---|
| D5W | 5% Dextrose | 0 | 0 | 252 |
| ⅔ & ⅓ | 3.3% Dextrose/ 0.3% saline | 51 | 51 | 168 |
| Half-normal saline | 0.45% NaCl | 77 | 77 | 0 |
| Normal saline | 0.9% NaCl | 154 | 154 | 0 |
| Ringer's lactate* | Ringer's solution | 130 | 109 | 0 |

*Ringer's lactate also has 28 mmol/L lactate, 4 mmol/L $K^+$ and 3 mmol/L $Ca^{2+}$.

When administration is by inhalation, the cupredoxin, or variant, derivative or structural equivalent thereof may be delivered in the form of an aerosol spray from pressurized packs or a nebulizer with the use of a suitable propellant, e.g., dichlorodifluoromethane, trichlorofluoromethane, carbon dioxide or other suitable gas. In the case of a pressurized aerosol, the dosage unit may be determined by providing a valve to deliver a metered amount. Capsules and cartridges of, e.g., gelatin, for use in an inhaler or insulator may be formulated containing a powder mix of the proteins and a suitable powder base such as lactose or starch.

When administration is by topical administration, the cupredoxin, or variant, derivative or structural equivalent thereof may be formulated as solutions, gels, ointments, creams, jellies, suspensions, and the like, as are well known in the art. In some embodiments, administration is by means of a transdermal patch. When administration is by suppository (e.g., rectal or vaginal), cupredoxin or variants, derivatives and structural equivalents thereof compositions may also be formulated in compositions containing conventional suppository bases.

When administration is oral, a cupredoxin, or variant, derivative or structural equivalent thereof can be readily formulated by combining the cupredoxin, or variant, derivative or structural equivalent thereof with pharmaceutically acceptable carriers well known in the art. A solid carrier, such as mannitol, lactose, magnesium stearate, and the like may be employed; such carriers enable the cupredoxin and variants, derivatives and structural equivalents thereof to be formulated as tablets, pills, dragees, capsules, liquids, gels, syrups, slurries, suspensions and the like, for oral ingestion by a subject to be treated. For oral solid formulations such as, for example, powders, capsules and tablets, suitable excipients include fillers such as sugars, cellulose preparation, granulating agents, and binding agents.

Other convenient carriers, as well-known in the art, also include multivalent carriers, such as bacterial capsular polysaccharide, a dextran or a genetically engineered vector. In addition, sustained-release formulations that include a cupredoxin, or variant, derivative or structural equivalent thereof allow for the release of cupredoxin, or variant, derivative or structural equivalent thereof over extended periods of time, such that without the sustained release formulation, the cupredoxin, or variant, derivative or structural equivalent thereof would be cleared from a subject's system, and/or degraded by, for example, proteases and simple hydrolysis before eliciting or enhancing a therapeutic effect.

The half-life in the bloodstream of the compositions of the invention can be extended or optimized by several methods well known to those in the art, including but not limited to, circularized peptides (Monk et al., BioDrugs 19(4):261-78, (2005); DeFreest et al., J. Pept. Res. 63(5):409-19 (2004)), D,L-peptides (diastereomer), (Futaki et al., J. Biol. Chem. Feb 23;276(8):5836-40 (2001); Papo et al., Cancer Res. 64(16):5779-86 (2004); Miller et al., Biochem. Pharmacol. 36(1):169-76, (1987)); peptides containing unusual amino acids (Lee et al., J. Pept. Res. 63(2):69-84 (2004)), N- and C-terminal modifications (Labrie et al., Clin. Invest. Med. 13(5):275-8, (1990)), and hydrocarbon stapling (Schafineister et al., J. Am. Chem. Soc. 122:5891-5892 (2000); Walenski et al., Science 305:1466-1470 (2004)). Of particular interest are d-isomerization (substitution) and modification of peptide stability via D-substitution or L-amino acid substitution.

In various embodiments, the pharmaceutical composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils, saline solutions, aqueous dextrose and glycerol solutions, other pharmaceutically acceptable auxiliary substances as required to approximate physiological conditions, such as buffering agents, tonicity adjusting agents, wetting agents and the like. It will be recognized that, while any suitable carrier known to those of ordinary skill in the art may be employed to administer the compositions of this invention, the type of carrier will vary depending on the mode of administration. Compounds may also be encapsulated within liposomes using well-known technology. Biodegradable microspheres may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

The pharmaceutical compositions may be sterilized by conventional, well-known sterilization techniques, or may be sterile filtered. The resulting aqueous solutions may be packaged for use as is, or lyophilized, the lyophilized preparation being combined with a sterile solution prior to administration.

Administration of Cupredoxins

The cupredoxin, or variant, derivative or structural equivalent thereof can be administered formulated as pharmaceutical compositions and administered by any suitable route, for example, by oral, buccal, inhalation, sublingual, rectal, vaginal, transurethral, nasal, topical, percutaneous, i.e., transdermal or parenteral (including intravenous, intramuscular, subcutaneous and intracoronary) administration. The pharmaceutical formulations thereof can be administered in any amount effective to achieve its intended purpose. More specifically, the composition is administered in a therapeutically effective amount. In specific embodiments, the therapeutically effective amount is generally from about 0.01-20 mg/day/kg of body weight.

The compounds comprising cupredoxin, or variant, derivative or structural equivalent thereof are useful for the treatment of a condition related to ephrin-signaling, or cancer in mammalian cells and tissues, alone or in combination with other active agents. The appropriate dosage will, of course, vary depending upon, for example, the compound of cupredoxin, or variant, derivative or structural equivalent thereof employed, the host, the mode of administration and the nature and severity of the conditions being treated. However, in general, satisfactory results in humans are indicated to be obtained at daily dosages from about 0.01-20 mg/kg of body weight. An indicated daily dosage in humans is in the range from about 0.7 mg to about 1400 mg of a compound of cupredoxin, or variant, derivative or structural equivalent thereof conveniently administered, for example, in daily doses, weekly doses, monthly doses, and/or continuous dosing. Daily doses can be in discrete dosages from 1 to 12 times per day. Alternatively, doses can be administered every other day, every third day, every fourth day, every fifth day, every sixth day, every week, and similarly in day increments up to 31 days or more. Alternatively, dosing can be continuous using patches, i.v. administration and the like.

The method of introducing cupredoxin and/or variant, derivative or structural equivalent thereof to patients is, in some embodiments, co-administration with other drugs known to treat specific pathological conditions related to ephrin signaling or cancer, or other conditions or diseases Such methods are well-known in the art. In a specific embodiment, the cupredoxin and/or variant, derivative or structural equivalent thereof are part of an cocktail or co-dosing containing or with other pathological conditions related to ephrin signaling or cancer. Drugs of interest include those used to treat inflammatory bowel disease, HIV infection, viral diseases, cardiovascular disease, peripheral vascular diseases, central nervous system disorders, degeneration of the central nervous system and Alzheimer's disease.

Drugs for treating with inflammatory bowel disease, include, but are not limited to, aminosalicylates, such as, sulfasalazine (Azulfidine®), olsalazine (Dipentum®), mesalamine (Asacol®, Pentasa®), and balsalazide (Colazal®); corticosteroids, such as, prednisone, Medrol®, methylprednisolone, hydrocortisone, Budesonide (Entocort EC); immunomodulators, such as, azathioprine (Imuran®), 6-mercaptopurine (6-MP, Purinethol®) and cyclosporine A (Sandimmune®, Neoral®); antibiotics, such as, metronidazole (Flagyl®) and ciprofloxacin (Cipro®); biologic therapies, such as, infliximab (Remicade®); and miscellaneous therapies, such as, tacrolimus (FK506) and mycophenolate mofetil.

Drugs for treating HIV infection include, but are not limited to, reverse transcriptase inhibitors: AZT (zidovudine [Retrovir®]), ddC (zalcitabine [Hivid®], dideoxyinosine), d4T (stavudine [Zerit®]), and 3TC (lamivudine [Epivir®]), nonnucleoside reverse transcriptase inhibitors (NNRTIS): delavirdine (Rescriptor®) and nevirapine (Viramune®), protease inhibitors: ritonavir (Norvir®), a lopinavir and ritonavir combination (Kaletra®), saquinavir (Invirase®), indinavir sulphate (Crixivan®), amprenavir (Agenerase®), and nelfinavir (Viracept®).

Drugs for treating viral diseases include, but are not limited to, acyclovir, varicella zoster immune globulin (VZIG®), peginterferon, ribavirin, acyclovir (Zovirax®), valacyclovir (Valtrex®), famciclovir (Famvir®), amantadine, rimantadine, zanamivir, oseltamivir, and alpha interferon.

Drugs for treating cardiovascular disorders include, but are not limited to, anticoagulants, antiplatelet agents, thrombolytic agents, adrenergic blockers, adrenergic stimulants, alpha/beta adrenergic blockers, angiotensin converting enzyme (ACE) inhibitors, angiotensin converting enzyme (ACE) inhibitors with calcium channel blockers, angiotensin converting enzyme (ACE) inhibitors with diuretics, angiotensin II receptor antagonists, calcium channel blockers, diuretics (including carbonic anhydrase inhibitors, loop diuretics, potassium-sparing diuretics, thiazides and related diuretics, vasodilators, vasopressors, etc.

Drugs for treating peripheral vascular disease include, but are not limited to, pentoxifylline (Trental®), an oral methylxanthine derivative, and cilostazol (Pletal®), a phosphodiesterase III inhibitor; antiplatelet/antithrombotic therapy such as aspirin; anticoagulants such as heparin and Warfarin® (Coumadin®); cholesterol lowering drugs, such as, niacin, statins, fibrates, Lopid® tablets (gemfibrozil; Parke-Davis); tricor tablets (fenofibrate; Abbott) bile acid sequestrants, Colestid® tablets (micronized colestipol hydrochloride; Pharmacia and Upjohn); Welchol® tablets (colesevelam hydrochloride; Sankyo); calcium channel blockers; vitamins and dietary supplements, such as, folate, B-6, B-12, L-arginine and omega-3 fatty acids; and HMG-COA Reductase inhibitors, such as, Advicor® tablets (Niacin/Lovastatin; Kos); Altocor® extended-release tablets (lovastatin; Andryx labs); Lescol® capsules (fluvastatin sodium; Novartis & Reliant); Lipitor® tablets (atorvastatin; Parke-Davis and Pfizer); Mevacor® tablets (lovastatin; Merck); Pravachol® tablets (Pravastatin sodium; Bristol-Myers Squibb) Pravigard® PAC tablets (Buffered Aspirin and Pravastatin Sodium; Bristol-Myers Squibb); Zocor® tablets (Simvastatin; Merck); nicotinic acid agents, such as, Advicor® tablets (Niacin/Lovastatin; Kos (also listed as a HMG-COA Reductase inhibitor)); Niaspan® (niacin; Kos); and miscellaneous agents, such as, Zetia® tablets (ezetimibe; Merck/Schering Plough).

Drugs for treating central nervous system disorders include, but are not limited to, psychotherapeutic agents, such as, various benzodiazepine preparations and combinations, antianxiety agents, antidepressants (including monoamine oxidase inhibitors (MAOI), selective serotonin reuptake inhibitors (SSRIs), tricyclic antidepressants), antimanic agents, antipanic agents, antipsychotic agents, psychostimulants, and obsessive-compulsive disorder management agents; migraine preparations, such as, beta adrenergic blocking agents, isometheptene and serotonin receptor agonists, as well as miscellaneous migraine preparations including active ingredients in Depakote® tablets (Divalproex sodium; Abbott) and Excedrin® migraine tablets (acetaminophen; BMS Products); sedatives and hypnotics; anticonvulsants; and Pimozide®. Drugs for treating Parkinson's disease include, but are not limited to, anticholinergic agents, catechol-o-methyltransferase inhibitors, dopamine agents and monoamine oxidase (MAO) inhibitors.

Drugs for treating CNS degeneration disorders include the following: Drugs for treating Multiple Sclerosis include, but are not limited to, active ingredients in Avonex® (interferon beta-1a; Biogen Neurology); Betaseron® for SC injection (modified form of Interferon beta-1b; Berlex); Copaxone® for injection (Glatiramer Acetate; Teva Neuroscience); Depo-Medrol® injectable suspension (Methylprednisolone acetate; Pharmacia & Upjohn); Novantrone® for injection concentrate (Mitoxantrone supplied as mitoxantrone hydrochloride; Serono); Orapred® oral solution (prednisolone sodium phosphate oral solution; Ascent); and Rebif® injection (interferon beta-1a; Pfizer & Serono). Drugs for treating Huntington's Disease include, but are not limited to, tranquilizers such as clonazepam (Klonopin®); antipsychotic drugs such as haloperidol (Haldol®) and clozapine (Clozaril®); fluoxetine (Prozac®, Sarafem®), sertraline (Zoloft®), nortriptyline (Aventyl®, Pamelor®), and lithium (Eskalith®, Lithobid®).

Drugs for treating Alzheimer's disease include, but are not limited to, Aricept® tablets (Donepezil Hydrochloride; Eisai or Pfizer); Exelon® capsules (rivastigmine (as the hydrogen tartrate salt); Novartis); Exelon® oral solution (rivastigmine tartrate; Novartis); Reminyl® oral solution (galantamine hydrobromide; Janssen) or Reminyl® tablets (galantamine hydrobromide; Janssen).

The method of introducing compounds comprising a cupredoxin, or variant, derivative or structurally equivalent thereof to patients is, in some embodiments, co-administration with other drugs known to treat cancer. Such methods are well-known in the art. In a specific embodiment, the compounds containing a cupredoxin, or variant, derivative or structurally equivalent thereof are part of an cocktail or co-dosing containing or with other drugs for treating cancer. Such drugs include, for example, those listed herein and specifically 5-fluorouracil; Interferon α; Methotrexate; Tamoxifen; and Vincrinstine. The above examples are provided for illustration only, many other such compounds are known to those skilled in the art.

Other drugs suitable for treating cancer include, but not limited to, alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5.alpha.-reductase inhibitors; inhibitors of 17.beta.-hydroxysteroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies. The compounds of the invention may also be used in conjunction with radiation therapy and surgery.

Representative examples of these classes of anti-cancer and cytotoxic agents include but are not limited to mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred members of these classes include, but are not limited to, paclitaxel, cisplatin, carboplatin, doxorubicin, caminomycin, daunorubicin, aminopterin, methotrexate, methopterin, mitomycin C, ecteinascidin 743, or pofiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine.

Examples of anticancer and other cytotoxic agents useful to co-administer with the compositions of the invention include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029 (the compounds of which U.S. patent can be employed together with any NHR modulators (including, but not limited to, those of present invention) such as AR modulators, ER modulators, with LHRH modulators, or with surgical techniques, especially in the treatment of cancer).

The exact formulation, route of administration, and dosage is determined by the attending physician in view of the patient's condition. Dosage amount and interval can be adjusted individually to provide plasma levels of the active cupredoxin, or variant, derivative or structural equivalent thereof which are sufficient to maintain therapeutic effect. Generally, the desired cupredoxin, or variant, derivative or structural equivalent thereof is administered in an admixture with a pharmaceutical carrier selected with regard to the intended route of administration and standard pharmaceutical practice.

In one aspect, the cupredoxin, or variant, derivative or structural equivalent thereof is delivered as DNA such that the polypeptide is generated in situ. In one embodiment, the DNA is "naked," as described, for example, in Ulmer et al., (Science 259:1745-1749 (1993)). and reviewed by Cohen (Science 259:1691-1692 (1993)). The uptake of naked DNA may be increased by coating the DNA onto a carrier, e.g., biodegradable beads, which are then efficiently transported into the cells. In such methods, the DNA may be present within any of a variety of delivery systems known to those of ordinary skill in the art, including nucleic acid expression systems, bacterial and viral expression systems. Techniques for incorporating DNA into such expression systems are well known to those of ordinary skill in the art. See, e.g., WO90/11092, WO93/24640, WO 93/17706, and U.S. Pat. No. 5,736,524.

Vectors, used to shuttle genetic material from organism to organism, can be divided into two general classes: cloning vectors are replicating plasmid or phage with regions that are essential for propagation in an appropriate host cell and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA, such as the DNA of a cupredoxin. In expression vectors, the introduced DNA is operably-linked to elements such as promoters that signal to the host cell to highly transcribe the inserted DNA. Some promoters are exceptionally useful, such as inducible promoters that control gene transcription in response to specific factors. Operably-linking a cupredoxin and variants, derivatives or structural equivalents thereof polynucleotide to an inducible promoter can control the expression of the cupredoxin and/or cytochrome c and variants and derivatives thereof in response to specific factors. Examples of classic inducible promoters include those that are responsive to α-interferon, heat shock, heavy metal ions, and steroids such as glucocorticoids (Kaufman, Methods Enzymol. 185:487-511 (1990)) and tetracycline. Other desirable inducible promoters include those that are not endogenous to the cells in which the construct is being introduced, but, are responsive in those cells when the induction agent is exogenously supplied. In general, useful expression vectors are often plasmids. However, other forms of expression vectors, such as viral vectors (e.g., replication defective retroviruses, adenoviruses and adeno-associated viruses) are contemplated.

Vector choice is dictated by the organism or cells being used and the desired fate of the vector. In general, vectors comprise signal sequences, origins of replication, marker genes, polylinker sites, enhancer elements, promoters, and transcription termination sequences.

Kits Comprising Cupredoxin, or Variant, Derivative or Structural Equivalent Thereof In one aspect, the invention provides kits containing one or more of the following in a package or container: (1) a biologically active composition comprising at least one cupredoxin, or variant, derivative or structural equivalent thereof; (2) a biologically active composition comprising a co-administered drug; (3) a pharmaceutically acceptable excipient; (4) a vehicle for administration, such as a syringe; (5) instructions for administration. Embodiments in which two or more of components (1)-(5) are found in the same packaging or container are also contemplated. The co-administered drug may be selected from those previously mentioned.

When a kit is supplied, the different components of the composition may be packaged in separate containers and admixed immediately before use. Such packaging of the components separately may permit long-term storage without losing the active components' functions.

The reagents included in the kits can be supplied in containers of any sort such that the life of the different components are preserved and are not adsorbed or altered by the materials of the container. For example, sealed glass ampules may contain lyophilized cupredoxin and variants, derivatives or structural equivalents thereof, or buffers that have been packaged under a neutral, non-reacting gas, such as nitrogen. Ampules may consist of any suitable material, such as glass, organic polymers, such as polycarbonate, polystyrene, etc., ceramic, metal or any other material typically employed to hold similar reagents. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, flash memory device etc. Detailed instructions may not be physically associated with the kit; instead, a user may be directed to an internet web site specified by the manufacturer or distributor of the kit, or supplied as electronic mail.

Modification of Cupredoxin and Variants, Derivatives or Structural Equivalents Thereof A cupredoxin, or variant, derivative or structural equivalent thereof may be chemically modified or genetically altered to produce variants and derivatives as explained above. Such variants and derivatives may be synthesized by standard techniques.

In addition to naturally-occurring allelic variants of cupredoxin, changes can be introduced by mutation into cupredoxin coding sequence that incur alterations in the amino acid sequences of the encoded cupredoxin that do not significantly alter the ability of cupredoxin to interfere with ephrin signaling or inhibit the growth of cancer. A "non-essential" amino acid residue is a residue that can be altered from the wild-type sequences of the cupredoxin without altering biological activity, whereas an "essential" amino acid residue is required for such biological activity. For example, amino acid residues that are conserved among the cupredoxins are predicted to be particularly non-amenable to alteration, and thus "essential."

Amino acids for which conservative substitutions that do not change the activity of the polypeptide can be made are well known in the art. Useful conservative substitutions are shown in Table 3, "Preferred substitutions." Conservative substitutions whereby an amino acid of one class is replaced with another amino acid of the same type fall within the scope of the invention so long as the substitution does not materially alter the biological activity of the compound.

TABLE 3

| Preferred substitutions | | |
|---|---|---|
| Original residue | Exemplary substitutions | Preferred substitutions |
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Non-conservative substitutions that affect (1) the structure of the polypeptide backbone, such as a β-sheet or α-helical conformation, (2) the charge, (3) hydrophobicity, or (4) the bulk of the side chain of the target site can modify the cytotoxic factor function. Residues are divided into groups based on common side-chain properties as denoted in Table 4. Non-conservative substitutions entail exchanging a member of one of these classes for another class. Substitutions may be introduced into conservative substitution sites or more specifically into non-conserved sites.

TABLE 4

Amino acid classes

| Class | Amino acids |
|---|---|
| hydrophobic | Norleucine, Met, Ala, Val, Leu, Ile |
| neutral hydrophilic | Cys, Ser, Thr |
| acidic | Asp, Glu |
| basic | Asn, Gln, His, Lys, Arg |
| disrupt chain conformation | Gly, Pro |
| aromatic | Trp, Tyr, Phe |

The variant polypeptides can be made using methods known in the art such as oligonucleotide-mediated (site-directed) mutagenesis, alanine scanning, and PCR mutagenesis. Site-directed mutagenesis (Carter, Biochem J. 237:1-7 (1986); Zoller and Smith, Methods Enzymol. 154:329-350 (1987)), cassette mutagenesis, restriction selection mutagenesis (Wells et al., Gene 34:315-323 (1985)) or other known techniques can be performed on the cloned DNA to produce the cupredoxin variant DNA.

Known mutations of cupredoxins can also be used to create variant cupredoxin to be used in the methods of the invention. For example, the C112D and M44KM64E mutants of Pseudomonas aeruginosa azurin are known to have cytotoxic and growth arresting activity that is different from the native azurin, and such altered activity can be useful in the treatment methods of the present invention. One embodiment of the methods of the invention utilize cupredoxin and variants and derivatives thereof retaining the ability to interfere with ephrin signaling or inhibit the growth of cancer in mammalian cells. In another embodiment, the methods of the present invention utilize cupredoxin variants such as the M44KM64E mutant, having the ability to cause cellular growth arrest.

A more complete understanding of the present invention can be obtained by reference to the following specific Examples. The Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations. Modifications and variations of the invention as hereinbefore set forth can be made without departing from the spirit and scope thereof, and, therefore, only such limitations should be imposed as are indicated by the appended claims.

EXAMPLES

Example 1

In Vivo Studies of C. elegans Development

Some ephrins are known in Caenorhabditis elegans to be involved in muscle formation in the tail and embryonic development. Our preliminary experiments indicate that rusticyanin interferes with tail muscle formation (causing paralysis of the tail) while azurin prevents baby birth (embryonic development).

In these experiments, the azurin and rusticyanin genes were hyper-expressed in E. coli. A control E. coli without azurin or rusticyanin genes was maintained. When C. elegans worms were fed control E. coli for up to 3 days, they were healthy and produced babies. When C. elegans were fed azurin-expressing E. coli, they seemed healthy but produced very few babies. When C. elegans were fed rusticyanin-expressing E. coli, about 30% could only move their heads or upper parts of their bodies but not their tails or the lower part of their body, demonstrating paralysis.

Example 2

Azurin Structural Neighbors Analysis

Protein structure neighbors analysis was determined by direct comparison of 3-dimensional protein structures in the Molecular Modeling DataBase with the Vector Alignment Search Tool (VAST) algorithm (Gibrat et al., Curr Opin Struct Biol 6:377-385 (1996); Madej et al., Proteins 23:356-3690 (1995)). The Molecular Modeling DataBase contains experimental data from crystallographic and NMR structure determinations and is maintained by the National Center for Biotechnology Information (Bethesda, Md., USA). A program that performs the VAST protein structure neighbors analysis is available through the National Center for Biotechnology Information.

Azurin showed a significant (Vast P value: 10 e-4.6; Alignment length: 90 aa; % Identity: 6) (FIG. 1), structural superposition with the MMDB (Molecular Modeling Database) entry 1 KGY E (crystal structure of the EphB2-EphrinB2 complex). The superposition alignment of azurin with the referred crystal structure is related to the chain E (138 aa), a protein denominated Ephrin (Ephrin-B2). This computational analysis is in accordance with the structural data published in Himanen et al. (Nature, vol 414: 933-938 (2001)).

Further VAST analysis indicates that the cupredoxins rusticyanin, auracyanin, plastocyanin, cucumber basic protein and stellacyanin also show significant structural homology to ephrinB2 in the G-H loop region. (FIG. 2)

Example 3

Efficacy of the Synthetic Peptides Derived from Azurin and Plastocyanin

The efficacy of the synthetic peptides derived from azurin and plastocyanin that are structurally similar to the human ephrin B-2 G-H loop has been analyzed. An 18-mer azurin peptide with the following sequence has been synthesized by standard techniques:

TFDVSKLKEGEQYMFFCT SEQ ID NO: 18

MCF-7 breast cancer cells were incubated in 16-well plates with 5 and 50 ug/ml of the 18-mer azurin peptide for 0, 24, 48 and 72 hours, after which the number of MCF-7 cells were counted in a coulter counter. The peptide was seen at 50 ug/ml to inhibit MCF-7 cell growth by 50% in 48 to 72 hours, as compared to cells without the synthetic peptide treatment. The extent of cell growth inhibition was about 25% at 5 ug/ml of the 18-mer synthetic peptide as compared to untreated control. This experiment shows that the synthetic peptide designed solely on its structural similarity to the B-2 ephrin does in fact inhibit the cancer cell progression promoted by the B-2 ephrin.

Example 4

In Vitro Measurement of Effect of Cupredoxins on the Growth of Mel-2 and MCF-7 Cells The growth of cells treated with cupredoxins was measured using a 16-well plate. Mel-2 or MCF-7 cells ($5 \times 10^5$ cells per well) were allowed to adhere to multiwell (16-well, in this instance) plates for 24 hours. After adherence, the growth medium was siphoned off. PBS (phosphate-buffered saline) or various cupredoxins/cytochromes at concentrations of 0.1 to 10 µM in PBS were then added to the wells containing fresh growth media and the growth of the cancer cells was followed for 24, 48 and 72 hours. After the incubation period, trypan blue was added to the culture and the number of dead floating cells was counted. Both live and dead floating cells were counted to determine the IC50 at various cupredoxin doses. The IC50 is the concentration of protein that inhibits the cell culture growth by 50%. At 500,000 cells per well at 24 hours of growth, enough cells were present for reproducible counts. In the cupredoxin-minus control cell cultures, as the cells grew, they had less space to adhere to the bottom of the well, began to die and became floating cells. In plastocyanin-treated or rusticyanin-treated cell cultures, the cells also overgrew the surface area of the well and began to die and float but their numbers were less than the control. However, in the azurin-treated cell cultures, both the Mel-2 and MCF-7 cell line growth was inhibited leading to very few floating cells.

Example 5

Structural Similarity Between EphrinB2 Ectodomain and Cupredoxins

Structural similarities between ephrinB2 ectodomain and cupredoxins were determined by using VAST and DALI algorithms (Holm and Sander, *J. Mol. Biol.* 233:123-138 (1993); Gibrat et al., *Curr. Opin. Biol.* 6"377-385 (1996)). respectively available through the U.S. National Institute of Heath and the European Bioinformatics Institute. Structure-based pairwise sequence alignments were calculated using the VAST algorithm. Protein structural diagrams are performed in two dimensions using TOPS (Topology Of Protein Structure) cartoons (Torrance et al., *Bioinformatics* 21:2537-2538 (2005)). The assessments of the structures were performed by using the program Mol Mol (Koradi et al., *J. Mol. Graphics* 14:51-55 (1996)).

Several homologs were found with both programs (data not shown), including a small subset of monomeric cupredoxin proteins, plastocyanin, azurin and rusticyanin. Specifically, the structural comparison between ephrinB2 ectodomain and these three cupredoxins (which are chosen as representative proteins of the cupredoxin family), provided VAST and DALI alignments with significant and quite similar scores, respectively ranging from 11.0 to 9.7 (out of a maximum possible 15.7) and 6.7 to 6.4. DALI Z scores <2.0 are structurally dissimilar (Table 5). The most notable structural conservation exists between the ephrinB2 ectodomain and plastocyanin, superimposed with a root mean square deviation (r.m.s.d.) of 1.8 Å (calculated over 67 structurally equivalent Cα atoms) (Table 5). Contrastingly, azurin, plastocyanin and rusticyanin exhibit weaker primary sequence identity (less than 10%) with the ephrinB2 ectodomain (Table 5).

TABLE 5

Structural similarity of the human ephrin B2 ectodomain to three members (plastocyanin, azurin and rusticyanin) of the monodomain cupredoxin family.

| PDB | Name | VAST score[a] | DALI Z score[b] | RMSD[c] to 1KGY_E | Alignment length | % Identity |
|---|---|---|---|---|---|---|
| 1IUZ | Plastocyanin | 11.0 | 6.4 | 1.8 | 67 | 9.0 |
| 1JZG | Azurin | 10.1 | 6.7 | 3.4 | 90 | 5.6 |
| 1RCY | Rusticyanin | 9.7 | 6.1 | 3.1 | 87 | 8.0 |

[a]VAST score—The VAST structure-similarity score; this number is related to the number of secondary structure elements superimposed and the quality of that superposition. Higher VAST scores correlate with higher similarity.
[b]DALI Z score—The Z scores are calculated using pairwise comparisions of the ephrin ectodomain structure with other structures in the DALI database. The higher the Z score, the less likely it is that the similarity between the 3D structures is random (pairs with Z < 2.0 are structurally dissimilar).
[c]RMSD—Root-mean-square deviation of backbone residues in angstroms between the aligned parts of the pair of structures.

FIG. 3 shows TOPS cartoons (A) and MolMol pictures (B) of the ephrinB2 ectodomain and each of the three cupredoxins under study. The topological description showed that the proteins adopt a sandwich of two β sheets which form the core of the Greek-key fold and show remarkable structural similarity in the way of the number and orientation of the β-strands; 1KGY_E (ephrinB2), 1IUZ (plastocyanin) and 1JZG_A (azurin) (FIG. 3). In contrast, the number and arrangement of α-helices are much less conserved. In JZG A, the helical structure is unique compared with the other proteins represented herein. As can be expected for proteins with different sizes, the loops that connect the elements of secondary structure showed differences in the lengths and their conformations. 1RCY (rusticyanin) has the lowest structural homology, with substantial differences in the lengths of shared secondary structure elements (SSEs) and the presence of non-shared SSEs Example 6

Analysis of Eph-Fc Receptor-Cupredoxin Interactions by Surface Plasmon Resonance Specific interactions of the Eph receptors with cupredoxins were determined by surface plasmon resonance (SPR) analyses. The human Astrocytoma CCF-STTG1, Glioblastoma LN 229 and MCF-7 (breast cancer) cells were cultured in RPMI medium 1640 containing 2 mM L-glutamine, 10 mM Hepes, 10% (vol/vol) heat-inactivated FBS, 100 units/ml penicillin, and 100 µg/ml streptomycin at 37° C. in a humidifier incubator with 5% CO2 as described earlier (Yamada et al., *Cell Microbiol.* 7:1418-1431 (2005); Hiraoka et al., *Proc. Natl. Acad. Sci. USA* 101: 6427-6432 (2004)). The human melanoma cells of UISO-Mel-2 (Yamada et al., *Proc. Natl. Acad. Sci. USA* 99:14098-14103 (2002)). were cultivated in MEM with Hank's medium supplemented with 10% FBS. *Escherichia coli* JM109 and BL21 (DE3) were used as host strains for hyperproduction of azurin, rusticyanin and plastocyanin. Azurin and rusticyanin were purified as described before (Yamada et al., *Proc. Natl. Acad. Sci. USA* 99:14098-14103 (2002); Yamada et al., Cell Cycle 3:1182-1187 (2004)). Construction and purification of GST-azurin fusion derivatives have been reported earlier (Yamada et al., *Cell Microbiol.* 7:1418-1431 (2005)). Purification and expression of plastocyanin from *Phormidium laminosum* was essentially carried out as described earlier (Schlarb et al., Gene 234:275-283 (1999)), except that *E. coli* strain BL21(DE3)Cd+(RIL) was used instead of BL21(DE3). The concentration of fully oxidized protein was determined spectrophotometrically at 598 nm, using an extinction coefficient of 4700 $M^{-1}$ $cm^{-1}$.

The Eph ectodomain Fc fusion proteins and ephrins were purchased as lypholized powders from R & D Systems, Minneapolis, Minn. All other chemicals used for surface plasmon resonance and growth experiments were purchased from Biacore AB International or Sigma and were of high analytical grade. Direct protein-protein interactions between cupredoxins or GST-peptides with Eph-Fc or ephrinB2-Fc were determined with a Biacore X biosensor system (Biacore AB) which is based on surface plasmon resonance (SPR) technology.

In initial screening experiments immobilization of azurin, rusticyanin, or plastocyanin to a single channel on the CM5 sensor chip was achieved using the amine coupling procedure. Sequential injections of N-hydroxysuccinimide/N-(3-dimethylaminopropyl)-N-ethylcarbodiimide (0.05M/0.2M, 35 µL), cupredoxin protein (255 µM, 50 µL), 1M ethanolamine (50 µL, pH 8.8), and 100 mM NaOH (10 µL) covalently linked the proteins to CM5 sensor chips with increases in resonance signals of 300 RU. Binding experiments were conducted via sequential injections of 100 nM of Eph-Fc proteins in HBS-EP running buffer (0.01 M HEPES, pH 7.4, 0.15 M NaCl, 3 mM EDTA, 0.005% v/v Surfactant P20) over the sensor surfaces at flow rates of 5 and 30 μL/min for 2.3 min (70 μL injection) with intermediate injections of 100 mM NaOH (10 μL pulse) to regenerate the cupredoxin-CM5 surface. All binding experiments were run against a bare Au CM5 sensor surface (negative channel) to correct for nonspecific binding.

The binding screens were conducted on cupredoxin modified sensor chips with sequential injection of 100 nM of Eph-Fc receptors at a flow rate of 30 μL/min over 2.3 min. The curves represent the beginning of the association phase for the interactions of Eph-Fc with azurin, plastocyanin, and rusticyanin. Relative binding affinities were taken as a function of the saturating resonances (Req) which varied from 79 RU for rusticyanin binding to EphB1-Fc or EphA8-Fc to 1248 RU for azurin binding to EphB2-Fc. The cross-selective binding of cupredoxins to specific EphA and EphB receptor proteins is notable with the best interactions occurring between cupredoxin and EphB.

Figure 4:
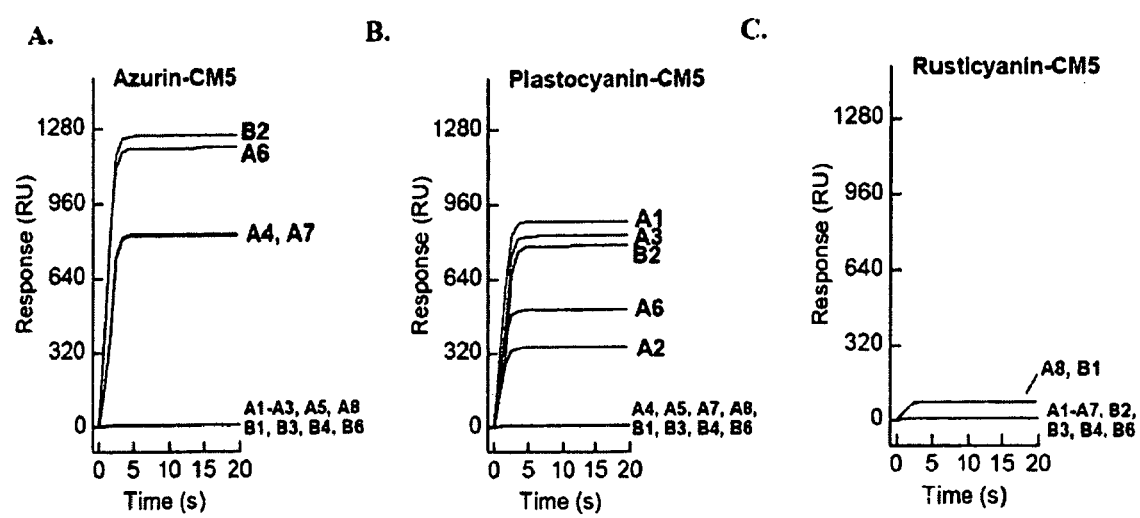
FIG. 4 depicts a surface plasmon resonance sensorgrams for the association of cupredoxins with bound Eph-Fc. Selective binding of azurin (FIG. 4A), plastocyanin (FIG. 4B), and rusticyanin (FIG. 4C) with EphA-Fc and EphB-Fc proteins is represented.

SPR sensorgrams for binding of immobilized cupredoxins with Eph-Fc indicated selective recognition between these two subsets of proteins (FIGS. 4A-C). In these measurements, Eph-Fc concentrations were kept constant at 100 nM so that the differences in the degree of association expressed in terms of Req reflect the differences in affinities between the Eph-Fc receptor proteins and cupredoxins. Azurin showed the highest affinity for EphB2-Fc and A6 and also tightly bound A4 and A7 (FIG. 4A). On the other hand, plastocyanin showed selectivity for EphA1-Fc, A3 and B2 and, to a lesser degree, A2 and A6 (FIG. 4B). Lastly, rusticyanin recognized EphA8-Fc, and B1, but only weakly (FIG. 4C). The associative interactions of azurin with EphB2-Fc and EphA6-Fc were the highest with Req values 1248 and 1200 RU respectively.

Example 7

Analysis of Binding Affinities of Azurin and GST-Azu Peptides with EphB2-Fc-SPR Binding Measurements Binding affinities of azurin and GST-azu peptides with EphB2-Fc-SPR binding measurements were performed with azurin or GST-Azu peptides using the immobilized EphB2-Fc to evaluate the relative binding affinity of the full length azurin or its various domains for the EphB2-Fc receptor. Azurin or GST-Azu peptides were injected at increasing concentrations (0.05-100 nM) to EphB2-Fc or ephrinB2-Fc modified CM5 chips with 100 mM NaOH pulses in between injections. The data were fit to a Langmuir (1:1) binding model [Req=Rmax/(1+Kd/C) to extrapolate equilibrium binding constants (Kd).

Figure 5:
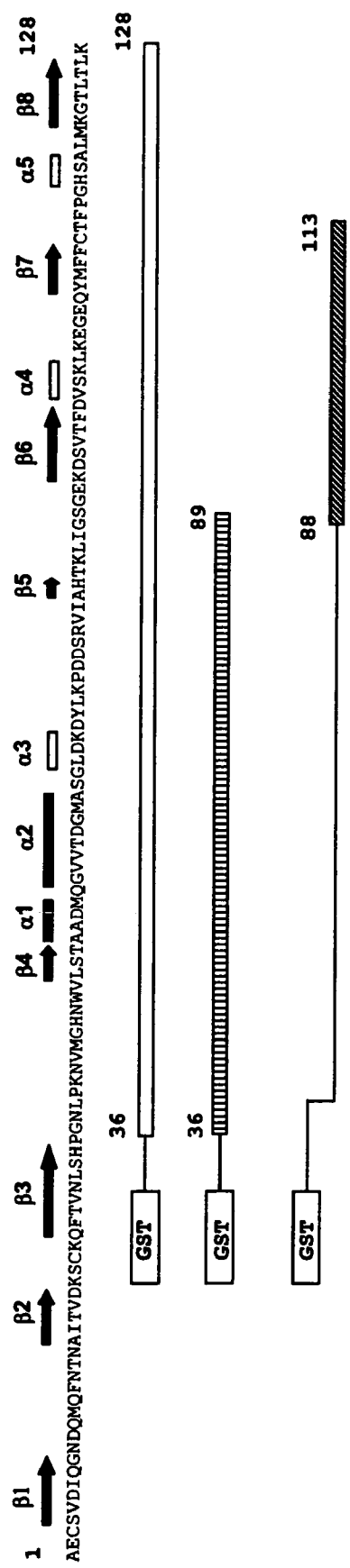
FIG. 5 depicts a schematic representation of various truncated azurin constructs derived from full length azurin (SEQ ID NO: 1). Secondary structure elements are illustrated as arrows for β-sheets and helices (alpha and 310) as rectangles. Various segments of the gene encoding the 128 amino acid azurin were fused at the 3'-end of the gst gene (encoding glutathione S-transferase) in frame, cloned in *E. coli*, hyperexpressed and the fusion proteins purified as described earlier (Yamada et al., Cell Micro. 7:1418-1431 (2005)).
Figure 6:
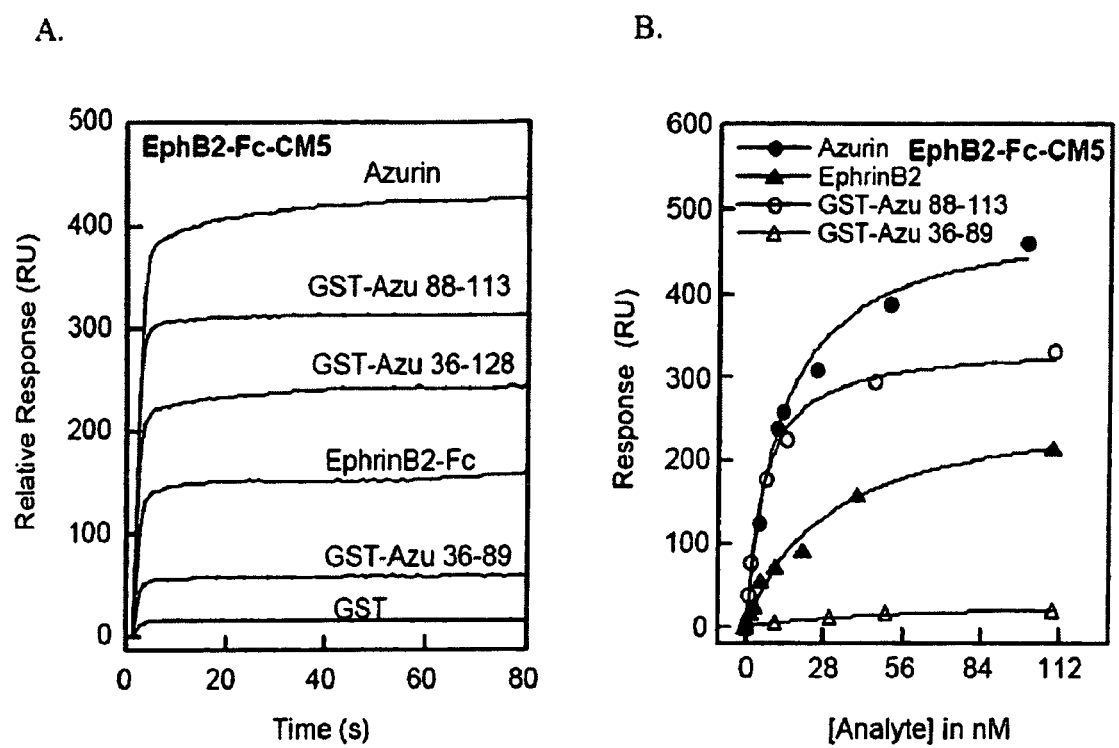
FIG. 6 depicts the relative binding affinities of azurin and selectively constructed GST-Azu fusions for EphB2-Fc determined in surface plasmon resonance studies.

The experimental strategy for elucidating the structural determinant of azurin for EphB2-Fc binding is shown in FIG. 5 which depicts the map of the primary/secondary structural parameters of azurin and the GST-Azu constructs as described earlier (Yamada et al., Cell Microbiol. 7:1418-1431 (2005)). In particular, the GST-Azu 88-113 is coincident with the GH loop region of ephrinB2 (native ligand) and therefore its binding efficacy with EphB2-Fc was of particular interest. Initial binding measurements of azurin and various GST-Azu constructs (all at 100 nM) for EphB2-Fc revealed their relative affinity: i.e., azurin>GST-Azu 88-113>GST-Azu 36-128>ephrinB2-Fc>GST-Azu 36-89>>GST (FIG. 6A). Azurin and GST-tagged azurin showed comparable affinities (data not shown). To quantify the binding affinities, the saturating response values (Req) for azurin or GST-Azu were measured as a function of their concentrations (0-100 nM) (FIG. 6B). The binding data were fit to a simple Langmuir (1:1) binding equation to determine equilibrium dissociation constants (Kd). Notably, azurin (Kd=6 nM) and GST-Azu 88-113 (Kd=12 nM) had 5- and 2.5-fold higher affinities, respectively, for EphB2-Fc than its native ephrinB2-Fc ligand (Kd=30 nM). Also, GST-Azu 36-128 (Table 6) showed slightly higher affinity (Kd=23 nM) than ephrinB2-Fc (Kd=30 nM). In contrast, GST-Azu 36-89 and GST exhibited negligible binding (Table 6). These data indicate the significance of the Azu 88-113 region of azurin for high affinity EphB2-Fc interaction. The Azu 88-113 region consists of the GH loop domain that is structurally homologous to the GH loop found in ephrinB2.

TABLE 6

Relative binding affinities of azurin and GST-Azu constructs with EphB2-Fc

| Analyte | $R_{eq}$ in RU | Molecular Weight | $K_d$ in nM |
| --- | --- | --- | --- |
| wt azurin | 427 | 13,929 | 6 ± 0.75 |
| ephrinB2-Fc | 159 | 130,200 | 30 ± 5.1 |
| GST | 14 | 26,000 | >160 |
| GST-Azu 36-128 | 244 | 36,076 | 23 ± 1.5 |
| GST-Azu 36-89 | 57 | 31,924 | 61 ± 9.0 |
| GST-Azu 88-113 | 314 | 28,943 | 12 ± 1.5 |

The relative binding strengths of azurin and GST-Azu constructs with EphB2-Fc were determined in SPR binding titration experiments and the extrapolated datasets are summarized here and are compared to the binding of native ephrinB2-Fc ligand and GST. The data from an initial screening experiment were generated upon injection of 100 nM of analyte to the sensor surfaces and the saturating signals ($R_{eq}$) are listed in resonance units. Saturation in the binding was achieved at each titration point in the binding curves depicted in FIG. 6b and these values plotted against [analyte] were used to calculate equilibrium dissociation constants ($K_d$). $K_d$ values ranged from 6 to 61 nM for the interactions of azurin and GST-Azu while EphB2-Fc with the native ligand had an intermediate binding affinity within this range.

Example 8

Analysis of Competition Binding Studies for Azurin/GST-Azu and EphrinB2-Fc with EphB2-Fc To better understand the physiological effects for the high-affinity azurin-EphB2-Fc binding, we performed further binding measurements. Competition binding titrations were conducted similar to the binding constant studies except that ephrinB2-Fc (246 nM)+competitor [azurin or GST-Azu (0-1020 nM)] were injected over the EphB2-Fc CM5 sensor surface.

Azurin+ephrinB2-Fc samples were added at different azurin concentrations (0-1020 nM, [ephrinB2-Fc] is 246 nM) to the sensor surface and the data were plotted as a ratio of resonances, % total response [Req(azurin+ephrinB2-Fc)/ (Req/(ephrinB2-Fc)).]. GST-Azu 88-113 and GST-Azu 36-89 were titrated with ephrinB2-Fc to immobilized EphB2-Fc and analyzed in a similar manner. Competition data suggest 1:1 stoichiometry of binding between azurin and GST-Azu 88-113 with immobilized EphB2-Fc.

Figure 7:
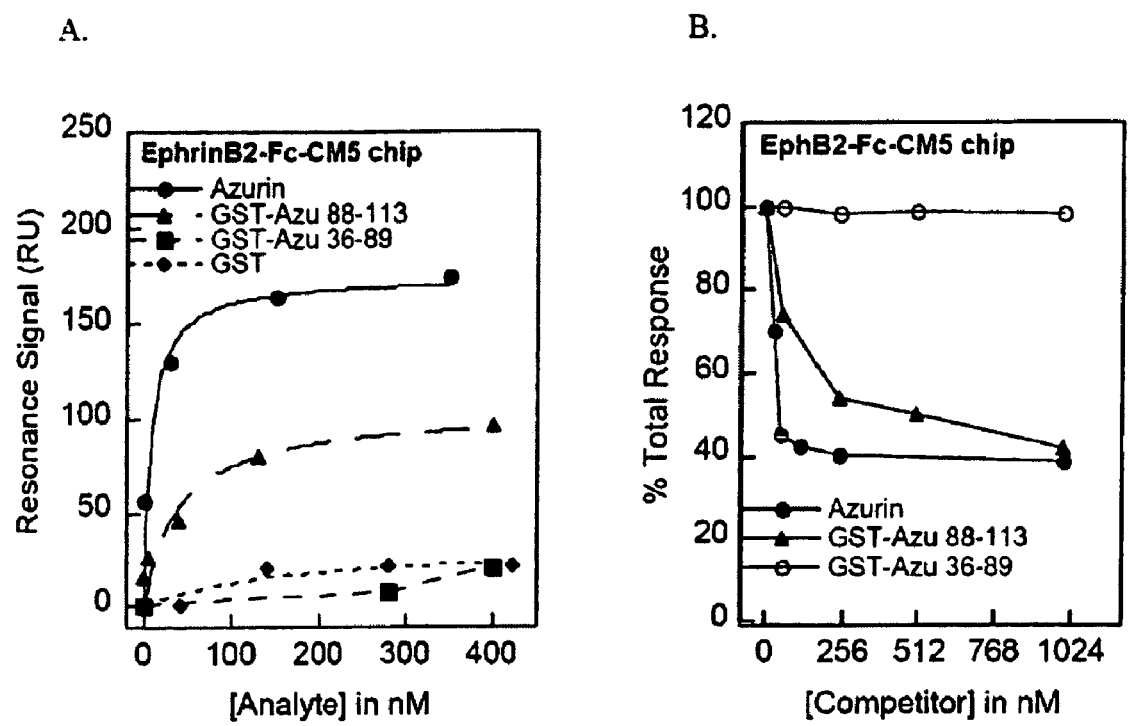
FIG. 7 depicts the binding interactions of azurin and GST-Azu with ephrinB2-Fc and EphB2-Fc determined in binding titrations and competition assays.

We first measured the binding of azurin and GST-Azu constructs to the EphB2-Fc ligand, ephrinB2-Fc. FIG. 7A shows that azurin indeed binds ephrinB2-Fc with high affinity (Kd=8.5+0.8 nM), reflecting the structural similarities between these two proteins (Table 5). Relative high affinity of GST-Azu 88-113 (Kd=39+6.5 nM) for ephrinB2-Fc indicates that the region between 88 and 113 is also responsible for binding to ephrinB2-Fc. In contrast, GST and GST-Azu 36-89 showed no significant interactions with ephrinB2-Fc. Taken together, these data indicate that azurin can bind with high affinity to both EphB2-Fc and ephrinB2-Fc via its GH loop (88-113) region.

To further test this notion, we performed SPR analysis of binding of ephrinB2-Fc to EphB2-Fc immobilized onto the CM5 sensor chip after ephrinB2-Fc is incubated with varying concentrations of azurin and GST-Azu constructs. FIG. 7B shows the inhibition of ephrinB2-Fc ([ephrinB2-Fc]=246 nM) binding to EphB2-Fc by 0-1020 nM of azurin, GST-Azu 88-113, and GST-Azu 36-89, respectively. The inhibition is expressed in terms of % total response (=[Req (azurin+ephrinB2-Fc)/Req(ephrinB2-Fc alone)]*100). The inhibition profiles indicate diminished binding of total protein to the immobilized EphB2-Fc when ephrinB2-Fc is preincubated with azurin or GST-Azu 88-113, with azurin being a more potent inhibitor than GST-Azu 88-113. The preincubation of azurin or GST-Azu 88-113 with ephrinB2-Fc reduced the total protein binding to the surface by up to 60%. GST-Azu 36-89, on the other hand, did not affect total protein binding (FIG. 7B), and this is consistent with its weak binding to either ephrinB2-Fc or EphB2-Fc. It appears that azurin (or GST-Azu 88-113) forms a stoichiometric complex with ephrinB2-Fc because maximal inhibition was achieved with 1 to 1 ratio of ephrinB2-Fc and azurin (or GST-Azu 88-113). The fact that the inhibition by azurin or GST-Azu 88-113 levels off at 40 to 50% indicates that the putative azurin-ephrinB2-Fc complex has some affinity for the EphB2-Fc receptor. Collectively, these binding data indicate that azurin has high affinity for both ephrinB2-Fc and EphB2-Fc and that it can interfere with ephrinB2-Fc-EphB2-Fc binding by a dual mechanism of ligand sequestration and receptor occupation.

Example 9

Figure 8:
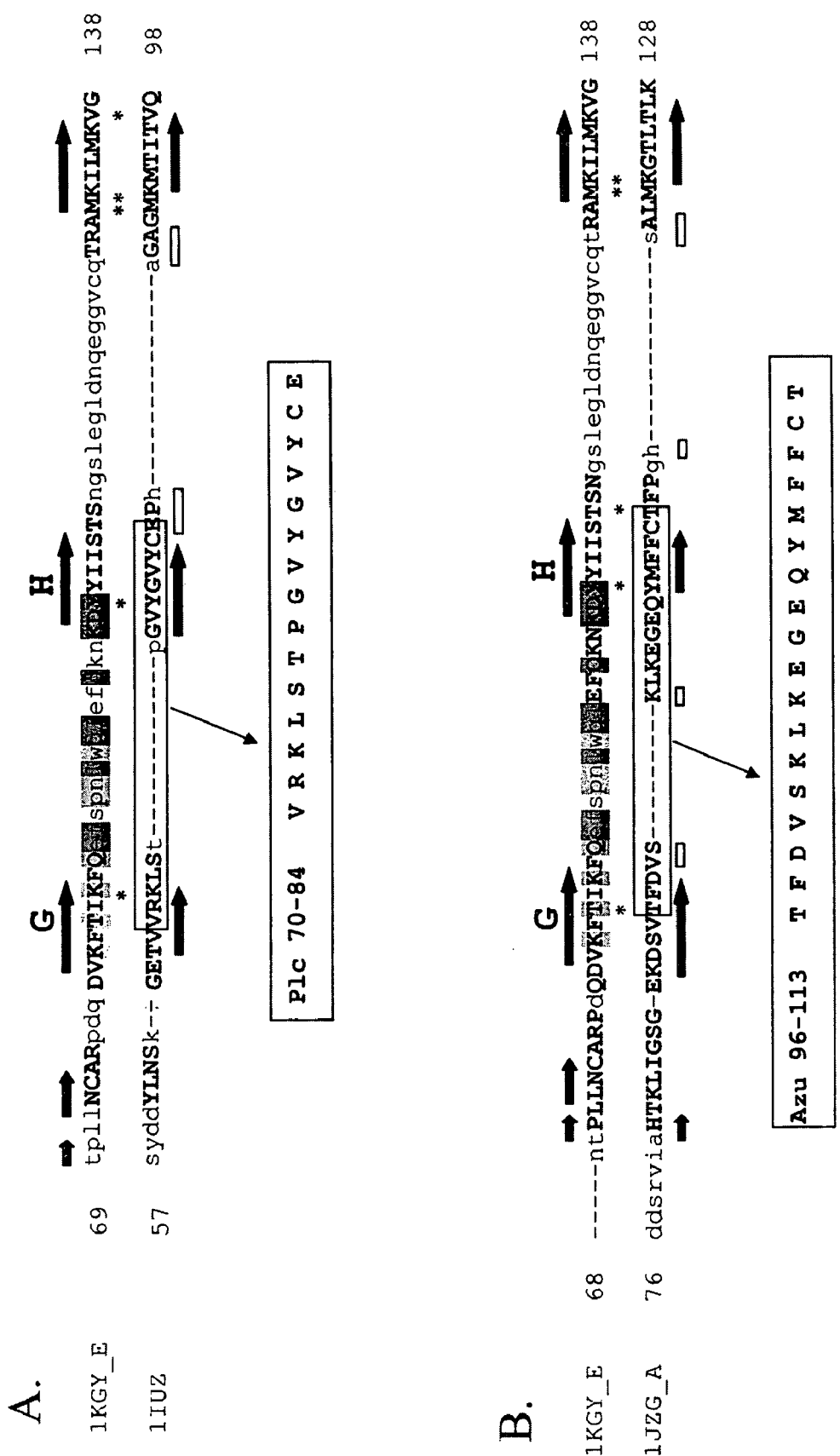
FIG. 8 depicts the structural alignment comprising the C-terminals of plastocyanin from *Ulva pertusa* (1IUZ) and azurin from *P. aeruginosa* (1JZG_A), (FIG. 8A and FIG. 8B respectively) with human ephrinB2 ectodomain (1KGY_E) as computed by the VAST algorithm. Superimposed secondary structure elements are denoted by a bold capital letter. Dashes and lower-case lettering are where there are no alignments. Secondary structure elements according to the structures are illustrated as arrows for β-sheets and open rectangles for 310 helices. Identical amino acids are indicated by an asterisk. Amino acids highlighted in dark gray and light gray in the ephrin B2 sequence indicate residues involved in the interaction between ephrinB2 and EphB2 receptor and in the ligand dimerization respectively (Himanen et al., Nature 414:933-938 (2001); Toth et al., Dev. Cell. 1:83-92 (2001)). The plastocyanin and azurin peptides (called Plc 70-84 (SEQ ID NO: 20) and Azu 96-113 (SEQ ID NO: 18), respectively), corresponding to the G-H loop region of ephrinB2, which is the main region mediating high affinity binding of the ephrins to the Eph receptors are boxed and represented below each alignment. The G and H loop regions are marked with thick arrows on top of the amino acid sequences of ephrinB2. 1KGY_E residues 69-138 and 68-138 are found in SEQ ID NOS: 31 and 33, respectively. 1IUZ residues 57-98 is found in SEQ ID NO: 32. 1JZG_A residues 76-128 is found in SEQ ID NO: 34.

Analysis of Cytotoxic Activity of Azu 96-113 and Plc70-84 Synthetic Peptides and GST-Azu Fusion Derivatives Toward Various Cancer Cell Lines Upon structure-based sequence alignment of azurin and plastocyanin with human ephrinB2 ectodomain, we designed the peptides corresponding to the G-H loop region of ephrinB2 (called Azu 96-113 (SEQ ID NO: 18) and Plc 70-84 (SEQ ID NO: 20)), which is the main region mediating high affinity binding of the ephrins to the Eph receptors (Himanen et al., *Nature* 414:933-938 (2001); Toth et al., *Dev. Cell.* 1:83-92 (2001)). In FIG. 8, the structural superimposition of the C-terminal segments of ephrinB2 ectodomain, azurin and plastocyanin can be seen. Structurally based sequence alignment of azurin and plastocyanin with human ephrinB2 ectodomain was used to design peptides based on the region mediating high affinity binding of the ephrinB2 to the EphB2 receptor (G strand-loop-H strand of the ephrinB2-Fc ectodomain) of azurin, namely Azu 96-113 (96-TFDVSKLKEGEQYMFFCT-113) (SEQ ID NO: 18) and plastocyanin, namely Plc 70-84 (70-VRKLST-PGVYGVYCE-84) (SEQ ID NO: 20) (FIG. 8). The peptides were purchased from GenScript Corporation (Piscataway, N.J.) as 99% pure. They were purified by reverse phase high-pressure liquid chromatography and their identity verified by mass spectrometry. Peptides were dissolved in phosphate-buffered saline (PBS) (1×) and stored in aliquots at −20° C. until use.

Figure 9:
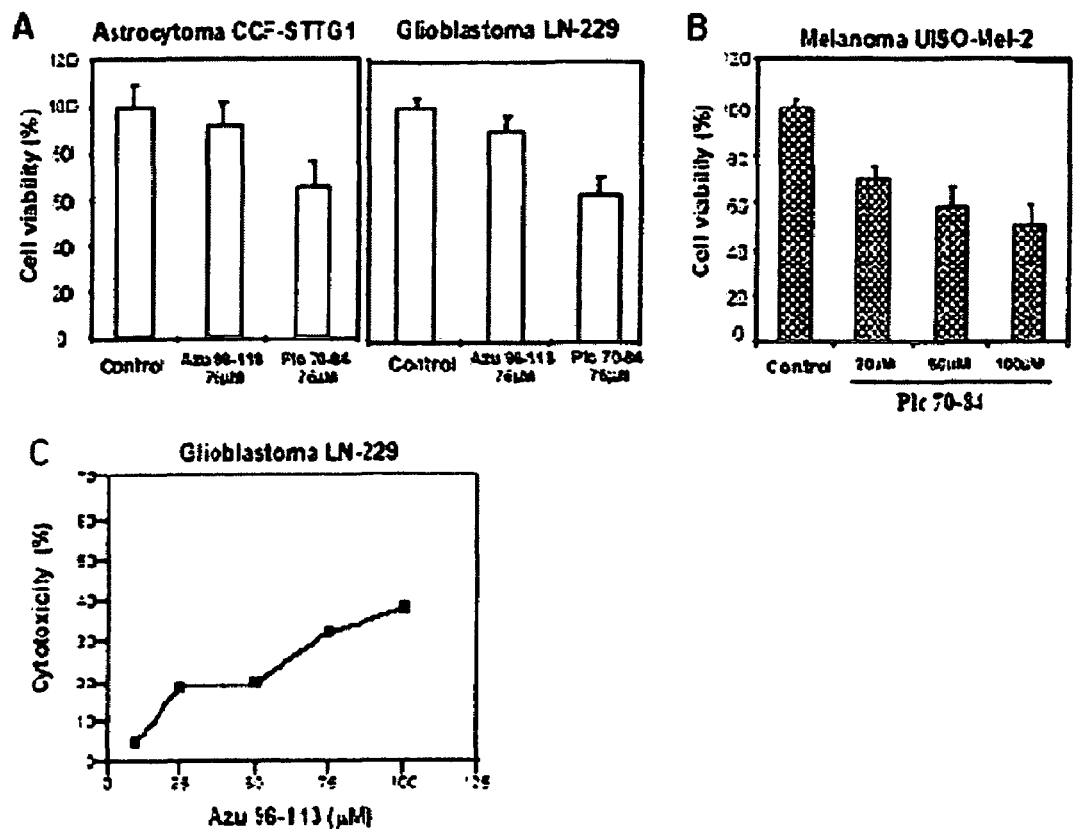
FIG. 9 depicts the effects of cupredoxin peptides on cancer cell viability.

In order to see if such domains of azurin may also play a role as antagonists to Eph signaling in cancer progression, we performed quantitative MTT assays in a number of cancer cell lines normally known to hyperexpress EphB receptors/ephrin ligands. During a 24 h incubation at 37° C., both azurin and plastocyanin G-H loop peptides at 75 μM showed induction of cell death in brain tumors astrocytoma CCF-STTG1 and glioblastoma LN-229 (FIG. 9A). The plastocyanin peptide Plc 70-84 showed somewhat higher cytotoxic activity than the azurin peptide Azu 96-113. To determine if such cytotoxicity is dose dependent and effective for other cancer cell lines, we evaluated the effect of several concentrations of these peptides on melanoma (FIG. 9B) or glioblastoma cells (FIG. 9C). In both cases, increasing peptide concentrations led to increasing cytotoxicity (FIGS. 9B and 9C).

Example 10

Analysis of the Ability of GST-Azu Fusion Peptides to Induce Cell Death in Breast Cancer MCF-7 Cells We have tested the ability of GST-Azu fusion peptides to induce cell death in breast cancer MCF-7 cells. For measurement of the cytotoxicity of the azurin and plastocyanin synthetic peptides, the 3-(4,5-dimethylthiazol-2-yl-2,5-diphenyl tetrazolium bromide) (MTT) (Sigma) assay (Mosmann, J. Immunol. Methods 65:55-63 (1983)). was conducted. Approximately $2 \times 10^4$ cells per well were seeded into 96-well culture plates in 100 μl of RPMI 1640 medium. After overnight growth, the supernatant was removed and new media containing azurin or plastocyanin synthetic peptides at various specified concentrations were added to the attached cells. After 24 or 48 h treatment, 10 μl of 5 mg/ml MTT solution was added to the culture and incubated for 1 h at 37° C. The MTT reaction was terminated by the addition of 40 mM HCl in isopropanol. The MTT formazan formed was measured spectrophotometrically as described earlier (Mosmann, 1983). Untreated control cells were compared to treated cells for determining viability and therefore a measure of cytotoxicity.

Figure 10:
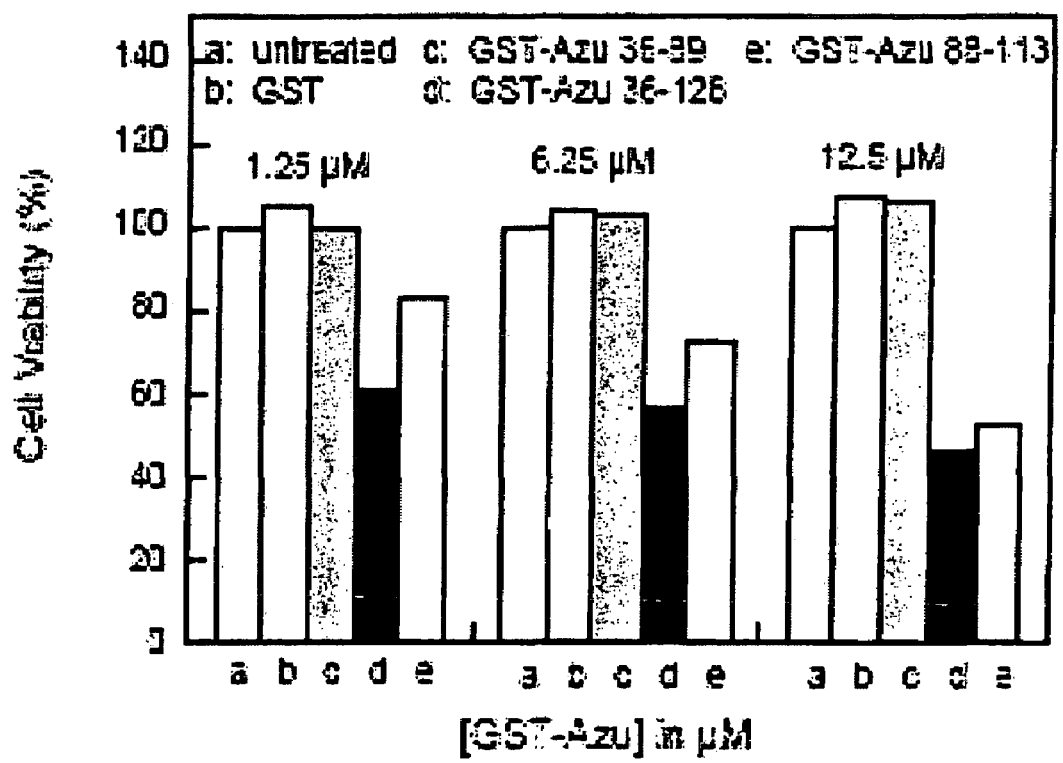
FIG. 10. Effect of GST-Azu 36-128 and GST-Azu 88-113 on cell viability of MCF-7 cells. GST-Azu peptides were added at increasing concentrations (1.25, 6.25 and 12.5 µM) into 96 well plates containing $8 \times 10^3$ cancer cells per well, incubated at 37° C. for 48 h and subsequently analyzed using MTT assay. GST and GST-Azu 36-89 at the same concentrations and untreated cells were run in parallel with GST-Azu 36-128 and GST-Azu 88-113 as controls.

There was very little cytotoxicity (FIG. 10) triggered by GST or GST-Azu 36-89 fusion protein similar to the control (without protein treatment). However, GST-Azu 36-128 or GST-Azu 88-113, harboring the azurin region capable of interfering in ephrinB2/EphB2 binding, showed significant cytotoxicity in a dose dependent manner confirming the role of the Azu 88-113 region in triggering MCF-7 cell death.

Example 11

Treatment of Patients Suffering from a Pathological Condition Related to Ephrin Signaling A Phase I/II clinical trial of a cupredoxin compound (Study Drug) is performed in patients suffering from cancer. Specifically, the cupredoxin compound is Plc 70-84 (SEQ ID NO: 20).

Forty-nine adult patients with histologically verified cancers of the breast, colon and melanoma who demonstrate clinical and radiographic progression or recurrence following adequate treatment by currently available FDA-approved chemotherapeutic drugs and regimen are enrolled in an open-label prospective study administering the Study Drug. To be eligible for enrollment in the study, all patients demonstrate increasing volume of measurable tumor after completion of approved course of chemotherapy regimens. The evidence of persistent metastatic deposits and/or continued increase in size or volume must be histologically established. This histological proof can be obtained by a fine needle aspiration (FNA) biopsy.

The treatment program is instituted after obtaining informed consent from all patients in accordance with the Institutional Review Board of the University of Illinois, Chicago and the FDA. The patients will have no intercurrent illness such as other malignancy, history of previous malignancy, blood dyscrasias, insulin dependent diabetes or other serious cardiovascular diseases which might interfere in appropriate evaluation of the effects of the proposed therapy. Baseline blood work (Complete Blood Counts [CBC] and Serum Chemistry) including liver function studies (LFT) is performed prior to initiation of therapy. All eligible patients must not receive any cancer chemotherapy concurrently during the period of the trial.

The study drug(s) is administered by daily intravenous injection of a pharmaceutically acceptable preparation of the Study Drug for 12 weeks and the subjects will be observed for any dose limiting toxicity. There will be 7 dose levels starting with 10 mg/kg/day and increasing by 5 mg/kg/day up to a maximum dose of 50 mg/kg/day. The efficacy of each dose level will be recorded in 7 patients with advanced measurable cancer (breast, colon, and melanoma).

The response is estimated by measuring the measurable tumor in 2 dimensions (a and b). 1) Total disappearance of the target metastatic tumors is considered as complete response (CR); 2) A 75% reduction is considered excellent, partial response (PR); and 3). A good response (PR) is post treatment reduction in size by 50%. 4) Reduction of 25% in size is considered as stable disease (SD) and 5)<25% is considered as no response (NR). Patients demonstrating a progression of disease have their treatment discontinued but will be followed for an additional 12 weeks.

Total disappearance, and any reduction in size of the target metastatic tumors will indicate that the azurin treatment is effective for treating cancer. Other indications that the Plc 70-84 treatment is effective are a decrease rate of in the appearance of new metastatic tumors and a decrease in the angiogenesis associated with tumors.

What is claimed is:

1. An isolated peptide that is a truncation, wherein said isolated peptide is selected from the group consisting of SEQ ID NOS:18, 25, and 34 of azurin, can inhibit the growth of mammalian cancer cells in vitro.

2. The isolated peptide of claim 1, wherein the azurin is from the organism *Pseudomonas aeruginosa*.

3. A composition, comprising the peptide of claim 1 in a pharmaceutical composition.

4. The composition of claim 3 wherein the azurin is from the organism *Pseudomonas aeruginosa*.

5. A kit comprising the composition of claim 3 in a vial.

* * * * *

UNITED STATES PATENT AND TRADEMARK OFFICE
CERTIFICATE OF CORRECTION

PATENT NO.        : 7,381,701 B2                                          Page 1 of 1
APPLICATION NO.   : 11/436592
DATED             : June 3, 2008
INVENTOR(S)       : Ananda Chakrabarty et al.

It is certified that error appears in the above-identified patent and that said Letters Patent is hereby corrected as shown below:

Column 1, lines 26-32:
"STATEMENT OF GOVERNMENTAL INTEREST
The subject matter of this application has been supported by research grants from the National Institutes of Health (NIH), Bethesda, Maryland, U.S.A., (Grant Numbers AI 16790-21, ES 04050-16, AI 45541, CA09432 and N01-CM97567). The government may have certain rights in this invention." should be deleted.

Signed and Sealed this

Seventeenth Day of August, 2010

David J. Kappos
*Director of the United States Patent and Trademark Office*